(12) United States Patent
Siegel et al.

(10) Patent No.: US 8,476,267 B2
(45) Date of Patent: Jul. 2, 2013

(54) IMIDAZO-, PYRAZOLOPYRAZINES AND IMIDAZOTRIAZINES AND THEIR USE

(75) Inventors: Stephan Siegel, Berlin (DE); Andreas Wilmen, Köln (DE); Susanne Röhrig, Hilden (DE); Niels Svenstrup, Velbert (DE); Mark Jean Gnoth, Mettman (DE); Stefan Heitmeier, Wülfrath (DE); Ulrich Rester, Wuppertal (DE); Adrian Tersteegen, Wuppertal (DE); Michael Gerisch, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 72 days.

(21) Appl. No.: 12/668,633

(22) PCT Filed: Jun. 28, 2008

(86) PCT No.: PCT/EP2008/005305
§ 371 (c)(1),
(2), (4) Date: Jun. 21, 2010

(87) PCT Pub. No.: WO2009/007029
PCT Pub. Date: Jan. 15, 2009

(65) Prior Publication Data
US 2011/0053929 A1     Mar. 3, 2011

(30) Foreign Application Priority Data
Jul. 11, 2007    (DE) .......................... 10 2007 032 349

(51) Int. Cl.
*A61K 31/535*    (2006.01)

(52) U.S. Cl.
USPC ...................................... 514/233.2

(58) Field of Classification Search
None
See application file for complete search history.

(56) References Cited

U.S. PATENT DOCUMENTS

| | | | |
|---|---|---|---|
| 2006/0106023 A1 | 5/2006 | Guzi et al. |
| 2006/0183746 A1 | 8/2006 | Currie et al. |

FOREIGN PATENT DOCUMENTS

| WO | 9964401 A2 | 12/1999 |
|---|---|---|
| WO | 03000693 A1 | 1/2003 |
| WO | 2003049739 A1 | 6/2003 |
| WO | 2004026877 A1 | 4/2004 |
| WO | 2006044687 A2 | 4/2006 |
| WO | 2007058873 A2 | 5/2007 |
| WO | 2007145921 A1 | 12/2007 |

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Anderson (Chem and Biol 10:787-797, 2003).*
Thiel (Nature Biotechnol 2:513-519, 2004).*
Woodgett Jr., Trends Biochem. Sci. (1991), 16(5), 177-81.
Wodarz A., Nusse R., Annu. Rev. Cell Dev. Biol. (1998), 14, 59-88.
Kirstetter et al., Nat Immunol. (2006), 7(10), 1048-56.
O'Brien et al., British Journal of Cancer (2006), 95, 1632-1636.
International Search Report, Application No. PCT/EP2008/005305, dated Oct. 16, 2008.

* cited by examiner

Primary Examiner — Craig Ricci

(57) ABSTRACT

The invention relates to substituted imidazo-, pyrazolopyrazines and imidazotriazines and processes for their preparation, and their use for the manufacture of medicaments for the treatment and/or prophylaxis of diseases, in particular of hematological disorders, preferably of leukopenias and neutropenias.

7 Claims, No Drawings

IMIDAZO-, PYRAZOLOPYRAZINES AND IMIDAZOTRIAZINES AND THEIR USE

The invention relates to substituted imidazo-, pyrazolopyrazines and imidazotriazines and processes for their preparation, and their use for the manufacture of medicaments for the treatment and/or prophylaxis of diseases, in particular of hematological disorders, preferably of leukopenias and neutropenias.

Glycogen synthase kinase 3 (GSK3) belongs to the families of serine/threonin kinases. Specific substrates are inter alia cytoskeletal proteins and transcription factors. Two isoforms, GSK3α and GSK3β, have been identified to date (Woodgett J R., Trends Biochem. Sci. (1991), 16(5), 177-81). Both isoforms are constitutively active in chiefly resting, non-proliferating cells.

GSK3β is of central importance within the Wnt/Wingless signal transduction pathway. The latter is one of the most important, evolutionarily conserved signalling systems. Wnt signals control very early patterning processes during embryogenesis, they induce mesoderm formation and many organs, and they control the proliferation and differentiation of stem cells (Wodarz A., Nusse R., Annu. Rev. Cell Dev. Biol. (1998), 14, 59-88; Kirstetter et al., Nat Immunol. (2006), 7(10), 1048-56). There is intracellular compartmentalization of the Wnt signalling pathway, thus making it possible to control a wide variety of processes. Within the Wnt cascade, glycogen synthase kinase 3 forms part of a multi-protein complex to which belong inter alia the structural molecules axin, the tumor suppressor protein APC and the transcription cofactor β-catenin. In this connection, β-catenin is the principal substrate of GSK3β.

The consequence of this GSK3β-mediated phosphorylation is the proteasomal degradation of β-catenin. Inhibition of GSK3 activity leads to an accumulation of β-catenin in the cell with subsequent translocation into the cell nucleus. There, β-catenin acts as a cofactor in transcription complexes and thus is partly responsible for the expression of defined target genes.

Radiotherapies or chemotherapies are among the standard approaches to controlling cancer. Both types of therapy are nonspecific in relation to their target cells, i.e. not only tumor cells but also untransformed, proliferating cells are affected. These untransformed, proliferating cells also include hematopoietic progenitor cells which develop inter alia into neutrophilic granulocytes. A significant reduction in the number of neutrophiles is referred to as neutropenia. A neutropenia induced by chemotherapy or radiotherapy results clinically in an increased susceptibility to infection. If the neutropenia is substantial there is an increase in the morbidity and, in some circumstances, also the mortality of a therapy (O'Brien et al., British Journal of Cancer (2006), 95, 1632-1636).

Inhibition of GSK3 activity leads to an increased rate of proliferation and differentiation of hematopoietic stem cells and can accordingly be utilized for therapeutic intervention in relation to a therapy-induced neutropenia.

WO99/064401 describes inter alia imidazopyrazines as somatostatin receptor ligands for the treatment of diabetes. WO2004/026877, US2006/0183746, US2006/0106023 and WO2007/058873 describe the use of imidazopyrazinylamines for the treatment of cancer. Pyrazolo- and imidazopyrazines for the treatment of cancer are disclosed in WO2006/044687. WO03/000693 claims imidazotriazines as PDE10 inhibitors for the treatment of neurodegenerative diseases. WO 2007/145921 describes imidazopyrazines as protein kinase inhibitors for the treatment of cancer.

One object of the present invention is therefore to provide novel compounds as GSK3β inhibitors for the treatment of hematological disorders, preferably of neutropenia in humans and animals.

The invention provides compounds of the formula

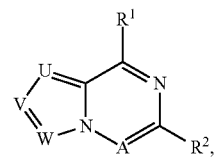

(I)

in which
either
U represents N,
V represents $CR^{12}$,
W represents CH,
A represents $CR^{15}$,
or
U represents CH,
V represents $CR^{12}$,
W represents N,
A represents $CR^{15}$,
or
U represents $CR^{16}$,
V represents N,
W represents $CR^{17}$,
A represents N,
where
$R^{12}$ represents hydrogen, hydroxyl, amino, hydroxycarbonyl, aminocarbonyl, trifluoromethyl, trifluoromethoxy, cyano, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulfonylamino, 5- or 6-membered heterocyclylcarbonyl, —$CH_2R^{13}$ or —$CH_2CH_2R^{14}$,
where heterocyclylcarbonyl may be substituted by 1 to 3 substituents, where the substituents independently of one another are selected from the group consisting of halogen, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
where alkoxy, alkylamino, alkylcarbonyl, alkoxycarbonyl, alkylaminocarbonyl, alkylcarbonylamino and alkylsulfonylamino may be substituted by a substituent,
where the substituent is selected from the group consisting of hydroxyl, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino, 5- or 6-membered heterocyclyl and phenyl,
where phenyl may be substituted by 1 to 3 substituents, where the substituents independently of one another are selected from the group consisting of halogen, cyano, trifluoromethyl, trifluoromethoxy, aminocarbonyl, $C_1$-$C_4$-alkyl, $C_1$-$C_4$-alkoxy, $C_{1\text{-}4}$-alkylamino, $C_1$-$C_4$-alkylcarbonyl, $C_1$-$C_4$-alkoxycarbonyl, $C_1$-$C_4$-alkylaminocarbonyl and $C_1$-$C_4$-alkylcarbonylamino,
and
where heterocyclyl may be substituted by 1 to 3 substituents, where the substituents independently of one another are selected from the group consisting of halogen, oxo, $C_1$-$C_4$-alkoxy, $C_1$-$C_4$-alkylcarbonyl, $C_1$-$C_4$-alkoxycarbonyl and $C_1$-$C_4$-alkylaminocarbonyl, and
where
$R^{13}$ represents hydroxyl, amino, cyano, hydroxycarbonyl, aminocarbonyl, $C_1$-$C_4$-alkoxy, $C_1$-$C_4$-alkoxycarbonyl, $C_1$-$C_4$-alkylaminocarbonyl, $C_1$-$C_4$-alkylcarbonylamino, $C_3$-$C_6$-cycloalkylamino or 5- or 6-membered heterocyclyl,
where alkoxy, alkylamino, alkoxycarbonyl, alkylaminocarbonyl and alkylcarbonylamino may be substituted by a substituent, where the substituent is selected from the group consisting of hydroxyl, amino, hydroxycarbonyl, aminocarbonyl, $C_1$-$C_4$-alkoxy, $C_1$-$C_4$-alkoxycarbonyl, $C_1$-$C_4$-alkylaminocarbonyl and $C_1$-$C_4$-alkylcarbonylamino,
and
where heterocyclyl may be substituted by 1 to 3 substituents, where the substituents independently of one another are selected from the group consisting of halogen, oxo, $C_1$-$C_4$-alkoxy, $C_1$-$C_4$-alkylcarbonyl, $C_1$-$C_4$-alkoxycarbonyl and $C_1$-$C_4$-alkylaminocarbonyl,
and
where
$R^{14}$ represents hydroxyl, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino or 5- or 6-membered heterocyclyl,
where alkoxy, alkylamino, alkoxycarbonyl, alkylaminocarbonyl and alkylcarbonylamino may be substituted by a substituent, where the substituent is selected from the group consisting of hydroxyl, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino,
and
where heterocyclyl may be substituted by 1 to 3 substituents, where the substituents independently of one another are selected from the group consisting of halogen, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
$R^{15}$ represents hydrogen, halogen, cyano, trifluoromethyl, $C_1$-$C_3$-alkyl, methoxy, methylthio or cyclopropyl,
$R^{16}$ represents hydrogen or methyl,
$R^{17}$ represents hydrogen or methyl,
$R^1$ represents a group of the formula

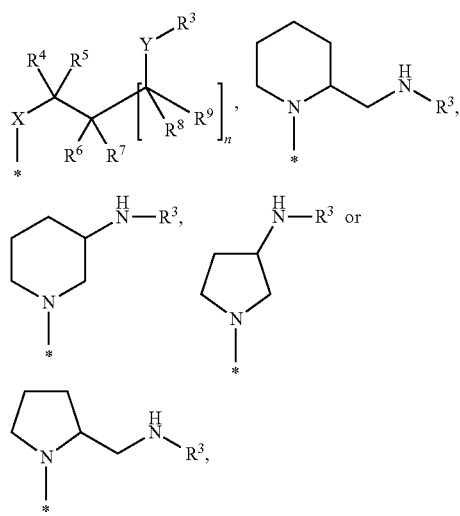

where
* is the point of attachment to the heterocycle,
n represents the number 0 or 1,
X represents $NR^{10}$, S or O, where
$R^{10}$ represents hydrogen, $C_1$-$C_3$-alkyl or cyclopropyl,
Y represents $NR^{11}$ or S,
where
$R^{11}$ represents hydrogen, $C_1$-$C_3$-alkyl or cyclopropyl,
$R^3$ represents pyrid-2-yl, pyrimid-2-yl, 2-aminopyrimid-4-yl, 2-(mono-$C_1$-$C_4$-alkylamino)pyrimid-4-yl, 2-(mono-$C_3$-$C_4$-cycloalkylamino)pyrimid-4-yl, pyridazin-3(2H)-on-6-yl, 1,3-oxazol-2-yl, 1,3-oxazol-4-yl, 1,2,4-oxadiazol-3-yl, 1,2,3-oxadiazol-4-yl, 1,3-thiazol-2-yl, 1,3-thiazol-4-yl, 1H-1,2,4-triazol-5-yl, 2,4-dihydro-3H-1,2,4-triazol-3-on-5-yl or 1,2-pyrazol-5-yl,
where pyrid-2-yl, pyrimid-2-yl, 1,3-oxazol-2-yl, 1,3-oxazol-4-yl, 1,3-thiazol-2-yl and 1,3-thiazol-4-yl are substituted by 1 or 2 substituents, where the substituents independently of one another are selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_3$-$C_4$-cycloalkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl,
where alkyl, alkoxy, alkylamino, alkylcarbonyl, alkoxycarbonyl, alkylaminocarbonyl and cycloalkylcarbonyl may be substituted by a substituent, where the substituent is selected from the group consisting of halogen, cyano, hydroxyl, amino, trifluoromethyl and $C_3$-$C_6$-cycloalkyl,
and
where 2-aminopyrimid-4-yl, 2-(mono-$C_1$-$C_4$-alkylamino)pyrimid-4-yl, 2-(mono-$C_3$-$C_4$-cycloalkylamino)pyrimid-4-yl, pyridazin-3(2H)-on-6-yl, 1,2,4-oxadiazol-3-yl, 1,2,3-oxadiazol-4-yl, 1H-1,2,4-triazol-5-yl, 2,4-dihydro-3H-1,2,4-triazol-3-on-5-yl and 1,2-pyrazol-5-yl may be substituted by a substituent, where the substituent is selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_3$-$C_4$-cycloalkylamino, $C_1$-$C_4$-alkoxycarbonyl, $C_1$-$C_4$-alkylaminocarbonyl and $C_3$-$C_6$-cycloalkylcarbonyl,
$R^4$ represents hydrogen, $C_1$-$C_3$-alkyl or cyclopropyl,
$R^5$ represents hydrogen or $C_1$-$C_3$-alkyl,
$R^6$ represents hydrogen, $C_1$-$C_3$-alkyl or cyclopropyl,
$R^7$ represents hydrogen or $C_1$-$C_3$-alkyl,
$R^8$ represents hydrogen, $C_1$-$C_3$-alkyl or cyclopropyl,
$R^9$ represents hydrogen or $C_1$-$C_3$-alkyl,
$R^2$ represents $C_6$-$C_{10}$-aryl or 5- to 10-membered heteroaryl, where aryl and heteroaryl may be substituted by 1 to 3 substituents, where the substituents independently of one another are selected from the group consisting of hydroxyl, hydroxymethyl, amino, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulfonyl, $C_1$-$C_4$-alkylsulfonylamino, $C_1$-$C_4$-alkylaminosulfonyl, phenyl, benzyloxy, 5- or 6-membered heterocyclyl, 5- or 6-membered heterocyclylcarbonyl, 5- or 6-membered heterocyclylmethyl and 5- or 6-membered heteroaryl,
where phenyl, benzyloxy, heterocyclyl, heterocyclylcarbonyl, heterocyclylmethyl and heteroaryl may be substituted by 1 to 3 substituents, where the substituents independently of one another are selected from the group consisting of halogen, cyano, trifluoromethyl, trifluoromethoxy, aminocarbonyl, $C_1$-$C_4$-alkyl, $C_1$-$C_4$-alkoxy, $C_1$-$C_4$-alkylamino, $C_1$-$C_4$- alkylcarbonyl, $C_1$-$C_4$-alkoxycarbonyl, $C_1$-$C_4$-alkylaminocarbonyl and $C_1$-$C_4$-alkylcarbonylamino, or two of the substituents on aryl together with the carbon atoms to which they are attached form a 1,3-dioxolane or 1,4-dioxane, and their salts, their solvates and the solvates of their salts.

Compounds according to the invention are the compounds of the formula (I) and the salts, solvates and solvates of the salts thereof, as well as the compounds encompassed by the formula (I) and mentioned below as exemplary embodiment(s), and the salts, solvates and solvates of the salts thereof, insofar as the compounds encompassed by formula (I) and mentioned below are not already salts, solvates and solvates of the salts.

The compounds of the invention may, depending on their structure, exist in stereoisomeric forms (enantiomers, diastereomers). The invention therefore encompasses the enantiomers or diastereomers and respective mixtures thereof. The stereoisomerically pure constituents can be isolated in a known manner from such mixtures of enantiomers and/or diastereomers.

Where the compounds of the invention can occur in tautomeric forms, the present invention encompasses all tautomeric forms.

Salts preferred for the purposes of the present invention are physiologically acceptable salts of the compounds of the invention. However, salts which are themselves unsuitable for pharmaceutical applications but can be used for example for isolating or purifying the compounds of the invention are also encompassed.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates refer for the purposes of the invention to those forms of the compounds of the invention which form a complex in the solid or liquid state through coordination with solvent molecules. Hydrates are a specific form of solvates in which the coordination takes place with water.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

For the purposes of the present invention, the substituents have, unless specified otherwise, the following meaning:

Alkyl per se and "alk" and "alkyl" in alkoxy, alkylamino, alkylcarbonyl, alkoxycarbonyl, alkylaminocarbonyl, alkylcarbonylamino, alkylsulfonyl, alkylsulfonylamino and alkylaminosulfonyl stand for a linear or branched alkyl radical having 1 to 4 carbon atoms, by way of example, and preferably for methyl, ethyl, n-propyl, isopropyl, n-butyl and tert-butyl.

Alkoxy stands by way of example and preferably for methoxy, ethoxy, n-propoxy, isopropoxy, n-butoxy and tert-butoxy.

Alkylamino stands for an alkylamino radical having one or two alkyl substituents (chosen independently of one another), by way of example and preferably for methylamino, ethylamino, n-propylamino, isopropylamino, tert-butylamino, N,N-dimethylamino, N,N-diethylamino, N-ethyl-N-methylamino, N-methyl-N-n-propylamino, N-isopropyl-N-n-propylamino and N-tert-butyl-N-methylamino. $C_1$-$C_4$-alkylamino stands for example for a monoalkylamino radical having 1 to 4 carbon atoms or for a dialkylamino radical having 1 to 4 carbon atoms in each alkyl substituent in each case.

Monoalkylamino stands for an alkylamino radical having a linear or branched alkyl substituent, by way of example and preferably for methylamino, ethylamino, n-propylamino, isopropylamino and tert-butylamino.

Monocycloalkylamino stands for a cycloalkylamino radical having a cycloalkyl substituent, where the other substituent at the amino radical is hydrogen, by way of example and preferably for cyclopropylamino and cyclobutylamino.

Alkylcarbonyl stands by way of example and preferably for methylcarbonyl, ethylcarbonyl, n-propylcarbonyl, isopropylcarbonyl, n-butylcarbonyl and tert-butylcarbonyl.

Alkoxycarbonyl stands by way of example and preferably for methoxycarbonyl, ethoxycarbonyl, n-propoxycarbonyl, isopropoxycarbonyl, n-butoxycarbonyl and tert-butoxycarbonyl.

Alkylaminocarbonyl stands for an alkylaminocarbonyl radical having one or two alkyl substituents (chosen independently of one another), by way of example and preferably for methylaminocarbonyl, ethylaminocarbonyl, n-propylaminocarbonyl, isopropylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N-tert-butyl-N-methylaminocarbonyl. $C_1$-$C_4$-Alkylaminocarbonyl stands for example for a monoalkylaminocarbonyl radical having 1 to 4 carbon atoms or for a dialkylaminocarbonyl radical having 1 to 4 carbon atoms in each alkyl substituent in each case.

Alkylcarbonylamino stands by way of example and preferably for methylcarbonylamino, ethylcarbonylamino, n-propylcarbonylamino, isopropylcarbonylamino, n-butylcarbonylamino and tert-butylcarbonylamino.

Alkylsulfonyl stands by way of example and preferably for methylsulfonyl, ethylsulfonyl, n-propylsulfonyl, isopropylsulfonyl, n-butylsulfonyl and tert-butylsulfonyl.

Alkylaminosulfonyl stands for an alkylaminosulfonyl radical having one or two alkyl substituents (chosen independently of one another), by way of example and preferably for methylaminosulfonyl, ethylaminosulfonyl, n-propylaminosulfonyl, isopropylaminosulfonyl, tert-butylaminosulfonyl, N,N-dimethylaminosulfonyl, N,N-diethylaminosulfonyl, N-ethyl-N-methylaminosulfonyl, N-methyl-N-n-propylaminosulfonyl, N-isopropyl-N-n-propylaminosulfonyl and N-tert-butyl-N-methylaminosulfonyl. $C_1$-$C_4$-Alkylaminosulfonyl stands for example for a monoalkylaminosulfonyl radical having 1 to 4 carbon atoms or for a dialkylaminosulfonyl radical having 1 to 4 carbon atoms in each alkyl substituent in each case.

Alkylsulfonylamino stands by way of example and preferably for methylsulfonylamino, ethylsulfonylamino, n-propylsulfonylamino, isopropylsulfonylamino, n-butylsulfonylamino and tert-butylsulfonylamino.

Cycloalkyl stands for a monocyclic cycloalkyl group usually having 3 to 6 carbon atoms, and mention may be made by way of example and preferably of cyclopropyl, cyclobutyl, cyclopentyl and cyclohexyl for cycloalkyl.

Cycloalkylamino stands for a cycloalkylamino radical having a cycloalkyl substituent, the other substituent at the amino radical being hydrogen or an alkyl radical, by way of example and preferably for cyclopropylamino, cyclobutylamino, N-cyclopropyl-N-methylamino and N-cyclobutyl-N-methylamino.

Heterocyclyl stands for a monocyclic, heterocyclic radical having 5 or 6 ring atoms and up to 3, preferably up to 2 heteroatoms and/or heterogroups from the series N, O, S, SO, $SO_2$, where a nitrogen atom may also form an N-oxide. The heterocyclyl radicals may be saturated or partly unsaturated. 5- or 6-membered, monocyclic saturated heterocyclyl radicals having up to 2 heteroatoms from the series O, N and S are preferred, by way of example and preferably for pyrrolidin-2-yl, pyrrolidin-3-yl, pyrrolinyl, tetrahydrofuranyl, tetrahydrothienyl, pyranyl, piperidin-1-yl, piperidin-2-yl, piperidin-3-yl, piperidin-4-yl, thiopyranyl, morpholin-1-yl, morpholin-2-yl, morpholin-3-yl, piperazin-1-yl, piperazin-2-yl.

Heteroaryl stands for an aromatic, mono- or bicyclic radical usually having 5 to 10, preferably 5 or 6 ring atoms and up to 5, preferably up to 4 heteroatoms from the series S, O and N, where a nitrogen atom may also form an N-oxide, by way of example and preferably for thienyl, furyl, pyrrolyl, thiazolyl, oxazolyl, oxadiazolyl, pyrazolyl, imidazolyl, pyridyl, pyrimidyl, pyridazinyl, pyrazinyl, indolyl, indazolyl, benzofuranyl, benzothiophenyl, quinolinyl, isoquinolinyl, benzoxazolyl, benzimidazolyl.

Halogen stands for fluorine, chlorine, bromine and iodine, preferably for fluorine and chlorine.

In the formulae of the group which can stand for $R^1$, the end point of the line, besides which a * stands in each case, does not stand for a carbon atom or a $CH_2$ group but forms part of the bond to the atom to which $R^1$ is bonded.

Preference is given to compounds of the formula (I) in which
either
U represents N,
V represents $CR^{12}$,
W represents CH,
A represents $CR^{15}$,
or
U represents CH,
V represents $CR^{12}$,
W represents N,
A represents $CR^{15}$,
or
U represents $CR^{16}$,
V represents N,
W represents $CR^{17}$,
A represents N,
where
$R^{12}$ represents hydrogen, hydroxycarbonyl, aminocarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, 5- or 6-membered heterocyclylcarbonyl, —$CH_2R^{13}$ or —$CH_2CH_2R^{14}$,
where heterocyclylcarbonyl may be substituted by 1 to 3 substituents, where the substituents independently of one another are selected from the group consisting of oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
where alkoxy, alkylamino, alkylcarbonyl, alkoxycarbonyl, alkylaminocarbonyl and alkylcarbonylamino may be substituted by a substituent, where the substituent is selected from the group consisting of hydroxyl, amino, hydroxycarbonyl, aminocarbonyl, $C_1$-$C_4$-alkoxy, $C_1$-$C_4$-alkylamino and 5- or 6-membered heterocyclyl,
where heterocyclyl may be substituted by 1 to 2 substituents, where the substituents independently of one another are selected from the group consisting of oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
where
$R^{13}$ represents hydroxyl, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino, $C_3$-$C_6$-cycloalkylamino or 5- or 6-membered heterocyclyl,
where alkoxy, alkylamino, alkoxycarbonyl, alkylaminocarbonyl and alkylcarbonylamino may be substituted by a substituent, where the substituent is selected from the group consisting of hydroxyl, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino,
and
where heterocyclyl may be substituted by 1 to 2 substituents, where the substituents independently of one another are selected from the group consisting of oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
where
$R^{14}$ represents hydroxyl, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino or 5- or 6-membered heterocyclyl,
where alkoxy, alkylamino, alkoxycarbonyl, alkylaminocarbonyl and alkylcarbonylamino may be substituted by a substituent, where the substituent is selected from the group consisting of hydroxyl, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino,
and
where heterocyclyl may be substituted by 1 to 2 substituents, where the substituents independently of one another are selected from the group consisting of oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
$R^{15}$ represents hydrogen, halogen, cyano or trifluoromethyl,
$R^{16}$ represents hydrogen or methyl,
$R^{17}$ represents hydrogen or methyl,
$R^1$ represents a group of the formula

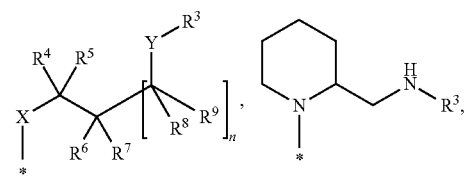

-continued

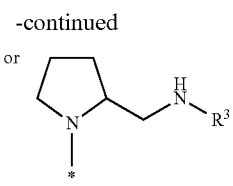

where
* is the point of attachment to the heterocycle,
n represents the number 0 or 1,
X represents $NR^{10}$, S or O,
where
$R^{10}$ represents hydrogen or methyl,
Y represents $NR^{11}$ or S,
where
$R^{11}$ represents hydrogen or methyl,
$R^3$ represents 2-pyridyl, pyrimid-2-yl, 2-aminopyrimid-4-yl, 1,3-oxazol-2-yl, 1,3-oxazol-4-yl, 1,2,4-oxadiazol-3-yl, 1,2,3-oxadiazol-4-yl, 1,3-thiazol-2-yl or 1,3-thiazol-4-yl,
where 2-pyridyl, pyrimid-2-yl, 1,3-oxazol-2-yl, 1,3-oxazol-4-yl, 1,3-thiazol-2-yl and 1,3-thiazol-4-yl are substituted by 1 or 2 substituents, where the substituents independently of one another are selected from the group consisting of halogen, cyano, nitro, amino, trifluoromethyl, trifluoromethoxy, aminocarbonyl, trifluoromethylcarbonyl methyl, ethyl, methoxy, ethoxy, $C_1$-$C_4$-alkylamino, methylcarbonyl, ethylcarbonyl, cyclopropylcarbonyl, methoxycarbonyl and ethoxycarbonyl, and
where 2-aminopyrimid-4-yl, 1,2,4-oxadiazol-3-yl and 1,2,3-oxadiazol-4-yl may be substituted by a substituent, where the substituent is selected from the group consisting of halogen, cyano, nitro, amino, trifluoromethyl, trifluoromethoxy, aminocarbonyl, trifluoromethylcarbonyl, methyl, ethyl, methoxy, ethoxy, $C_1$-$C_4$-alkylamino, methylcarbonyl, ethylcarbonyl, cyclopropylcarbonyl, methoxycarbonyl and ethoxycarbonyl,
$R^4$ represents hydrogen or methyl,
$R^5$ represents hydrogen or methyl,
$R^6$ represents hydrogen or methyl,
$R^7$ represents hydrogen or methyl,
$R^8$ represents hydrogen or methyl,
$R^9$ represents hydrogen or methyl,
$R^2$ represents $C_6$-$C_{10}$-aryl, thienyl, furyl, pyrrolyl, thiazolyl, oxazolyl, oxadiazolyl, pyrazolyl, imidazolyl, pyridyl, pyrimidyl, pyridazinyl, pyrazinyl, indolyl, indazolyl, quinolinyl, benzofuranyl or benzoxazolyl,
where aryl, thienyl, furyl, pyrrolyl, thiazolyl, oxazolyl, oxadiazolyl, pyrazolyl, imidazolyl, pyridyl, pyrimidyl, pyridazinyl, pyrazinyl, indolyl, indazolyl, quinolinyl, benzofuranyl and benzoxazolyl may be substituted by 1 to 3 substituents, where the substituents independently of one another are selected from the group consisting of hydroxyl, hydroxymethyl, amino, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulfonyl, $C_1$-$C_4$-alkylsulfonylamino, $C_1$-$C_4$-alkylaminosulfonyl, phenyl, benzyloxy, 5- or 6-membered heterocyclyl, 5- or 6-membered heterocyclylcarbonyl, 5- or 6-membered heterocyclylmethyl and 5- or 6-membered heteroaryl,
where phenyl, benzyloxy, heterocyclyl, heterocyclylcarbonyl, heterocyclylmethyl and heteroaryl may be substituted by 1 to 3 substituents, where the substituents independently of one another are selected from the group consisting of halogen, cyano, trifluoromethyl, trifluoromethoxy, aminocarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_1$-$C_4$-alkylcarbonylamino,
and their salts, their solvates and the solvates of their salts.

Preference is also given to compounds of the formula (I) in which
either
U represents N,
V represents $CR^{12}$,
W represents CH,
A represents $CR^{15}$,
or
U represents CH,
V represents $CR^{12}$,
W represents N,
A represents $CR^{15}$,
or
U represents $CR^{16}$,
V represents N,
W represents $CR^{17}$,
A represents N,
where
$R^{12}$ represents hydrogen, hydroxycarbonyl, aminocarbonyl, methyl, ethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, pyrrolidinylcarbonyl, piperidinylcarbonyl, piperazinylcarbonyl, morpholinylcarbonyl or —$CH_2R^{13}$,
where pyrrolidinylcarbonyl, piperidinylcarbonyl, piperazinylcarbonyl and morpholinylcarbonyl may be substituted by 1 to 2 substituents, where the substituents independently of one another are selected from the group consisting of oxo, methyl and ethyl,
and
where alkylcarbonyl, $C_2$-$C_4$-alkoxycarbonyl and $C_2$-$C_4$-alkylaminocarbonyl may be substituted by a substituent, where the substituent is selected from the group consisting of hydroxyl, amino, $C_1$-$C_4$-alkylamino, pyrrolidinyl, piperidinyl, piperazinyl and morpholinyl,
where pyrrolidinyl, piperidinyl, piperazinyl and morpholinyl may be substituted by 1 to 2 substituents, where the substituents independently of one another are selected from the group consisting of oxo, methyl and ethyl,
and
where
$R^{13}$ represents hydroxyl, amino, hydroxycarbonyl, aminocarbonyl, $C_1$-$C_4$-alkoxy, $C_1$-$C_4$-alkylamino, pyrrolidinyl, piperidinyl, piperazinyl or morpholinyl,
where pyrrolidinyl, piperidinyl, piperazinyl and morpholinyl may be substituted by 1 to 2 substituents, where the substituents independently of one another are selected from the group consisting of oxo, methyl and ethyl,
$R^{15}$ represents hydrogen,
$R^{16}$ represents hydrogen or methyl,
$R^{17}$ represents hydrogen or methyl,
$R^1$ represents a group of the formula

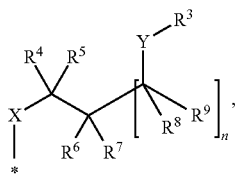

where
* is the point of attachment to the heterocycle,
n represents the number 0,
X represents $NR^{10}$,
where
$R^{10}$ represents hydrogen,
Y represents $NR^{11}$,
where
$R^{11}$ represents hydrogen or methyl,
$R^3$ represents 2-pyridyl, pyrimid-2-yl, 2-aminopyrimid-4-yl, 1,3-thiazol-2-yl or 1,3-thiazol-4-yl,
where 2-pyridyl, pyrimid-2-yl, 1,3-thiazol-2-yl and 1,3-thiazol-4-yl are substituted by 1 or 2 substituents, where the substituents independently of one another are selected from the group consisting of fluorine, chlorine, cyano, nitro, amino and trifluoromethyl,
and
where 2-aminopyrimid-4-yl may be substituted by a substituent, where the substituent is selected from the group consisting of fluorine, chlorine, cyano, nitro, amino and trifluoromethyl,
$R^4$ represents hydrogen,
$R^5$ represents hydrogen or methyl,
$R^6$ represents hydrogen,
$R^7$ represents hydrogen or methyl,
$R^8$ represents hydrogen,
$R^9$ represents hydrogen or methyl,
$R^2$ represents phenyl, thienyl, pyrazolyl or pyridyl,
where phenyl, thienyl, pyrazolyl and pyridyl may be substituted by 1 to 2 substituents, where the substituents independently of one another are selected from the group consisting of halogen, trifluoromethyl, trifluoromethoxy, aminocarbonyl, $C_1$-$C_4$-alkyl, $C_1$-$C_4$-alkoxy, $C_1$-$C_4$-alkoxycarbonyl, $C_1$-$C_4$-alkylaminocarbonyl, pyrrolidinyl, piperidinyl, morpholinyl and morpholinylcarbonyl,
and their salts, their solvates and the solvates of their salts.

Particular preference is given to compounds of the formula (I) in which either
U represents N,
V represents $CR^{12}$,
W represents CH,
A represents $CR^{15}$,
or
U represents CH,
V represents $CR^{12}$,
W represents N,
A represents $CR^{15}$,
or
U represents $CR^{16}$,
V represents N,
W represents $CR^{17}$,
A represents N,
where
$R^{12}$ represents hydrogen, hydroxycarbonyl, methyl, ethyl, methoxycarbonyl, ethoxycarbonyl, $C_1$-$C_4$-alkylaminocarbonyl, piperidinylcarbonyl or morpholinylcarbonyl,
where piperidinylcarbonyl and morpholinylcarbonyl may be substituted by a substituent, where the substituent is selected from the group consisting of methyl and ethyl,
and
where $C_2$-$C_4$-alkylaminocarbonyl may be substituted by a substituent, where the substituent is selected from the group consisting of $C_1$-$C_4$-alkylamino, piperazinyl and morpholinyl,
where piperazinyl and morpholinyl may be substituted by a substituent, where the substituent is selected from the group consisting of methyl and ethyl,
$R^{15}$ represents hydrogen,
$R^{16}$ represents methyl,
$R^{17}$ represents methyl,
$R^1$ represents a group of the formula

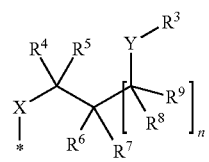

where
* is the point of attachment to the heterocycle,
n represents the number 0,
X represents $NR^{10}$,
where
$R^{10}$ represents hydrogen,
Y represents $NR^{11}$,
where
$R^{11}$ represents hydrogen or methyl,
$R^3$ represents a group of the formula

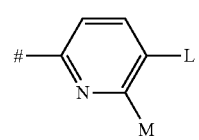

where
# is the point of attachment to Y,
L represents cyano, nitro or trifluoromethyl,
M represents hydrogen or amino,
$R^4$ represents hydrogen,
$R^5$ represents hydrogen or methyl,
$R^6$ represents hydrogen,
$R^7$ represents hydrogen or methyl,
$R^8$ represents hydrogen,
$R^9$ represents hydrogen,
$R^2$ represents phenyl,
where phenyl may be substituted by 1 to 2 substituents, where the substituents independently of one another are selected from the group consisting of fluorine, chlorine, trifluoromethyl, trifluoromethoxy, $C_1$-$C_3$-alkyl, methoxy, methoxycarbonyl and ethoxycarbonyl,
and their salts, their solvates and the solvates of their salts.

Preference is also given to compounds of the formula (I) in which either U represents N, V represents $CR^{12}$, W represents CH and A represents CH or U represents CH, V represents $CR^{12}$, W represents N and A represents CH or U represents $CR^{16}$, V represents N, W represents $CR^{17}$ and A represents N, where
R$^{12}$ represents hydrogen, hydroxycarbonyl, methyl, ethyl, methoxycarbonyl, ethoxycarbonyl, C$_1$-C$_4$-alkylaminocarbonyl, piperidinylcarbonyl or morpholinylcarbonyl,
where piperidinylcarbonyl and morpholinylcarbonyl may be substituted by a substituent, where the substituent is selected from the group consisting of methyl and ethyl,
and
where C$_2$-C$_4$-alkylaminocarbonyl may be substituted by a substituent, where the substituent is selected from the group consisting of C$_1$-C$_4$-alkylamino, piperazinyl and morpholinyl,
where piperazinyl and morpholinyl may be substituted by a substituent, where the substituent is selected from the group consisting of methyl and ethyl,
R$^{16}$ represents methyl,
and
R$^{17}$ represents methyl.

Preference is also given to compounds of the formula (I) in which U represents N, V represents CR$^{12}$, W represents CH and A represents CH,
where
R$^{12}$ represents hydrogen, hydroxycarbonyl, methyl, ethyl, methoxycarbonyl, ethoxycarbonyl, C$_1$-C$_4$-alkylaminocarbonyl, piperidinylcarbonyl or morpholinylcarbonyl,
where piperidinylcarbonyl and morpholinylcarbonyl may be substituted by a substituent, where the substituent is selected from the group consisting of methyl and ethyl,
and
where C$_2$-C$_4$-alkylaminocarbonyl may be substituted by a substituent, where the substituent is selected from the group consisting of C$_1$-C$_4$-alkylamino, piperazinyl and morpholinyl,
where piperazinyl and morpholinyl may be substituted by a substituent, where the substituent is selected from the group consisting of methyl and ethyl.

Preference is also given to compounds of the formula (I) in which U represents CH, V represents CR$^{12}$, W represents N and A represents CH,
where
R$^{12}$ represents hydrogen, hydroxycarbonyl, methyl, ethyl, methoxycarbonyl, ethoxycarbonyl, C$_1$-C$_4$-alkylaminocarbonyl, piperidinylcarbonyl or morpholinylcarbonyl,
where piperidinylcarbonyl and morpholinylcarbonyl may be substituted by a substituent, where the substituent is selected from the group consisting of methyl and ethyl,
and
where C$_2$-C$_4$-alkylaminocarbonyl may be substituted by a substituent, where the substituent is selected from the group consisting of C$_1$-C$_4$-alkylamino, piperazinyl and morpholinyl,
where piperazinyl and morpholinyl may be substituted by a substituent, where the substituent is selected from the group consisting of methyl and ethyl.

Preference is also given to compounds of the formula (I) in which U represents CR$^{16}$, V represents N, W represents CR$^{17}$ and A represents N, where R$^{16}$ and R$^{17}$ represents methyl.

Preference is also given to compounds of the formula (I) in which R$^1$ represents —NHCH$_2$CH$_2$NH—R$^3$, where R$^3$ represents 5-cyanopyrid-2-yl.

Preference is also given to compounds of the formula (I) in which n represents the number 0.

Preference is also given to compounds of the formula (I) in which X represents NR$^{10}$, where R$^{10}$ represents hydrogen.

Preference is also given to compounds of the formula (I) in which Y represents NR$^{11}$, where R$^{11}$ represents hydrogen.

Preference is also given to compounds of the formula (I) in which R$^3$ represents 5-cyanopyrid-2-yl.

Preference is also given to compounds of the formula (I) in which R$^4$, R$^5$, R$^6$, R$^7$, R$^8$ and R$^9$ represents hydrogen.

The invention furthermore provides a process for preparing the compounds of the formula (I), or their salts, their solvates or the solvates of their salts, where

[A] the compounds of the formula

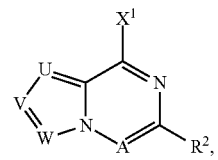

(II)

in which
A, U, V, W and R$^2$ have the meaning given above,
and
X$^1$ represents halogen, preferably chlorine or fluorine,
are reacted with compounds of the formula

R$^1$—H    (III), in which
R$^1$ has the meaning given above,
or

[B] the compounds of the formula

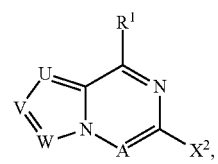

(IV)

in which
R$^1$ has the meaning given above,
and
A represents CR$^{15}$,
where R$^{15}$ has the meaning given above,
U represents N,
V represents CR$^{12}$,
where R$^{12}$ has the meaning given above,
W represents CH,
X$^2$ represents iodine, bromine, chlorine or trifluoromethanesulfonyl, preferably iodine or bromine,
are reacted under Suzuki coupling conditions with compounds of the formula

Q—R$^2$    (V), in which
R$^2$ has the meaning given above, and
Q represents —B(OH)$_2$, a boronic acid ester, preferably boronic acid pinacolate, or —BF$_3^-$K$^+$, to give compounds of the formula

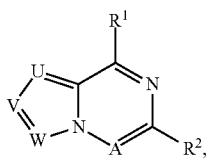

(Ia)

in which
R¹ and R² have the meaning given above,
and
A represents $CR^{15}$,
where $R^{15}$ has the meaning given above,
U represents N,
V represents $CR^{12}$,
where $R^{12}$ has the meaning given above,
W represents CH.

The compounds of the formula (Ia) are a subset of the compounds of the formula (I).

The reaction according to process [A] is generally carried out in inert solvents, where appropriate in the presence of a base, where appropriate in a microwave, preferably in a temperature range from 50° C. to 200° C. under atmospheric pressure up to 3 bar.

Examples of bases are alkali metal carbonates, such as, for example, sodium carbonate, potassium carbonate or cesium carbonate, or organic bases, such as trialkylamines, for example triethylamine, N-methylmorpholine, N-methylpiperidine, 4-dimethylaminopyridine or diisopropylethylamine, or other bases, such as, for example, sodium hydride or potassium tert-butoxide; preference is given to diisopropylethylamine or sodium hydride.

Examples of inert solvents are halogenated hydrocarbons, such as methylene chloride or trichloromethane, alcohols, such as methanol, ethanol, n-propanol or isopropanol, or ethers, such as dioxane or tetrahydrofuran, or other solvents, such as, for example, dimethyl sulfoxide, dimethylformamide or N-methylpyrrolidone, or mixtures of these solvents; preference is given to isopropanol or dimethyl sulfoxide.

The reaction according to process [B] is generally carried out in inert solvents, in the presence of a catalyst, where appropriate in the presence of an additive, where appropriate in a microwave, preferably in a temperature range from room temperature to 150° C. under atmospheric pressure up to 3 bar.

Examples of catalysts for Suzuki reaction conditions are customary palladium catalysts; preference is given to catalysts such as, for example, dichlorobis(triphenylphosphine)palladium, tetrakistriphenylphosphinepalladium(0), palladium(II) acetate/tricyclohexylphosphine, bis(diphenylphosphaneferrocenyl)palladium(II) chloride, 1,3-bis(2,6-diisopropylphenyl)imidazol-2-ylidene(1,4-naphthtoquinone)palladium dimer, allyl(chloro)(1,3-dimesityl-1,3-dihydro-2H-imidazol-2-ylidene)palladium or palladium(II) acetate/dicyclohexyl-(2',4',6'-triisopropylbiphenyl-2-yl)phosphine. Another suitable source of palladium is tris(dibenzylideneacetone)dipalladium.

Examples of additives are potassium acetate, cesium carbonate, potassium carbonate or sodium carbonate, potassium tert-butoxide, cesium fluoride or potassium phosphate carried out; preference is given to additives such as, for example, potassium acetate and/or aqueous sodium carbonate solution.

Examples of inert solvents are ethers, such as dioxane, tetrahydrofuran or 1,2-dimethoxyethane, hydrocarbons, such as benzene, xylene or toluene, or carboxamides, such as dimethylformamide or dimethylacetamide, alkyl sulfoxides, such as dimethyl sulfoxide, or N-methylpyrrolidone or acetonitrile, or mixtures of the solvents with alcohols, such as methanol or ethanol, and/or water; preference is given to dioxane or acetonitrile or a mixture of one of these solvents with water.

The compounds of the formulae (II) and (IV) are known, they can be synthesized by known processes from the appropriate starting materials or they can be prepared analogously to processes described in the example section (Example 3A to 5A, Example 9A, Example 10A to 12A and Example 13A to 16A) or analogously to J. Org. Chem. (2005), 70 (18), 7331-7337 and WO 03/000693.

The compounds of the formula (III) are known, they can be synthesized by known processes from the appropriate starting materials or they can be prepared analogously to the processes described in the example section (Example 1A to 2A and Example 6A to 8A).

The compounds of the formula (V) are known or they can be synthesized by known processes from the appropriate starting materials.

The preparation of the starting materials and the compounds of the formula (I) can be illustrated by the synthesis schemes below.

Scheme 1: Preparation of imidazo[1,2-a]pyrazines

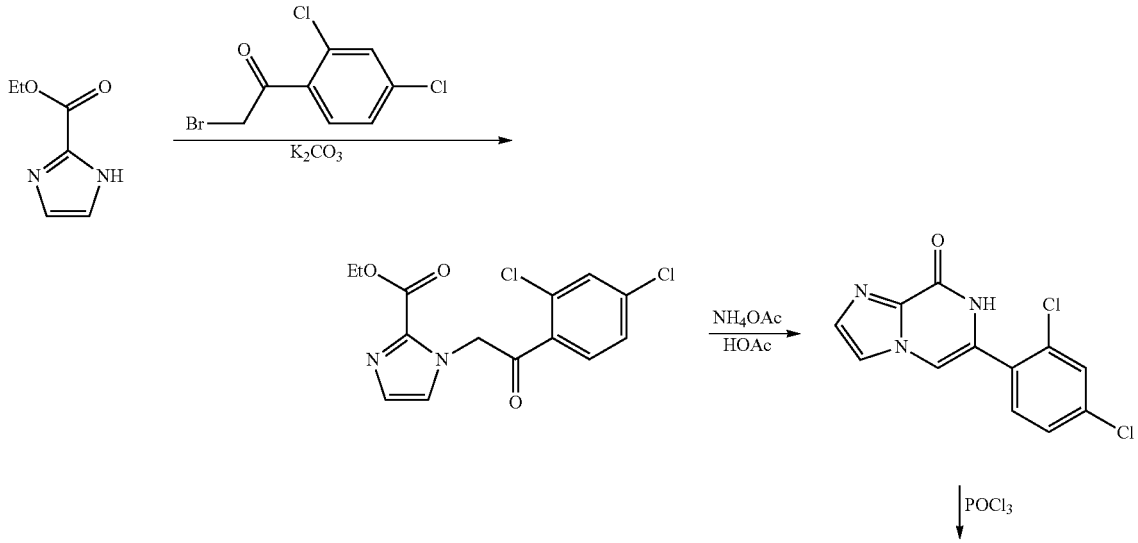

17 18
-continued
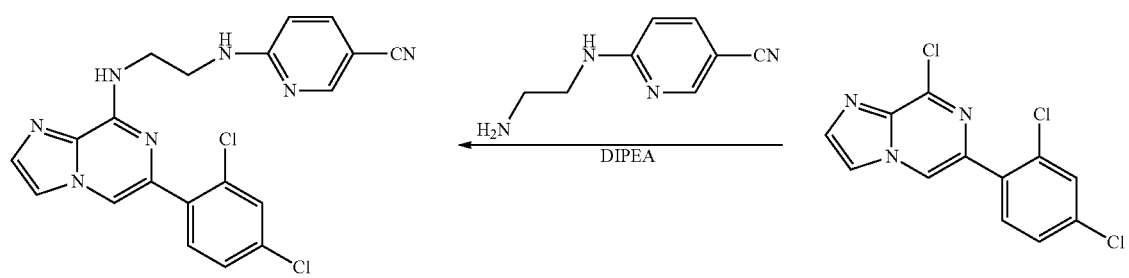
Scheme 2: Preparation of pyrazolo[1,5-a]pyrazines
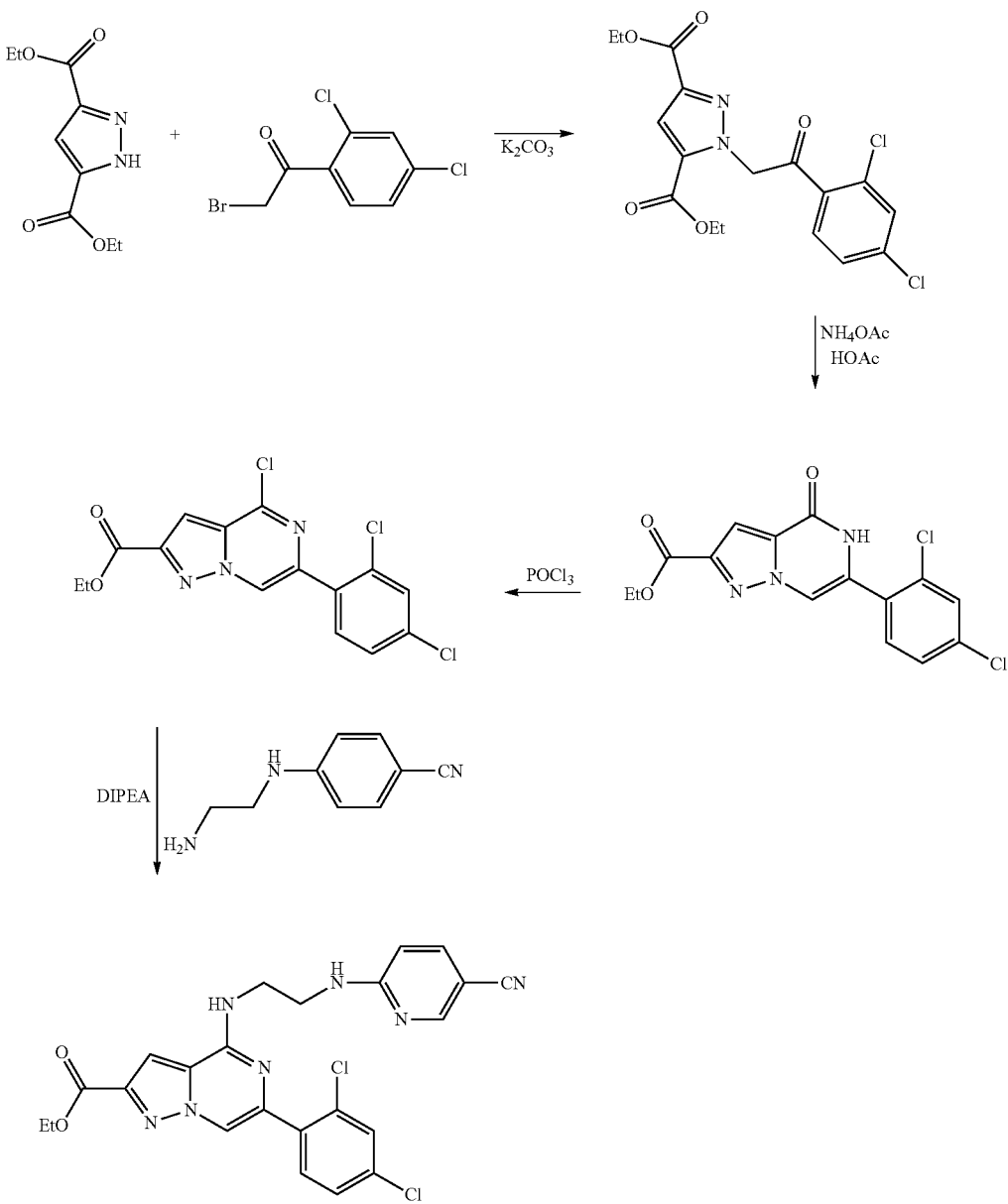

Scheme 3: Preparation of imidazo[5,1-f][1,2,4]triazines

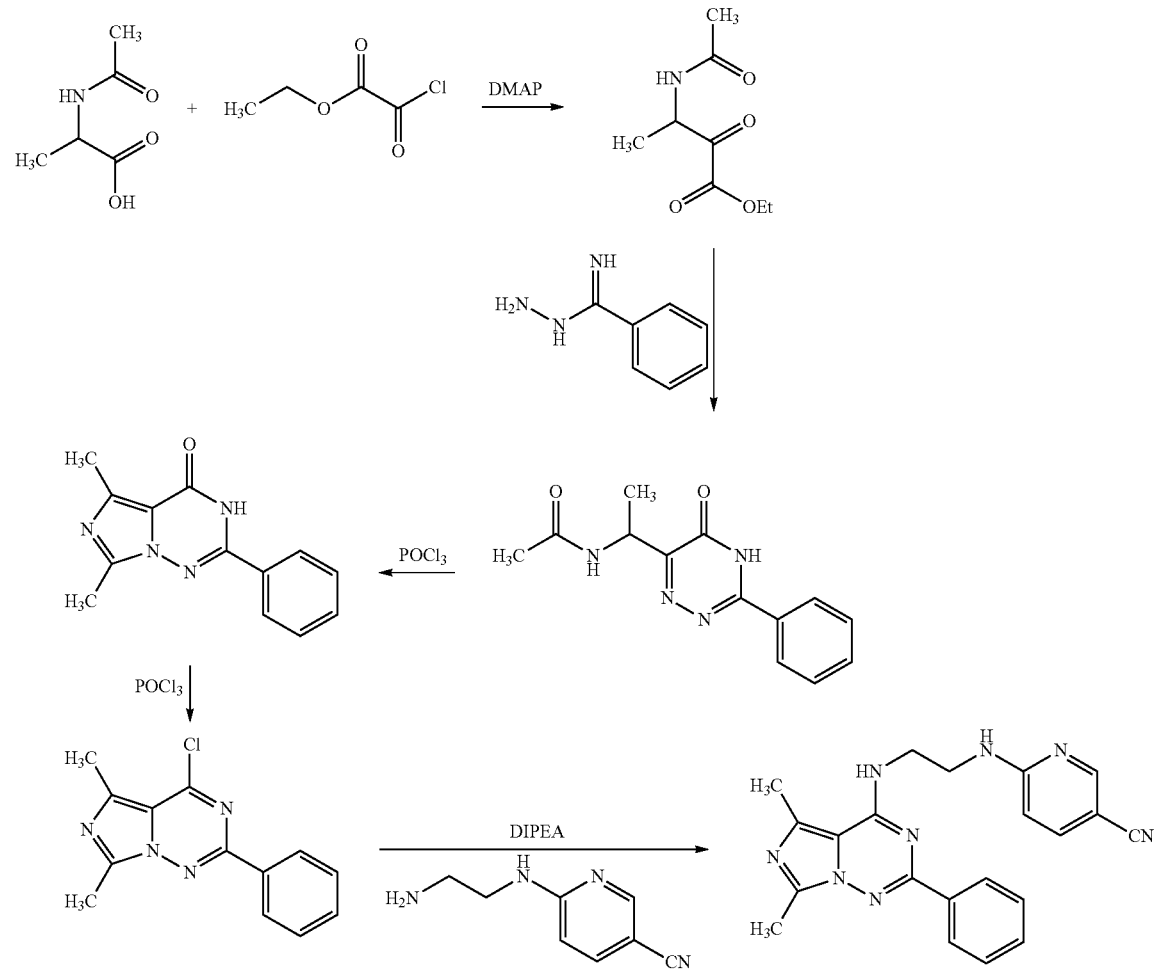

The compounds according to the invention show a valuable range of pharmacological and pharmacokinetic effects which could not have been predicted.

They are therefore suitable of use as medicaments for the treatment and/or prophylaxis of diseases in humans and animals.

The present invention further relates to the use of the compounds according to the invention for the treatment and/or prophylaxis of disorders, preferably hematological disorders, especially of leukopenias and neutropenia.

The compounds according to the invention are therefore suitable for the prophylaxis and/or treatment of neurodegenerative disorders such as, for example, Alzheimer's, Parkinson's, schizophrenia, degeneration, dementia, depression, aggression, cerebrovascular ischemia, sleep disorders, Huntington's chorea, neurotraumatic disorders such as, for example, stroke; type 2 diabetes mellitus and associated disorders such as, for example, the metabolic syndrome or obesity, type 1 diabetes mellitus, diabetic nephropathy, diabetic neuropathy, diabetic retinopathy, glomerulonephritis, hypercalcemia, hyperglycemia, hyperlipidemia, glucose-galactose malabsorption, general endocrine dysfunctions such as, for example, pancreatitis; hematological disorders such as, for example, acquired and congenital neutropenia, medicament-induced neutropenia, parasite-induced neutropenia, chemotherapy-induced neutropenia, granulocytopenia, acquired and congenital leukopenia, acquired and congenital anemia, hemolytic anemia, sickle cell anemia, acquired and congenital thrombocytopenia, leukocyte dysfunctions, impairments of blood coagulation, ex vivo expansion of embryonic and adult stem cells, ex vivo differentiation of embryonic and adult stem cells, bone marrow, graft-versus-host reaction; cancer such as, for example, glaucoma, breast carcinoma, colon tumor, gastrointestinal tumors, Hodgkin's lymphoma, non-Hodgkin's lymphoma, Kaposi sarcoma, liver tumor, pancreatic tumor, skin tumor, bone marrow tumor, leukemias such as, for example, acute lymphatic leukemia, acute myeloid leukemia, chronic myeloid leukemia, chronic lymphatic leukemia, prostate tumors, lung cancer, renal tumors; asthma, progressive, not completely reversible obstruction of the respiratory tract, pneumonia, pulmonary dysfunction; inflammatory disorders such as, for example, autoimmune diseases such as multiple sclerosis, rheumatoid arthritis, infections by gram-negative and gram-positive bacteria, viral infections, fungal infections such as, for example, by *Candida albicans*, HIV infections and HIV-associated infections, hepatitis of types A, B and C, parasitic infections; hair loss; reduced sperm mobility; wound healing; osteoporosis, bone marrow disorders, bone and joint disorders; cardiovascular disorders such as, for example, cardiac defects, heart failure, cardiac fibrosis, cardiac arrhythmias, myocardial infarction, medicament- or substance-induced cardiotoxicity, atherosclerosis, high blood pressure.

The compounds according to the invention are particularly suitable for the prophylaxis and/or treatment of neurodegenerative disorders, such as, for example, Alzheimer's disease and schizophrenia, of type II diabetes mellitus and associated disorders, of cancer, of leukopenias and/or of neutropenias.

The compounds according to the invention can additionally be employed also for efficient ex vivo expansion of adult hematopoietic stem cells from the bone marrow, from peripheral blood or from umbilical cord blood.

These cells expanded in this way can then be used to curtail the cytopenias induced by myeloablative therapies or within the framework of therapeutic transplantation methods or for hematological systemic disorders such as, for example, leukemias, or with cells which have been genetically manipulated after expansion for gene therapies.

The present invention further relates to the use of the compounds according to the invention for the treatment and/or prophylaxis of disorders, especially of the aforementioned disorders.

The present invention further relates to the use of the compounds according to the invention for the manufacture of a medicament for the treatment and/or prophylaxis of disorders, especially of the aforementioned disorders.

The present invention further relates to a method for the treatment and/or prophylaxis of disorders, in particular of the aforementioned disorders, by use of a therapeutically effective amount of a compound according to the invention.

The present invention further relates to medicaments comprising a compound according to the invention and one or more further active ingredients.

The present invention further relates to a method for the ex vivo expansion of adult hematopoietic stem cells from bone marrow, from peripheral blood or from umbilical cord blood, which is characterized in that an effective amount of the compound according to the invention is added.

The compounds of the invention can act systemically and/or locally. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds of the invention can be administered in administration forms suitable for these administration routes.

Suitable for oral administration are administration forms which function according to the prior art and deliver the compounds of the invention rapidly and/or in modified fashion, and which contain the compounds of the invention in crystalline and/or amorphized and/or dissolved form, such as, for example, tablets (uncoated or coated tablets, for example having enteric coatings or coatings which are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Oral administration is preferred.

Suitable for the other administration routes are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavours and/or odours.

The present invention further relates to medicaments which comprise at least one compound of the invention, preferably together with one or more inert, non-toxic, pharmaceutically suitable excipients, and to the use thereof for the aforementioned purposes.

It has generally proved advantageous on parenteral administration to administer amounts of about 5 to 500 mg every 24 hours to achieve effective results. The amount on oral administration is about 5 to 500 mg every 24 hours.

It may nevertheless be necessary where appropriate to deviate from the stated amounts, in particular as a function of the body weight, route of administration, individual response to the active ingredient, nature of the preparation and time or interval over which administration takes place.

The percentage data in the following tests and examples are, unless indicated otherwise, percentages by weight; parts are parts by weight. Solvent ratios, dilution ratios and concentration data of liquid/liquid solutions are in each case based on volume. The statement "w/v" means "weight/volume". Thus, for example, "10% w/v" means: 100 ml of solution or suspension comprise 10 g of substance.

A) EXAMPLES

Abbreviations

| | |
|---|---|
| abs. | absolute |
| Boc | tert-butoxycarbonyl |
| CDCl$_3$ | deuterochloroform |
| conc. | concentrated |
| d | day |
| DIEA | N,N-diisopropylethylamine |
| DMAP | 4-N,N-dimethylaminopyridine |
| DMF | dimethylformamide |
| DMSO | dimethyl sulfoxide |
| EDC | N'-(3-dimethylaminopropyl)-N-ethylcarbodiimide × HCl |
| eq. | equivalent |
| ESI | electrospray ionization (in MS) |
| h | hour |
| HOBt | 1-hydroxy-1H-benzotriazole × H$_2$O |
| HPLC | high pressure, high performance liquid chromatography |
| LC-MS | coupled liquid chromatography-mass spectrometry |
| min. | minutes |
| MS | mass spectrometry |
| MW | molecular weight [g/mol] |
| NMR | nuclear magnetic resonance spectroscopy |

| | |
|---|---|
| OAc | acetate |
| OEt | ethoxy |
| p.a. | per analysis |
| PyBOP | 1-benzotriazolyloxytripyrrolidinophosphonium hexafluorophosphate |
| $R_f$ | retention index (in TLC) |
| sat. | saturated |
| RP-HPLC | reverse phase HPLC |
| RT | room temperature |
| $R_t$ | retention time (in HPLC) |
| TBTU | (benzotriazol-1-yloxy)bisdimethylaminomethylium fluoroborate |
| TFA | trifluoroacetic acid |
| THF | tetrahydrofuran |

LC-MS Methods:

Method 1: Instrument: Micromass Quattro LCZ with HPLC Agilent series 1100; column: Phenomenex Synergi 2.5μ MAX-RP 100A mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 2: MS instrument type: Micromass ZQ; HPLC instrument type: Waters Alliance 2795; column: Merck Chromolith SpeedROD RP-18e 100 mm×4.6 mm; eluent A: water+500 μl of 50% formic acid/l; eluent B: acetonitrile+500 μl of 50% formic acid/l; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm Method 3: MS instrument type: Micromass ZQ; HPLC instrument type: HP 1100 Series; UV DAD; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 4: Instrument: Micromass Platform LCZ with HPLC Agilent series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 5: MS instrument type: Waters ZQ; HPLC instrument type: Waters Alliance 2795; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 210 nm.

Method 6: MS instrument type: Micromass ZQ; HPLC instrument type: Waters Alliance 2795; column: Phenomenex Synergi 2.5μ MAX-RP 100A mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 7: Instrument: Micromass Quattro LCZ with HPLC Agilent series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

Method 8: Instrument: Micromass QuattroPremier with Waters HPLC Acquity; column: Thermo Hypersil GOLD 1.9μ 50 mm×1 mm; eluent A: 1 l of water+0.5 ml of 50% formic acid, eluent B: 1 l of acetonitrile+0.5 ml of 50% formic acid; gradient: 0.0 min 100% A→0.1 min 100% A→1.5 min 10% A→2.2 min 10% A; oven: 50° C.; flow rate: 0.33 ml/min; UV detection: 210 nm.

Method 9: Instrument: Micromass Quattro Micro MS with HPLC Agilent series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A→4.01 min 100% A→5.00 min 100% A; flow rate: 0.0 min/3.0 min/4.0 min/4.01 min 2.5 ml/min, 5.00 min 2 ml/min; oven: 50° C.; UV detection: 210 nm.

Method 10: MS instrument: Waters ZQ 2000; HPLC instrument: Agilent 1100, 2-column setup, autosampler: HTC PAL; column: YMC-ODS-AQ, 50 mm×4.6 mm, 3.0 μm; eluent A: water+0.1% formic acid, eluent B: acetonitrile+0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Method 11: MS instrument: Micromass TOF (LCT); HPLC instrument: Waters 2690, autosampler: Waters 2700; column: YMC-ODS-AQ, 50 mm×4.6 mm, 3.0 μm; eluent A: water+0.1% formic acid, eluent B: acetonitrile+0.1% formic acid; gradient: 0.0 min 100% A-0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Starting Materials

Example 1A tert-Butyl {2-[(5-cyanopyridin-2-yl)amino]ethyl}carbamate

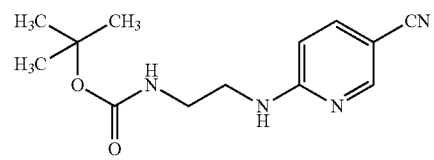 [SMILES: CC(C)(C)OC(=O)NCCNc1ccc(C#N)cn1]

5.5 g (39.7 mmol) of 6-chloronicotinonitrile were dissolved in 70 ml of DMSO, and 10.2 g (63.5 mmol) of N-Boc-ethylenediamine and 11 g (79.4 mmol) of potassium carbonate were added. The mixture was stirred at 90° C. for 12 h. The residue was taken up in a mixture of water and ethyl acetate. The organic phase was washed with saturated aqueous sodium chloride solution, dried over magnesium sulfate and concentrated on a rotary evaporator. The residue was chromatographed on silica gel 60 (mobile phase: cyclohexane/ethyl acetate 10:1 to 2:1). This gave 7.9 g (77% of theory) of the product as a solid.

LCMS (method 6): $R_t$=1.46 min. (m/z=263 (M+H)$^+$)

$^1$H-NMR (400 MHz, DMSO-d$_6$): δ=8.37 (d, 1H), 7.66 (d, 1H) 7.6 (s, 1H), 6.87 (t, 1H), 6.53 (d, 1H), 3.32 (q, 2H), 3.09 (q, 2H), 1.37 (s, 9H).

Example 2A

6-[(2-Aminoethyl)amino]nicotinonitrile dihydrochloride

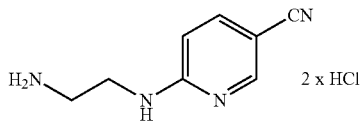 [SMILES: N#Cc1ccc(NCCN)nc1]

7.9 g (30 mmol) of tert-butyl {2-[(5-cyanopyridin-2-yl)amino]ethyl}carbamate (Example 1A) were dissolved in 100 ml of 4N hydrogen chloride in dioxane and the mixture was stirred for 30 min. The reaction mixture was concentrated to half of its original volume and the same amount of diethyl ether was added. The reaction mixture was stirred for 20 min and the product was filtered off and washed with diethyl ether. This gave 7 g (94% of theory) of the product as a solid.

LCMS (method 4): $R_t$=0.51 min. (m/z=162 (M+H)$^+$)

$^1$H-NMR (400 MHz, DMSO-d$_6$): δ=8.44 (s, 1H), 7.76 (d, 1H), 6.67 (d, 1H), 3.58 (t, 2H), 2.98 (q, 2H).

Example 3A

Ethyl 1-[2-(2,4-dichlorophenyl)-2-oxoethyl]-1H-imidazole-2-carboxylate

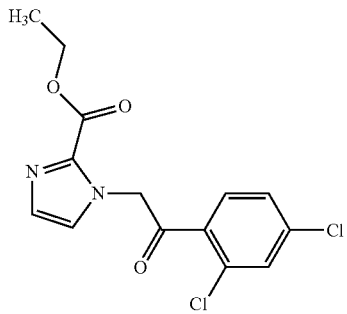 [SMILES: CCOC(=O)c1nccn1CC(=O)c1ccc(Cl)cc1Cl]

0.5 g (3.6 mmol) of imidazole-2-carboxylate ethyl were dissolved in 35 ml of acetone, and 0.96 g (3.6 mmol) of 2-bromo-2,4-dichloroacetophenone and 0.49 g (3.6 mmol) of potassium carbonate were added. The mixture was stirred at RT for 12 h. The reaction mixture was concentrated and taken up in water and dichloromethane. The organic phase was washed with saturated aqueous sodium chloride solution, dried over magnesium sulfate and concentrated on a rotary evaporator. The residue was triturated with diethyl ether and the solid was filtered off with suction. This gave 0.9 g (77% of theory) of the product as a solid.

LCMS (method 1): $R_t$=1.19 min. (m/z=327 (M+H)$^+$)

$^1$H-NMR (400 MHz, DMSO-d$_6$): δ=7.96 (d, 1H), 7.84 (d, 1H), 7.68 (dd, 1H), 7.5 (s, 1H), 7.16 (s, 1H), 5.87 (s, 2H), 4.22 (q, 2H), 3.32 (s, 2H), 1.23 (t, 3H).

Example 4A 6-(2,4-Dichlorophenyl)imidazo[1,2-a]pyrazin-8(7H)-one

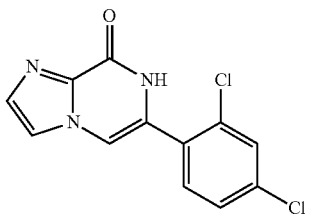 [SMILES: O=c1[nH]c(-c2ccc(Cl)cc2Cl)cn2ccnc12]

920 mg (2.8 mmol) of ethyl 1-[2-(2,4-dichlorophenyl)-2-oxoethyl]-1H-imidazol-2-carboxylate (Example 3A) were dissolved in 45 ml of glacial acetic acid, and 2.17 g (28 mmol) of ammonium acetate were added. The mixture was stirred under reflux for 12 h. The reaction mixture was added to ice-water and neutralized and with sodium carbonate. The precipitate was filtered off and dried under high vacuum. This gave 650 mg (82% of theory) of the product as a solid.

LCMS (method 3): $R_t$=1.79 min. (m/z=281 (M+H)$^+$)

$^1$H-NMR (400 MHz, DMSO-d$_6$): δ=11.5 (s, 1H), 7.83 (s, 1H) 7.81 (d, 1H), 7.63 (s, 1H), 7.61 (s, 1H), 7.58 (d, 1H), 7.52 (s, 1H).

Example 5A

8-Chloro-6-(2,4-dichlorophenyl)imidazo[1,2-a]pyrazine

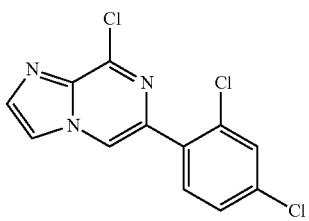 [SMILES: Clc1ccc(-c2cn3ccnc3c(Cl)n2)c(Cl)c1]

650 mg (2.3 mmol) of 6-(2,4-dichlorophenyl)imidazo[1,2-a]pyrazin-8(7H)-one (Example 4A) were dissolved in 7 ml of phosphoryl chloride and stirred under reflux for 12 h. The reaction mixture was poured into 100 ml of saturated sodium bicarbonate solution, and solid sodium bicarbonate was added until a pH of 7 had been reached. Ethyl acetate was added, and the mixture was extracted. The organic phase was washed with saturated aqueous sodium chloride solution, dried over magnesium sulfate and concentrated on a rotary evaporator. Methanol was added to the residue, and the precipitated solid was filtered off and washed with methanol and diethyl ether and dried under high vacuum. This gave 400 mg (58% of theory) of the product as a solid.

LCMS (method 3): $R_t$=2.43 min. (m/z=299 (M+H)$^+$)

$^1$H-NMR (400 MHz, DMSO-d$_6$): δ=9.01 (s, 1H), 8.34 (s, 1H) 7.93 (s, 1H), 7.81 (d, 1H), 7.72 (d, 1H), 7.6 (dd, 1H).

Example 6A

4-Amino-2-(methylsulfonyl)-1,3-thiazole-5-carbonitrile

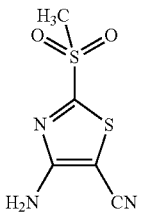

2.7 g (15.8 mmol) of 4-amino-2-(methylsulfanyl)-1,3-thiazole-5-carbonitrile were dissolved in 500 ml of dichloromethane, and 12 g (34.7 mmol) of 50% strength 3-chloroperbenzoic acid were added. The mixture was stirred at RT for 30 min. 6 ml of DMSO were added, and the reaction mixture was washed with saturated sodium bicarbonate solution and water. The organic phase was dried over magnesium sulfate and concentrated on a rotary evaporator. This gave 2.2 g (46% of theory) of the product as a solid.

LCMS (method 4): $R_t$=1.19 min. (m/z=204 (M+H)$^+$).

Example 7A tert-Butyl {2-[(4-amino-5-cyano-1,3-thiazol-2-yl)amino]ethyl}carbamate

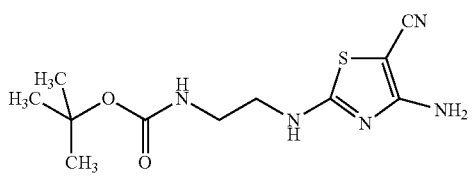 [SMILES: CC(C)(C)OC(=O)NCCNc1nc(N)c(C#N)s1]

3.25 g (16 mmol) of 4-amino-2-(methylsulfonyl)-1,3-thiazole-5-carbonitrile (Example 6A) were dissolved in 50 ml of DMSO, and 3.8 g (24 mmol) of N-Boc-ethylenediamine and 2.8 ml (16 mmol) of N,N-diisopropylethylamine were added. The mixture was stirred at 120° C. for 12 h. The reaction mixture was taken up in a mixture of ethyl acetate and water. The organic phase was washed with saturated aqueous sodium chloride solution, dried over magnesium sulfate and concentrated on a rotary evaporator. The crude product was triturated with acetonitrile and the precipitated crystals were filtered off with suction. This gave 2.5 g (55% of theory) of the product as a solid.

LCMS (method 4): $R_t$=1.81 min. (m/z=284 (M+H)$^+$).

$^1$H-NMR (400 MHz, DMSO-d$_6$): δ=8.35 (s, 1H), 6.9 (t, 1H), 6.68 (s, 2H), 3.22 (q, 2H), 3.07 (q, 2H), 1.36 (s, 9H).

Example 8A

4-Amino-2-[(2-aminoethyl)amino]-1,3-thiazol-5-carbonitrile dihydrochloride

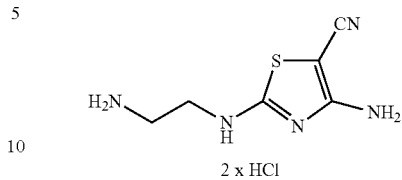

2.18 g (7.7 mmol) of tert-butyl {2-[(4-amino-5-cyano-1,3-thiazol-2-yl)amino]ethyl}carbamate (Example 7A) in 100 ml of 4N hydrogen chloride in dioxane were stirred at RT for 30 min. The reaction mixture was concentrated. This gave 2 g (100% of theory) of the product as a solid.

LCMS (method 6): $R_t$=0.19 min. (m/z=183 (M+H)$^+$).

$^1$H-NMR (400 MHz, DMSO-d$_6$): δ=3.46 (d, 2H), 3.0 (d, 2H).

Example 9A

4-Amino-2-({2-[(6-bromoimidazo[1,2-a]pyrazin-8-yl)amino]ethyl}amino)-1,3-thiazole-5-carbonitrile

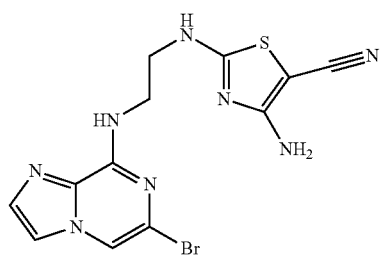 [SMILES: N#Cc1sc(NCCNc2nc(Br)cn3ccnc23)nc1N]

300 mg (1.08 mmol) of 6,8-dibromoimidazo[1,2-a]pyrazine were dissolved in 10 ml of DMSO, and 0.6 ml (4.3 mmol) of triethylamine and 360 mg (1.3 mmol) of 4-amino-2-[(2-aminoethyl)amino]-1,3-thiazole-5-carbonitrile dihydrochloride (Example 8A) were added. The mixture was heated at 140° C. in a microwave for 1 h. Purification by preparative HPLC gave 376 mg (83% of theory) of the product as a solid.

LCMS (method 8): $R_t$=0.88 min. (m/z=381 (M+H)$^+$).

$^1$H-NMR (400 MHz, DMSO-d$_6$): δ=8.46 (t, 1H), 8.12 (t, 1H), 8.05 (s, 1H), 7.85 (s, 1H), 7.53 (s, 1H), 3.6 (d, 2H), 3.48 (d, 2H).

Example 10A

Diethyl 1-[2-(2,4-dichlorophenyl)-2-oxoethyl]-1H-pyrazole-3,5-dicarboxylate

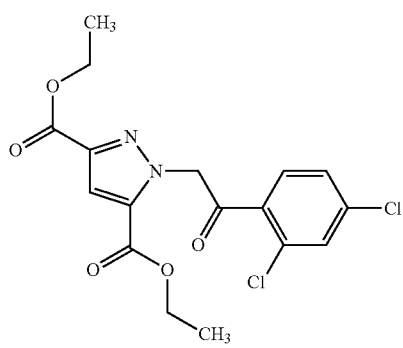 [SMILES: CCOC(=O)c1cc(C(=O)OCC)n(CC(=O)c2ccc(Cl)cc2Cl)n1]

5 g (23.6 mmol) of diethyl 1H-pyrazole-3,5-dicarboxylate were dissolved in 100 ml of acetone, and 6.3 g (23.6 mmol) of 2-bromo-2,4-dichloroacetophenone and 3.6 g (26 mmol) of potassium carbonate were added. The mixture was stirred at RT for 12 h. The reaction mixture was concentrated and the residue was taken up in water and dichloromethane. The organic phase was washed with saturated aqueous sodium chloride solution, dried over magnesium sulfate and concentrated on a rotary evaporator. The residue was triturated with diethyl ether, and the solid was filtered off with suction. This gave 9.48 g (94% of theory) of the product as a solid.

LCMS (method 6): $R_t$=2.34 min. (m/z=399 (M+H)$^+$)

$^1$H-NMR (400 MHz, DMSO-d$_6$): δ=8.02 (d, 1H), 7.84 (s, 1H), 7.68 (dd, 1H), 7.35 (s, 1H), 6.13 (s, 2H), 4.32 (q, 2H), 4.26 (q, 2H), 1.31 (t, 3H), 1.25 (t, 3H).

Example 11A

Ethyl 6-(2,4-dichlorophenyl)-4-oxo-4,5-dihydropyrazolo[1,5-a]pyrazine-2-carboxylate

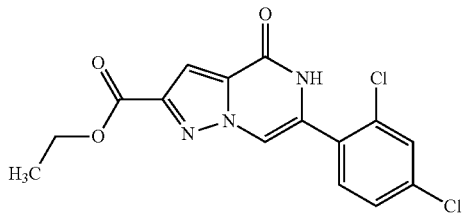 [SMILES: CCOC(=O)c1cc2c(=O)[nH]c(-c3ccc(Cl)cc3Cl)cn2n1]

9.5 g (23.7 mmol) of diethyl 1-[2-(2,4-dichlorophenyl)-2-oxoethyl]-1H-pyrazole-3,5-dicarboxylate (Example 10A) were dissolved in 300 ml of glacial acetic acid, and 18.3 g (237 mmol) of ammonium acetate were added. The mixture was stirred at reflux for 12 h. The reaction mixture was poured into ice-water and neutralized with sodium carbonate. The precipitate was filtered off and dried under high vacuum. This gave 6.86 g (82% of theory) of the product as a solid.

LCMS (method 3): $R_t$=2.31 min (m/z=354 (M+H)$^+$)

$^1$H-NMR (400 MHz, DMSO-d$_6$): δ=11.85 (s, 1H), 7.98 (s, 1H) 7.83 (d, 1H), 7.64 (d, 1H), 7.59 (dd, 1H), 7.44 (s, 1H), 4.34 (q, 2H), 1.33 (t, 3H).

Example 12A

Ethyl 4-chloro-6-(2,4-dichlorophenyl)pyrazolo[1,5-a]pyrazine-2-carboxylate

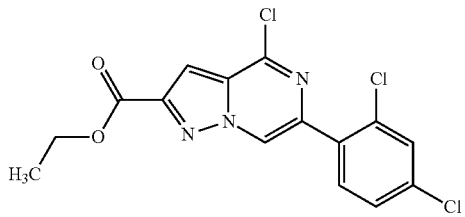 [SMILES: CCOC(=O)c1cc2c(Cl)nc(-c3ccc(Cl)cc3Cl)cn2n1]

6.86 g (19.5 mmol) of ethyl 6-(2,4-dichlorophenyl)-4-oxo-4,5-dihydropyrazolo[1,5-a]pyrazine-2-carboxylate (Example 11A) were dissolved in 50 ml of phosphoryl chloride and stirred at reflux for 12 h. The reaction mixture was poured into 1.25 l of saturated sodium bicarbonate solution, and solid sodium bicarbonate was added until a pH of 7 had been reached. The solid was filtered off and dissolved in dichloromethane and chromatographed on silica gel (mobile phase cyclohexane/ethyl acetate 10:1). This gave 6.34 g (85% of theory) of the product as a solid.

LCMS (method 3): $R_t$=3.15 min. (m/z=371 (M+H)$^+$).

$^1$H-NMR (400 MHz, DMSO-d$_6$): δ=9.3 (s, 1H), 7.84 (d, 1H) 7.73 (d, 1H), 7.62 (dd, 1H), 7.56 (s, 1H), 4.4 (q, 2H), 1.36 (t, 3H).

Example 13A

Ethyl 3-acetamido-2-oxobutanoate

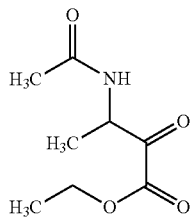

52 g (396 mmol) of acetylalanine were dissolved in 800 ml of THF, and 45 mg (0.4 mmol) of 4-dimethylaminopyridine and 96 ml (1188 mmol) of pyridine were added. The mixture was heated to reflux, and 88 ml (792 mmol) of ethyl oxalyl chloride were added dropwise over a period of 45 min. The mixture was stirred at reflux for a further 3 h. The reaction mixture was added to ice-water, ethyl acetate was added and the mixture was extracted. The organic phase was washed with saturated aqueous sodium chloride solution, dried over sodium sulfate and concentrated on a rotary evaporator. The crude mixture was reacted further without any further purification.

$^1$H-NMR (400 MHz, CDCl$_3$): δ=10.86 (s, 1H), 4.42 (q, 1H) 4.23 (q, 2H), 2.16 (s, 3H), 1.42 (t, 3H), 1.29 (t, 3H).

Example 14A

N-[1-(5-Oxo-3-phenyl-4,5-dihydro-1,2,4-triazin-6-yl)ethyl]acetamide

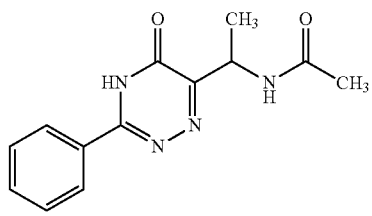 [SMILES: CC(=O)NC(C)c1nnc(-c2ccccc2)[nH]c1=O]

48 g (306 mmol) of benzenecarboximidamide hydrochloride were dissolved in 1.2 l ethanol, and 16.4 ml (337 mmol) of hydrazine hydrate were added. The mixture was stirred at 45° C. for 3 h. 86 g (459 mmol) of ethyl 3-acetamido-2-oxobutanoate (Example 13A), dissolved in 600 ml of ethanol, were added dropwise. The mixture was stirred at 80° C. for another 6 h and at RT for another 12 h. The reaction mixture was chromatographed on silica gel (mobile phase dichloromethane/methanol 20:1). This gave 23.2 g (26% of theory) of the product as a solid.

$^1$H-NMR (400 MHz, CDCl$_3$): δ=8.21 (d, 2H), 7.56 (m, 3H) 5.36 (q, 1H), 2.05 (s, 3H), 1.55 (d, 3H).

Example 15A 5,7-Dimethyl-2-phenylimidazo[5,1-f][1,2,4]triazin-4(3H)-one

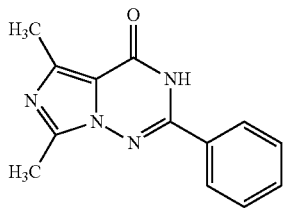 [SMILES: Cc1nc(C)n2nc(-c3ccccc3)[nH]c(=O)c12]

8.34 g (32.3 mmol) of N-[1-(5-oxo-3-phenyl-4,5-dihydro-1,2,4-triazin-6-yl)ethyl]acetamide] (Example 14A) were dissolved in 330 ml of 1,2-dichloroethane and 4.5 ml (48.5 mmol) of phosphoryl chloride were added. The mixture was stirred under reflux for 24 h. After cooling, the precipitate was filtered off and washed with water and diethyl ether. The product was subsequently dried under high vacuum. This gave 4.6 g (59% of theory) of the product as a solid.

$^1$H-NMR (400 MHz, DMSO-d$_6$): δ=12.45 (s, 1H), 8.08 (d, 2H), 7.6 (m, 3H), 2.69 (s, 3H), 2.59 (s, 3H).

Example 16A

4-Chloro-5,7-dimethyl-2-phenylimidazo[5,1-f][1,2,4]triazine

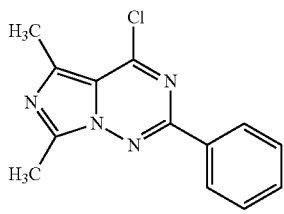 [SMILES: Cc1nc(C)n2nc(-c3ccccc3)nc(Cl)c12]

700 mg (2.9 mmol) of 5,7-dimethyl-2-phenylimidazo[5,1-f][1,2,4]triazin-4(3H)-one (Example 15A) were dissolved in 8 ml of phosphoryl chloride and stirred at reflux for 12 h. The reaction mixture was poured into 170 ml of saturated sodium bicarbonate solution, and solid sodium bicarbonate was added until a pH of 7 had been reached. Ethyl acetate was added, and the mixture was extracted. The organic phase was washed with saturated aqueous sodium chloride solution, dried over magnesium sulfate and concentrated on a rotary evaporator. This gave 657 mg (80% of theory) of the product as a solid.

LCMS (method 6): R$_t$=2.17 min. (m/z=259 (M+H)$^+$).

$^1$H-NMR (400 MHz, DMSO-d$_6$): δ=8.26 (dd, 2H), 7.58 (m, 3H), 2.68 (s, 3H), 2.66 (s, 3H).

Example 17A 6-(2,4-Dichlorophenyl)-2-(hydroxymethyl)pyrazolo[1,5-a]pyrazin-4(5H)-one

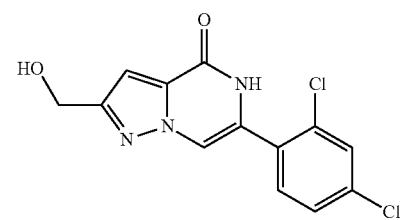 [SMILES: O=c1[nH]c(-c2ccc(Cl)cc2Cl)cn2nc(CO)cc12]

5 g (12.55 mmol) of ethyl 6-(2,4-dichlorophenyl)-4-oxo-4,5-dihydropyrazolo[1,5-a]pyrazine-2-carboxylate (Example 11A) were dissolved in 700 ml of THF, and 952 mg (25.1 mmol) of lithium aluminum hydride were added at RT. The mixture was stirred at RT for 2 h, after complete conversion methanol was added first, and the pH was then adjusted to 6 using dilute hydrochloric acid. The mixture was extracted repeatedly with ethyl acetate. Removal of the solvent gave 3.12 g (80% of theory) of the product as a solid.

LCMS (method 3): R$_t$=1.66 min. (m/z=310 (M+H)$^+$).

$^1$H-NMR (400 MHz, DMSO-d$_6$): δ=11.55 (s, 1H), 7.81 (d, 1H), 7.77 (s, 1H), 7.62 (d, 1H), 7.66 (dd, 1H), 6.94 (s, 1H), 5.32 (t, 1H), 4.58 (d, 2H).

Example 18A 6-(2,4-Dichlorophenyl)-4-oxo-4,5-dihydropyrazolo[1,5-a]pyrazine-2-carbaldehyde

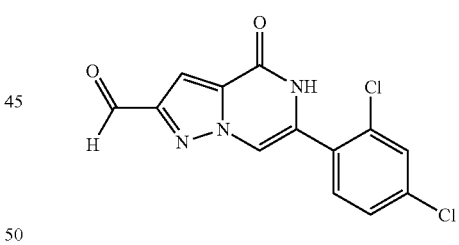

1.15 g (3.37 mmol) of 6-(2,4-dichlorophenyl)-2-(hydroxymethyl)pyrazolo[1,5-a]pyrazin-4(5H)-one (Example 17A) were suspended in 100 ml of dichloromethane, and 1 drop of water was added. 100 ml of 1,2-dimethoxyethane and 9.6 ml of DMF were then added, and the mixture was cooled to 0° C. 7.16 g (16.87 mmol) of Dess-Martin periodinane were added, ice-bath cooling was removed and the mixture was stirred at RT for 15 h. Ethyl acetate and then 200 ml of a 10% strength sodium thiosulfate solution were added to the mixture, and the organic phase was washed with saturated aqueous sodium bicarbonate solution. Drying of the organic phase with sodium sulfate and removal of the solvent under reduced pressure gave 660 mg (57% of theory) of the product as a solid which was reacted without any further purification.

LCMS (method 8): R$_t$=1.04 min. (m/z=308 (M+H)$^+$).

¹H-NMR (400 MHz, DMSO-d₆): δ=11.89 (s, 1H), 10.07 (s, 1H), 8.02 (s, 1H), 7.84 (d, 1H), 7.66 (d, 1H), 7.60 (dd, 1H), 7.52 (s, 1H).

Example 19A 6-(2,4-Dichlorophenyl)-2-[(4-methylpiperazin-1-yl)methyl]pyrazolo[1,5-a]pyrazin-4(5H)-one

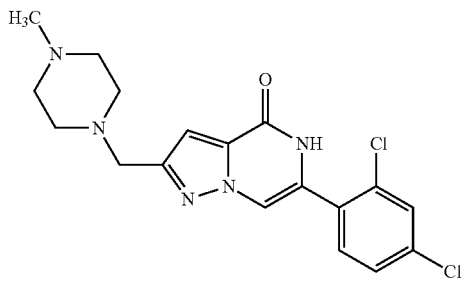 [SMILES: CN1CCN(Cc2cc3c(=O)[nH]c(-c4ccc(Cl)cc4Cl)cn3n2)CC1]

145 mg (0.32 mmol) of 6-(2,4-dichlorophenyl)-4-oxo-4,5-dihydropyrazolo[1,5-a]pyrazine-2-carb-aldehyde (Example 18A) were dissolved in 6 ml of methanol, and 64 mg (0.64 mmol) of 1-methylpiperazine, 4 Å molecular sieve and 58 mg (0.96 mmol) of acetic acid were added. Finally, 40.2 mg (0.64 mmol) of sodium cyanoborohydride were added and the mixture was stirred at RT for 15 h. The crude mixture was acidified with 2N hydrochloric acid and the resulting precipitate was filtered off with suction. This gave 120 mg (96% of theory) of the product as a solid which was reacted further without any further purification.

LCMS (method 6): $R_t$=0.76 min. (m/z=392 (M+H)⁺).

¹H-NMR (400 MHz, DMSO-d₆): δ=11.63 (s, 1H), 7.82 (d, 1H), 7.81 (s, 1H), 7.61 (d, 1H), 7.57 (dd, 1H), 7.0 (s, 1H), 3.7-4.0 (m, 4H), 3.38 (m, 2H), 3.04 (m, 4H), 2.78 (s, 3H).

Example 20A

4-Chloro-6-(2,4-dichlorophenyl)-2-[(4-methylpiperazin-1-yl)methyl]pyrazolo[1,5-a]pyrazine

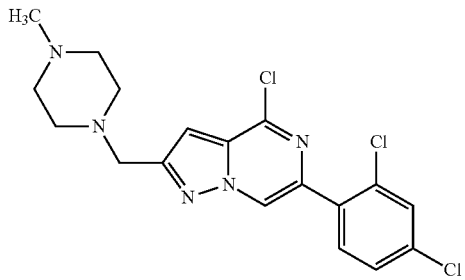 [SMILES: CN1CCN(Cc2cc3c(Cl)nc(-c4ccc(Cl)cc4Cl)cn3n2)CC1]

Analogously to the preparation of Example 16A, 160 mg (0.34 mmol) of 6-(2,4-dichlorophenyl)-2-[(4-methylpiperazin-1-yl)methyl]pyrazolo[1,5-a]pyrazin-4(5H)-one gave, by reaction with phosphoryl chloride, 108 mg (70% of theory) of the product as a solid.

LCMS (method 6): $R_t$=0.76 min. (m/z=392 (M+H)⁺).

¹H-NMR (400 MHz, DMSO-d₆): δ=9.12 (s, 1H), 7.81 (d, 1H), 7.71 (d, 1H), 7.60 (dd, 1H), 6.99 (s, 1H), 3.74 (s, 2H), 2.4-2.55 (m, 4H), 2.25-2.4 (m, 4H), 2.15 (s, 3H).

Example 21A 6-(2,4-Dichlorophenyl)-2-(morpholin-4-ylmethyl)pyrazolo[1,5-a]pyrazin-4(5H)-one trifluoroacetate

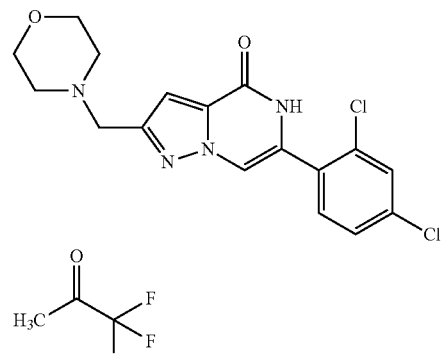

760 mg (2.17 mmol) of 6-(2,4-dichlorophenyl)-4-oxo-4,5-dihydropyrazolo[1,5-a]pyrazine-2-carb-aldehyde (Example 18A) were dissolved in 46 ml of methanol, and 378 mg (4.34 mmol) of morpholine, 4 Å molecular sieve and 0.373 ml (6.51 mmol) of acetic acid were added. Finally, 272.8 mg (4.34 mmol) of sodium cyanoborohydride were added and the mixture was stirred at RT for 15 h. The crude mixture was acidified with 2N hydrochloric acid and the resulting precipitate was filtered off with suction. Purification of the precipitate by preparative HPLC (mobile phase: acetonitrile/water gradient with 0.1% trifluoroacetic acid) gave 693 mg (65% of theory) of the product as a solid.

LCMS (method 8): $R_t$=0.75 min. (m/z=379 (M+H)⁺).

¹H-NMR (400 MHz, DMSO-d₆): δ=11.79 (s, 1H), 10.31 (s, br, 1H), 7.91 (s, 1H), 7.84 (d, 1H), 7.64 (d, 1H), 7.59 (dd, 1H), 7.22 (s, 1H), 4.54 (s, 2H), 3.96 (m, 2H), 3.64 (m, 2H), 3.39 (m, 2H), 3.18 (m, 2H).

Example 22A

4-Chloro-6-(2,4-dichlorophenyl)-2-(morpholin-4-ylmethyl)pyrazolo[1,5-a]pyrazine hydrochloride

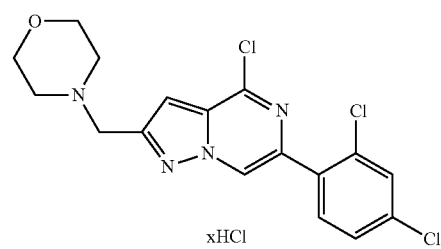 [SMILES: Clc1ccc(-c2cn3nc(CN4CCOCC4)cc3c(Cl)n2)c(Cl)c1 ; "xHCl"]

Analogously to the preparation of Example 16A, 690 mg (1.18 mmol) of 6-(2,4-dichlorophenyl)-2-(morpholin-4-ylmethyl)pyrazolo[1,5-a]pyrazin-4(5H)-one trifluoroacetate gave, by reaction with phosphoryl chloride, 395 mg (85% of theory) of the product as a solid.

LCMS (method 6): $R_t$=1.32 min. (m/z=397 (M+H)$^+$).

$^1$H-NMR (400 MHz, DMSO-$d_6$): δ=11.50 (s, 1H), 9.23 (s, 1H), 7.84 (d, 1H), 7.72 (d, 1H), 7.62 (dd, 1H), 7.44 (s, br, 1H), 4.65 (s, br, 2H), 3.9-4.0 (m, 2H), 3.7-3.85 (m, 2H), 3.3-3.45 (m, 2H), 3.1-3.25 (m, 2H).

Example 23A 6-({2-[(6-Bromoimidazo[1,2-a]pyrazin-8-yl)amino]ethyl}amino)pyridine-3-carbonitrile

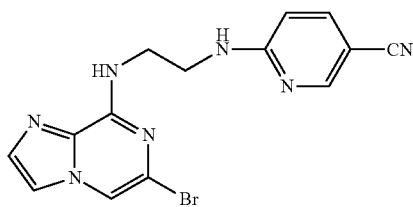 [SMILES: N#Cc1ccc(NCCNc2nc(Br)cn3ccnc23)nc1]

8 g (28.9 mmol) of 6,8-dibromoimidazo[1,2-a]pyrazine were dissolved in 80 ml of DMSO, and 16.1 ml (115.6 mmol) of triethylamine and 5.154 g (31.78 mmol) of 6-[(2-aminoethyl)amino]pyridine-3-carbonitrile (Example 2A) were added. The mixture was heated at 140° C. in a microwave for 1.5 h. The solution was poured into water and the precipitate was filtered off. Washing with water and drying under high vacuum gave 10.3 g (94% of theory) of the product as a solid.

LCMS (method 8): $R_t$=0.97 min. (m/z=358 (M+H)$^+$).

$^1$H-NMR (400 MHz, DMSO-$d_6$): δ=8.39 (s, 1H), 8.08 (s, br, 1H), 8.03 (s, 1H), 7.83 (s, 1H), 7.73 (m, 2H), 7.51 (s, 1H), 6.56 (s, br, 1H), 3.5-3.65 (m, 4H).

Example 24A tert-Butyl (6-chloropyridin-2-yl)carbamate

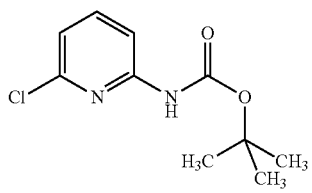

Under argon, 150 ml of THF were added to 23.4 g (181.8 mmol) of 2-chloro-5-aminopyridine and the mixture was cooled to 0° C. 73.3 g (400 mmol) of bis(trimethylsilyl)sodium amide and 43.65 g (200 mmol) of di-tert-butyl dicarbonate, dissolved in 150 ml of THF, were added dropwise. After 15 min, the cooling bath was removed and the mixture was stirred for a further 15 min at RT. The THF was removed using a rotary evaporator, ethyl acetate and 0.5 N hydrochloric acid were added and the mixture was extracted. The organic phase was separated off, dried over magnesium sulfate and concentrated on a rotary evaporator. The reaction mixture was chromatographed on silica gel (mobile phase dichloromethane/methanol 100%→100:3). This gave 36.54 g (88% of theory) of the product as a solid.

LCMS (method 3): $R_t$=2.41 min. (m/z=175 (M+H)$^+$).

$^1$H-NMR (400 MHz, DMSO-$d_6$): δ=10.11 (s, 1H), 7.78 (d, 2H), 7.1 (t, 1H), 1.47 (s, 9H).

Example 25A tert-Butyl (6-chloro-3-formylpyridin-2-yl)carbamate

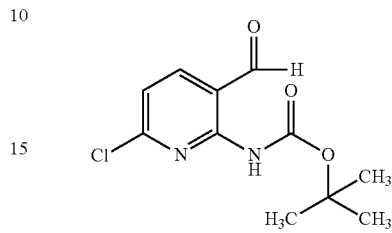

The reaction apparatus was dried by heating, and the reaction was carried out under argon with stirring. 15 g (65.6 mmol) of tert-butyl (6-chloropyridin-2-yl)carbamate (Example 24A) and 19 g (164 mmol) of 1,2-bis(dimethylamino)ethane were initially charged in 270 ml of THF and cooled to −78° C. 102.5 ml (164 mmol) of butyllithium (1.6N) were added dropwise. After the dropwise addition had ended, the reaction was slowly warmed to −10° C. and kept at −10° C. for 2 h. The mixture was then once more cooled to −78° C., and 10 ml (131 mmol) of DMF were added. The reaction was slowly warmed to RT, the reaction mixture was added to 1 l of ethyl acetate and 350 ml of 1N hydrochloric acid and stirred for 15 min and the organic phase was separated off. The organic phase was washed with water and saturated sodium bicarbonate solution, dried over magnesium sulfate and concentrated on a rotary evaporator. Diethyl ether was added to the residue, and the solid was filtered off with suction and dried. This gave 12.3 g (73% of theory) of the product as a solid.

LCMS (method 3): $R_t$=2.19 min. (m/z=255 (M+H)$^-$).

$^1$H-NMR (400 MHz, DMSO-$d_6$): δ=10.37 (s, 1H), 9.83 (s, 1H), 8.2 (d, 1H), 7.42 (d, 1H), 1.46 (s, 9H).

Example 26A tert-Butyl {6-chloro-3-[(hydroxyimino)methyl]pyridin-2-yl}carbamate

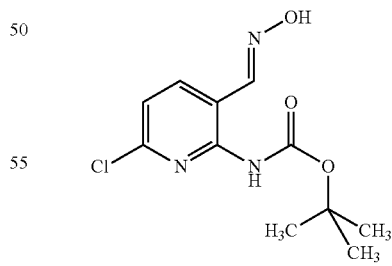

15.45 g (60.2 mmol) of tert-butyl (6-chloro-3-formylpyridin-2-yl)carbamate (Example 25A) were initially charged in 750 ml of ethanol, a solution of 225 ml of water and 9.38 g (120.4 mmol) of sodium acetate was added and the mixture was stirred for 5 min. A solution of 225 ml of water and 8.36 g (114.4 mmol) of hydroxylamine hydrochloride was added and the mixture was stirred at RT for 4 h. The reaction mixture was concentrated on a rotary evaporator at 20° C. The residue was taken up in ethyl acetate, washed twice with saturated sodium bicarbonate solution and once with saturated sodium chloride solution. The organic phase was separated off, dried over magnesium sulfate and concentrated on a rotary evaporator at 20° C. This gave 15.5 g (80% of theory) of the product as a solid.

LCMS (method 3): $R_t$=2.08 min. (m/z=270 (M+H)$^-$).

$^1$H-NMR (400 MHz, DMSO-d$_6$): δ=11.71 (s, 1H), 9.91 (s, 1H), 8.14 (s, 1H), 8.02 (d, 1H), 7.3 (d, 1H), 1.49 (s, 9H).

Example 27A

2-Amino-6-chloropyridine-3-carbaldehyde oxime hydrochloride

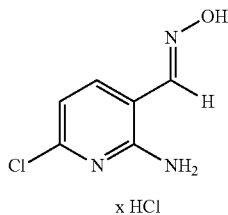 [SMILES: Nc1nc(Cl)ccc1/C=N/O]

15.5 g (57 mmol) of tert-butyl {6-chloro-3-[(hydroxyimino)methyl]pyridin-2-yl}carbamate (Example 26A) were dissolved in 285 ml of 4N hydrogen chloride in dioxane and the mixture was stirred for 30 min. The reaction mixture was concentrated to half of its original volume and the same amount of diethyl ether was added. The reaction mixture was stirred for 20 min and the product was filtered off and washed with diethyl ether. This gave 11 g (94% of theory) of the product as a solid.

LCMS (method 6): $R_t$=1.09 min. (m/z=172 (M+H)$^+$)

$^1$H-NMR (400 MHz, DMSO-d$_6$): δ=8.27 (s, 1H), 7.61 (d, 1H), 6.65 (d, 1H).

Example 28A

2-Amino-6-chloropyridine-3-carbonitrile

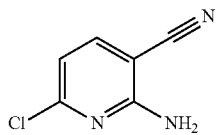

11.15 g (53.6 mmol) of 2-amino-6-chloropyridine-3-carbaldehyde oxime hydrochloride (Example 27A) were initially charged in dioxane, 13 ml (161 mmol) of pyridine were added and the mixture was cooled to 0° C. 8.3 ml (58.95 mmol) of trifluoroacetic anhydride were added, and the reaction was warmed to RT and then stirred at 60° C. for 2 h. The reaction mixture was taken up in a mixture of ethyl acetate and sodium bicarbonate solution. The organic phase was washed with saturated aqueous sodium chloride solution, dried over magnesium sulfate and concentrated on a rotary evaporator. The residue was suspended in dichloromethane: diethyl ether 3:1, and the solid was filtered off with suction and dried. This gave 5.56 g (66% of theory) of the product as a solid.

LCMS (method 6): $R_t$=1.0 min. (m/z=154 (M+H)$^+$).

$^1$H-NMR (400 MHz, DMSO-d$_6$): δ=7.91 (d, 1H), 7.38 (s, 2H), 6.69 (d, 1H).

Example 29A tert-Butyl {2-[(6-amino-5-cyanopyridin-2-yl)amino]ethyl}carbamate

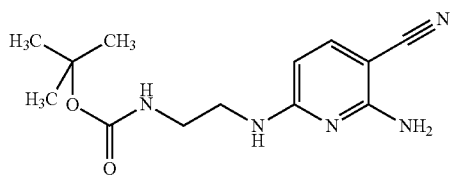 [SMILES: CC(C)(C)OC(=O)NCCNc1ccc(C#N)c(N)n1]

2 g (13 mmol) of 2-amino-6-chloropyridine-3-carbonitrile (Example 28A) were initially charged in 15 ml of DMSO, and 2.71 g (16.93 mmol) of N-Boc-ethyleneamine and 3.4 ml (19.54 mmol) of N,N-diisopropylethylamine were added. The reaction mixture was irradiated in a microwave reactor at 115° C. for 1.5 h. The reaction mixture was taken up in a mixture of ethyl acetate and water. The organic phase was washed with saturated aqueous sodium chloride solution, dried over magnesium sulfate and concentrated on a rotary evaporator. This gave 23.38 g (88% of theory) of the product as a solid.

LCMS (method 3): $R_t$=1.7 min. (m/z=278 (M+H)$^+$).

$^1$H-NMR (400 MHz, DMSO-d$_6$): δ=7.3 (s, 1H), 7.0 (br, s, 1H), 6.83 (s, 1H), 6.25 (s, 2H), 5.78 (d, 1H), 3.25 (q, 2H), 3.06 (q, 2H), 1.36 (s, 9H).

Example 30A

2-Amino-6-[(2-aminoethyl)amino]pyridine-3-carbonitrile dihydrochloride

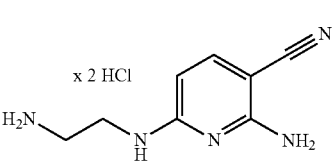 [SMILES: N#Cc1ccc(NCCN)nc1N]

6.76 g (24.38 mmol) of tert-butyl {2-[(6-amino-5-cyanopyridin-2-yl)amino]ethyl}carbamate (Example 29A) were dissolved in 122 ml of a 4N solution of hydrogen chloride in dioxane and the mixture was stirred for 30 min. The reaction mixture was concentrated to half of its original volume and the same amount of diethyl ether was added. The reaction mixture was stirred for 20 min and the product was filtered off and washed with diethyl ether. This gave 5.43 g (89% of theory) of the product as a solid.

LCMS (method 6): $R_t$=0.92 min. (m/z=177 (M+H)$^+$)
$^1$H-NMR (400 MHz, DMSO-d$_6$): δ=8.1 (s, 2H), 7.5 (d, 1H), 5.96 (d, 1H), 3.53 (q, 2H), 3.0 (q, 2H).

Example 31A 4-(Trifluoroacetyl)morpholine

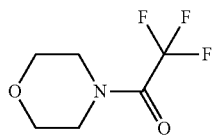 [SMILES: O=C(N1CCOCC1)C(F)(F)F]

15 g (172 mmol) of morpholine were initially charged in 750 ml of dichloromethane, and 29 ml (206 mmol) of trifluoroacetic anhydride and 119 ml (688 mmol) of N,N-diisopropylethylamine were added at 0° C. The reaction mixture was warmed to RT and stirred at RT for another 3 h. The reaction mixture was concentrated and the residue was taken up in ethyl acetate and washed successively with aqueous sodium bicarbonate solution, 1N hydrochloric acid and once more with aqueous sodium bicarbonate solution. The organic phase was dried over magnesium sulfate and concentrated on a rotary evaporator. This gave 28 g (88% of theory) of the product as an oil.

LCMS (method 9): $R_t$=1.22 min. (m/z=184 (M+H)$^+$)
$^1$H-NMR (400 MHz, DMSO-d$_6$): δ=3.65 (m, 2H), 3.56 (m, 2H).

Example 32A tert-Butyl [6-chloro-3-(trifluoroacetyl)pyridin-2-yl]carbamate

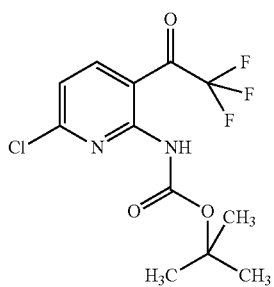 [SMILES: CC(C)(C)OC(=O)Nc1nc(Cl)ccc1C(=O)C(F)(F)F]

8 g (35 mmol) of tert-butyl (6-chloropyridin-2-yl)carbamate (Example 24A) were initially charged in 100 ml of THF and cooled to −50° C. 55 ml (87 mmol) of butyllithium (1.6N) were added dropwise. After the dropwise addition had ended, the reaction was slowly warmed to −10° C. and stirred at 0° C. for 2 h. The mixture was then cooled again to −40° C., and 12.8 g (70 mmol) of 4-(trifluoroacetyl)morpholine (Example 21A), dissolved in 4 ml of THF, were added. The reaction solution was stirred at −40° C. for 1 h, and, at −40° C., poured into 1 l of ethyl acetate and 350 ml of ammonium chloride solution and extracted. The organic phase was separated off, dried over magnesium sulfate and concentrated on a rotary evaporator. The reaction mixture was chromatographed on silica gel (mobile phase cyclohexane/ethyl acetate 10:1). This gave 9 g (79% of theory) of the product as an oil.

$^1$H-NMR (400 MHz, DMSO-d$_6$): δ=10.96 (s, 1H), 7.99 (d, 1H), 7.4 (d, 1H), 1.43 (s, 9H).

Example 33A tert-Butyl [6-({2-[(tert-butoxycarbonyl)amino]ethyl}amino)-3-(trifluoroacetyl)pyridin-2-yl]carbamate

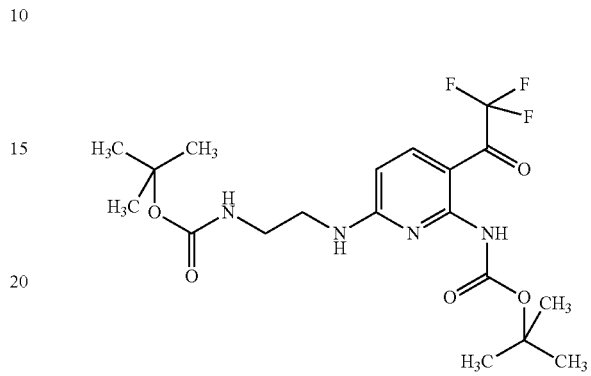

5 g (15.4 mmol) of tert-butyl [6-chloro-3-(trifluoroacetyl)pyridin-2-yl]carbamate (Example 32A) were initially charged in 37.5 ml of DMSO, and 3.2 g (20 mmol) of N-Boc-ethylenediamine and 4 ml (23 mmol) of N,N-diisopropylethylamine were added. The reaction mixture was irradiated in a microwave reactor at 90° C. for 0.5 h. The reaction mixture was taken up in a mixture of ethyl acetate and water. The organic phase was washed with saturated aqueous sodium chloride solution, dried over magnesium sulfate and concentrated on a rotary evaporator. The reaction mixture was chromatographed on silica gel (mobile phase cyclohexane/ethyl acetate 5:1→1:1). This gave 2.5 g (34% of theory) of the product as a solid.

LCMS (method 6): $R_t$=2.44 min. (m/z=449 (M+H)$^+$).
$^1$H-NMR (400 MHz, DMSO-d$_6$): δ=10.75 (s, 1H), 8.44 (s, 1H), 7.70 (d, 1H), 6.77 (s, 1H), 6.28 (d, 1H), 3.48 (br, s, 2H), 3.17 (br, s, 2H), 1.46 (s, 9H), 1.30 (s, 9H).

Example 34A

1-{2-Amino-6-[(2-aminoethyl)amino]pyridin-3-yl}-2,2,2-trifluoroethanone hydrochloride

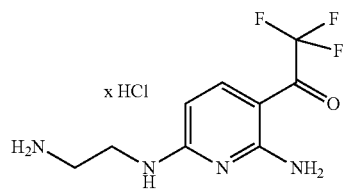 [SMILES: NCCNc1ccc(C(=O)C(F)(F)F)c(N)n1]

2.5 g (5.57 mmol) of tert-butyl [6-({2-[(tert-butoxycarbonyl)amino]ethyl}amino)-3-(trifluoroacetyl)-pyridin-2-yl]carbamate (Example 33A) were dissolved in 15 ml of a 4N solution of hydrogen chloride in dioxane, and the mixture was stirred for 20 h. The reaction mixture was concentrated to half of its original volume and the same amount of diethyl ether was added. The reaction mixture was stirred for 20 min and the product was filtered off and washed with diethyl ether. This gave 1.4 g (89% of theory) of the product as a solid.

LCMS (method 6): R$_t$=0.73 min. (m/z=249 (M+H)$^+$).

Example 35A tert-Butyl 3-[(5-cyanopyridin-2-yl)amino]piperidine-1-carboxylate

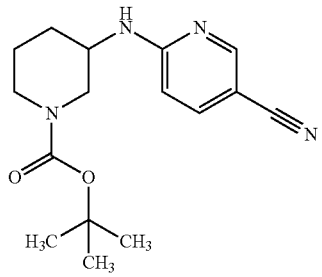 [SMILES: CC(C)(C)OC(=O)N1CCCC(Nc2ccc(C#N)cn2)C1]

1.0 g (4.99 mmol) of tert-butyl 3-aminopiperidine-1-carboxylate and 1.383 g (9.99 mmol) of 6-chloropyridine-3-carbonitrile and 1.29 g (9.99 mmol) of diisopropylethylamine were suspended in 40 ml of DMSO and heated in a microwave at 140° C. for 45 min. Most of the DMSO was removed from the mixture by kugelrohr distillation, water was added and the resulting precipitate was filtered off. Drying under high vacuum gave 2.24 g (46% of theory) of the product.

LCMS (method 3): R$_t$=2.23 min. (m/z=303 (M+H)$^+$).

Example 36A 6-(Piperidin-3-ylamino)pyridine-3-carbonitrile hydrochloride

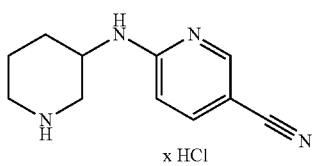 [SMILES: N#Cc1ccc(NC2CCCNC2)nc1]

2.24 g (3.4 mmol) of tert-butyl 3-[(5-cyanopyridin-2-yl)amino]piperidine-1-carboxylate (Example 35A) were dissolved in 4.3 ml of a solution of hydrochloric acid in dioxane (4 M), and the mixture was stirred at RT for 3 h. After the reaction had gone to completion, the solvent was removed completely. This gave 1.74 g (90% of theory) of the product as a solid.

LCMS (method 8): R$_t$=0.27 min. (m/z=203 (M+H)$^+$)

$^1$H-NMR (400 MHz, DMSO-d$_6$): δ=9.13 (m, 1H), 9.0 (m, 1H), 8.44 (d, 1H), 7.89 (m, 1H), 7.74 (dd, 1H), 6.63 (d, 1H), 5.58 (s, br), 4.19 (s, br, 1H), 3.57 (s, 1H), 3.34 (d, 1H), 3.14 (d, 1H), 2.88 (m, 1H), 2.7-2.81 (m, 1H), 1.82-2.0 (m, 2H), 1.63-1.79 (m, 1H), 1.48-1.59 (m, 1H).

Example 37A tert-Butyl 3-[(6-amino-5-cyanopyridin-2-yl)amino]piperidine-1-carboxylate

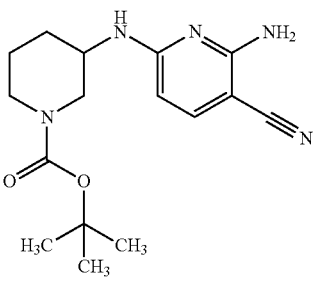 [SMILES: CC(C)(C)OC(=O)N1CCCC(Nc2ccc(C#N)c(N)n2)C1]

2.15 g (10.7 mmol) of tert-butyl 3-aminopiperidine-1-carboxylate, 1.50 g (9.77 mmol) of 2-amino-6-chloropyridine-3-carbonitrile (Example 28A) and 1.89 g (14.7 mmol) of diisopropylethylamine were suspended in 6 ml of DMSO and heated in a microwave reactor at 130° C. for 8 h. The reaction mixture was diluted with ethyl acetate (100 ml) and water (40 ml), and the organic phase was separated off and washed with saturated aqueous sodium chloride solution (50 ml), dried over magnesium sulfate and concentrated. The residue was chromatographed on silica gel (mobile phase: cyclohexane/ethyl acetate 4:1 to 1:1). This gave 2.04 g (60% of theory) of the product as a solid.

LCMS (method 6): R$_t$=1.69 min. (m/z=318 (M+H)$^+$)

Example 38A

2-Amino-6-(piperidin-3-ylamino)pyridine-3-carbonitrile hydrochloride

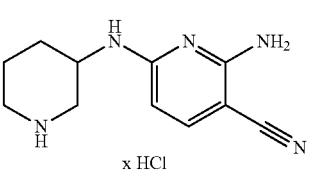 [SMILES: N#Cc1ccc(NC2CCCNC2)nc1N ; "x HCl"]

2.00 g (6.3 mmol) of tert-butyl 3-[(6-amino-5-cyanopyridin-2-yl)amino]piperidine-1-carboxylate (Example 37A) were dissolved in 40 ml of a solution of hydrochloric acid in dioxane (4 M), and the mixture was stirred at RT for 2 h. After the reaction had gone to completion the solvent was concentrated to half of its original volume and 20 ml of diethyl ether were added. The precipitate was filtered off and dried. This gave 1.80 g (100% of theory) of the product as a solid.

LCMS (method 8): R$_t$=0.25 min. (m/z=218 (M+H)$^+$)

$^1$H-NMR (400 MHz, DMSO-d$_6$): δ=9.38 (br m, 1H), 8.97 (br m, 1H), 8.25 (br m, 1H), 7.53 (m, 1H), 7.40 (br s, 2H), 6.01 (d, 1H), 4.16 (br m, 1H), 3.34 (br m, 1H), 3.10 (m, 1H), 2.89 (m, 2H), 2.00-1.84 (m, 2H), 1.73 (m, 1H), 1.55 (m, 1H).

Example 39A tert-Butyl 3-({6-[(tert-butoxycarbonyl)amino]-5-(trifluoroacetyl)pyridin-2-yl}amino)piperidine-1-carboxylate

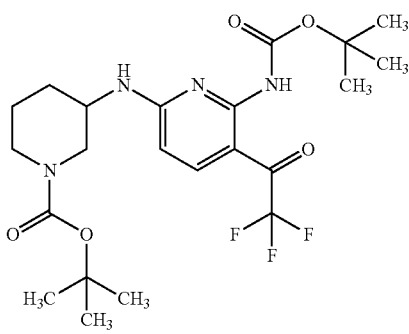 [SMILES: CC(C)(C)OC(=O)Nc1nc(NC2CCCN(C(=O)OC(C)(C)C)C2)ccc1C(=O)C(F)(F)F]

561 mg (2.8 mmol) of tert-butyl 3-aminopiperidine-1-carboxylate, 700 mg (2.16 mmol) of tert-butyl [6-chloro-3-(trifluoroacetyl)pyridin-2-yl]carbamate (Example 32A) and 0.56 ml (3.23 mmol) of diisopropylethylamine were suspended in 14 ml of DMSO and heated in a microwave reactor at 90° C. for 45 min. The reaction mixture was diluted with ethyl acetate (100 ml) and washed with saturated aqueous ammonium chloride solution (three times 40 ml) and then saturated aqueous sodium bicarbonate solution (40 ml). The organic phase was dried over magnesium sulfate and concentrated. The residue was chromatographed on silica gel (mobile phase: cyclohexane/ethyl acetate 5:1 to 1:1). This gave 670 mg (63% of theory) of the product.

LCMS (method 6): $R_t$=2.70 min. (m/z=489 (M+H)$^+$)

Example 40A

1-[2-Amino-6-(piperidin-3-ylamino)pyridin-3-yl]-2,2,2-trifluoroethanone hydrochloride

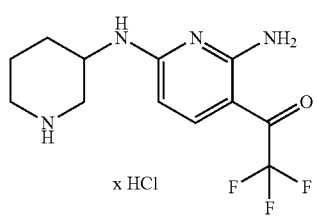 [SMILES: Nc1nc(NC2CCCNC2)ccc1C(=O)C(F)(F)F ; "x HCl"]

670 mg (1.37 mmol) of tert-butyl 3-({6-[(tert-butoxycarbonyl)amino]-5-(trifluoroacetyl)pyridin-2-yl}amino)piperidine-1-carboxylate (Example 39A) were dissolved in 25 ml of a solution of hydrochloric acid in dioxane (4 M), and the mixture was stirred at RT for 20 h. After the reaction had gone to completion, the reaction mixture was diluted with diethyl ether (100 ml) and the precipitate was filtered off and washed with diethyl ether (100 ml) and dried. This gave 286 mg (64% of theory) of the product as a solid.

LCMS (method 6): $R_t$=0.81 min. (m/z=289 (M+H)$^+$)

$^1$H-NMR (400 MHz, DMSO-d$_6$): δ=9.26 (br s, 1H), 9.07 (br s, 1H), 8.8.34 (br s, 1H), 7.59 (d, 1H), 6.22 (br, 2H), 6.03 (d, 1H), 4.25 (br m, 1H), 3.36 (m, 1H), 3.13 (m, 1H), 2.93 (m, 2H), 2.00-1.85 (m, 2H), 1.73 (m, 1H), 1.56 (m, 1H).

Example 41A tert-Butyl 3-[(6-amino-5-nitropyridin-2-yl)amino]piperidine-1-carboxylate

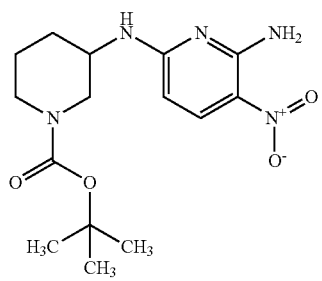 [SMILES: CC(C)(C)OC(=O)N1CCCC(Nc2ccc([N+](=O)[O-])c(N)n2)C1]

500 mg (2.11 mmol) of tert-butyl 3-aminopiperidine-1-carboxylate, 772 mg (4.22 mmol) of 2-amino-6-chloro-3-nitropyridine and 1.05 ml (6.34 mmol) of diisopropylethylamine were suspended in 18 ml of DMSO and heated in a microwave reactor at 120° C. for 45 min. The reaction mixture was purified by preparative reverse-phase HPLC. This gave 600 mg (81% of theory) of the product as a solid.

LCMS (method 6): $R_t$=1.77 min. (m/z=338 (M+H)$^+$)

Example 42A

3-Nitro-N$^6$-(piperidin-3-yl)pyridine-2,6-diamine hydrochloride

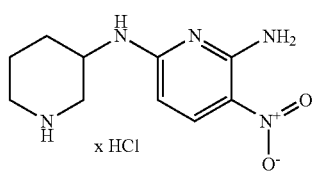 [SMILES: Nc1nc(NC2CCCNC2)ccc1[N+](=O)[O-]]

610 mg (1.62 mmol) of tert-butyl 3-[(6-amino-5-nitropyridin-2-yl)amino]piperidine-1-carboxylate (Example 41A) were dissolved in 40 ml of a solution of hydrochloric acid in dioxane (4 M), and the mixture was stirred at RT for 30 min. After the reaction had gone to completion, the solvent was removed completely. This gave 662 mg of the crude product.

LCMS (method 4): $R_t$=0.86 min. (m/z=238 (M+H)$^+$)

Example 43A

Methyl 4-amino-2-(methylsulfonyl)-1,3-thiazole-5-carboxylate

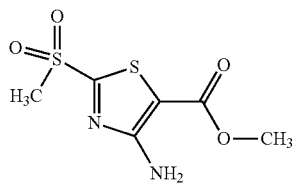

5.12 g (8.32 mmol) of Oxone® were dissolved in 170 ml of water and cooled to 5° C. A solution of 1 g (4.90 mmol) of methyl 4-amino-2-(methylsulfanyl)-1,3-thiazole-5-carboxylate in 18 ml of methanol was then added dropwise, and the solution was stirred at RT for 3 h. Most of the methanol was removed, and the remainder was extracted three times with dichloromethane. The combined organic phases were dried with sodium sulfate. Following removal of the solvent and drying of the residue under high vacuum, the solid obtained (824 mg (43% of theory)) was used without further purification.

LCMS (method 3): $R_t$=1.52 min. (m/z=237 (M+H)$^+$).

$^1$H-NMR (400 MHz, DMSO-d$_6$): δ=7.36 (s, br, 2H), 3.79 (s, 3H), 3.45 (s, 3H).

Example 44A tert-Butyl 3-{[4-amino-5-(methoxycarbonyl)-1,3-thiazol-2-yl]amino}piperidine-1-carboxylate

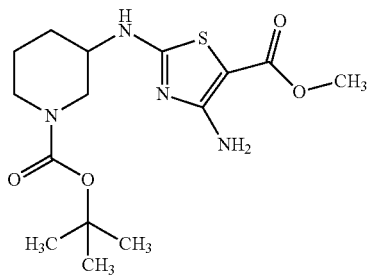 [SMILES: COC(=O)c1sc(NC2CCCN(C(=O)OC(C)(C)C)C2)nc1N]

Analogously to the preparation of Example 49A, 335 mg (1.42 mmol) of tert-butyl 3-aminopiperidine-1-carboxylate hydrochloride and 3190 mg (2.84 mmol) of methyl 4-amino-2-(methylsulfonyl)-1,3-thiazole-5-carboxylate gave 158 mg (29% of theory) of the product as a solid.

LCMS (method 8): $R_t$=1.06 min. (m/z=357 (M+H)$^+$).

$^1$H-NMR (400 MHz, DMSO-d$_6$): δ=8.32 (d, 1H), 6.79 (s, br, 2H), 3.60 (s, 3H), 3.55 (m, 2H), 1.89 (m, 1H), 1.71 (m, 1H), 1.5 (m, 1H), 1.35 (s, 11H).

Example 45A

Methyl 1-amino-2-(piperidin-3-ylamino)-1,3-thiazole-5-carboxylate dihydrochloride

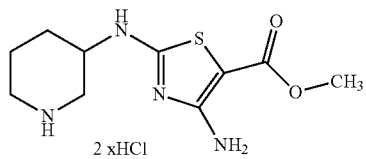 [SMILES: COC(=O)c1sc(NC2CCCNC2)nc1N]

Analogously to the preparation of Example 38A, 150 mg (0.39 mmol) of tert-butyl 3-{[4-amino-5-(methoxycarbonyl)-1,3-thiazol-2-yl]amino}piperidine-1-carboxylate and 20 ml of hydrochloric acid in dioxane (4M) gave 130 mg (99% of theory) of the product as a solid.

LCMS (method 8): $R_t$=0.26 min. (m/z=257 (M+H)$^+$).

$^1$H-NMR (400 MHz, DMSO-d$_6$): δ=9.04 (s, br, 2H), 8.51 (d, 1H), 3.9 (m, 2H), 3.6 (s, 3H), 3.34 (d, 1H), 3.11 (d, 1H), 2.75-2.94 (m, 2H), 1.93-2.04 (m, 1H), 1.8-1.91 (m, 1H), 1.60-1.76 (m, 1H), 1.43-1.57 (m, 1H).

Example 46A tert-Butyl 3-[(4-amino-5-cyano-1,3-thiazol-2-yl)amino]piperidine-1-carboxylate

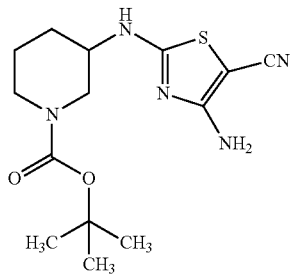 [SMILES: CC(C)(C)OC(=O)N1CCCC(Nc2nc(N)c(C#N)s2)C1]

643 mg (3.17 mmol) of 4-amino-2-(methylsulfonyl)-1,3-thiazole-5-carbonitrile (Example 6A) were dissolved in 16 ml of DMSO, and 500 mg (2.11 mmol) of tert-butyl 3-aminopiperidine-1-carboxylate and 3.49 ml (21.12 mmol) of N,N-diisopropylethylamine were added. The mixture was heated in a microwave at 120° C. for 45 min. The reaction mixture was taken up in a mixture of ethyl acetate and water. The organic phase was washed with saturated aqueous sodium chloride solution, dried over magnesium sulfate and concentrated on a rotary evaporator. The crude product was used without further purification.

LCMS (method 8): $R_t$=1.0 min. (m/z=357 (M+H)$^+$).

Example 47A

4-Amino-2-(piperidin-3-ylamino)-1,3-thiazole-5-carbonitrile dihydrochloride

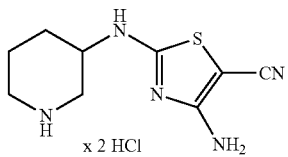

Analogously to the preparation of Example 38A, 240 mg (0.7 mmol) of tert-butyl 3-[(4-amino-5-cyano-1,3-thiazol-2-yl)amino]piperidine-1-carboxylate (Example 46A) and 25 ml of hydrochloric acid in dioxane (4M) gave 265 mg (57% of theory) of the product as a solid.

LCMS (method 9): $R_t$=0.74 min. (m/z=224 (M+H)$^+$).

Example 48A

1-[4-Amino-2-(methylsulfonyl)-1,3-thiazol-5-yl]ethanone

2.775 g (4.52 mmol) of Oxone® were dissolved in 9 ml of water, and 500 mg (2.66 mmol) of 1-[4-amino-2-(methylsulfanyl)-1,3-thiazol-5-yl]ethanone, dissolved in 9 ml of methanol, were added dropwise at 5° C. The mixture was stirred at RT for 3 h, the methanol was reduced on a rotary evaporator and the residue was extracted twice with dichloromethane. Removal of the solvent gave 395 mg (52% of theory) of the product as a solid.

LCMS (method 3): $R_t$=1.17 min. (m/z=221 (M+H)$^+$).

Example 49A tert-Butyl 3-[(5-acetyl-4-amino-1,3-thiazol-2-yl)amino]piperidine-1-carboxylate

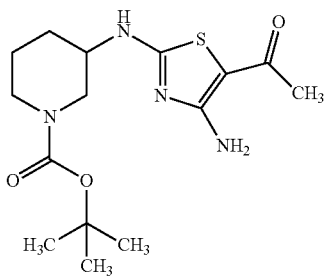 [SMILES: CC(=O)c1sc(NC2CCCN(C(=O)OC(C)(C)C)C2)nc1N]

390 mg (1.77 mmol) of 1-[4-amino-2-(methylsulfonyl)-1,3-thiazol-5-yl]ethanone (Example 48A) were dissolved in 5 ml of DMSO, and 209.6 mg (0.89 mmol) of tert-butyl 3-aminopiperidine-1-carboxylate and 0.585 ml (3.54 mmol) of N,N-diisopropylethylamine were added. The mixture was heated in a microwave at 120° C. for 45 min. This gave, after purification by preparative HPLC, 162 mg (52% of theory) of the product as a solid.

LCMS (method 8): $R_t$=1.87 min. (m/z=341 (M+H)$^+$).

$^1$H-NMR (400 MHz, DMSO-d$_6$): δ=8.56 (d, 1H), 7.70 (s, br, 2H), 3.81 (m, 4H), 3.56 (m, 2H), 2.02 (s, 3H), 1.91 (m, 1H), 1.71 (m, 1H), 1.51 (m, 1H), 1.36 (s, 9H).

Example 50A

1-[4-Amino-2-(piperidin-3-ylamino)-1,3-thiazol-5-yl]ethanone dihydrochloride

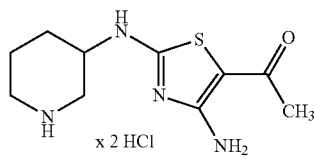

Analogously to the preparation of Example 38A, 160 mg (0.15 mmol) of tert-butyl 3-[(5-acetyl-4-amino-1,3-thiazol-2-yl)amino]piperidine-1-carboxylate (Example 49A) and 20 ml of hydrochloric acid in dioxane (4M) gave 40 mg (87% of theory) of the product as a solid.

LCMS (method 9): $R_t$=0.81 min. (m/z=241 (M+H)$^+$).

$^1$H-NMR (400 MHz, DMSO-d$_6$): δ=9.22 (s, br, 2H), 8.93 (d, 1H), 7.7 (s, br, 1H), 3.96 (m, 1H), 3.35 (d, 1H), 3.12 (d, 1H), 2.86 (m, 2H), 2.05 (s, 3H), 1.93-2.05 (m, 1H), 1.8-1.93 (m, 1H), 1.61-1.78 (m, 1H), 1.45-1.6 (m, 1H).

Example 51A

Methyl 2-[(tert-butoxycarbonyl)amino]-6-chloropyridine-3-carboxylate

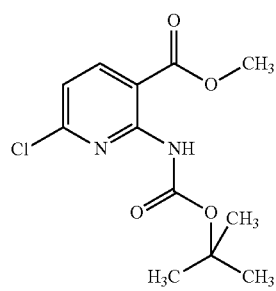 [SMILES: COC(=O)c1ccc(Cl)nc1NC(=O)OC(C)(C)C]

2.0 g (8.7 mmol) of tert-butyl (6-chloropyridin-2-yl)carbamate (Example 24A) were initially charged in 50 ml of THF and cooled to −78° C. 13.7 ml (22 mmol) of butyllithium (1.6 M) were added dropwise. After the dropwise addition had ended, the reaction was slowly warmed to −10° C. and kept at −10° C. for 2 h. The mixture was then once more cooled to −78° C., and 870 mg (9.2 mmol) of methyl chloroformate were added. The reaction solution was warmed to RT over a period of 12 h, and the reaction mixture was then poured into 150 ml of ethyl acetate and 80 ml of hydrochloric acid solution (1N) and stirred for 15 min. The organic phase was separated off, washed with water and saturated sodium bicarbonate solution, dried over magnesium sulfate and concentrated on a rotary evaporator. The reaction mixture was chromatographed on silica gel (mobile phase cyclohexane/ethyl acetate 10:1). This gave 1018 mg (33% of theory) of the product as an oil.

LCMS (method 8): $R_t$=1.25 min. (m/z=187 (M+H-Boc)$^+$)

Example 52A

Methyl 2-[(tert-butoxycarbonyl)amino]-6-({2-[(tert-butoxycarbonyl)amino]ethyl}amino)pyridine-3-carboxylate

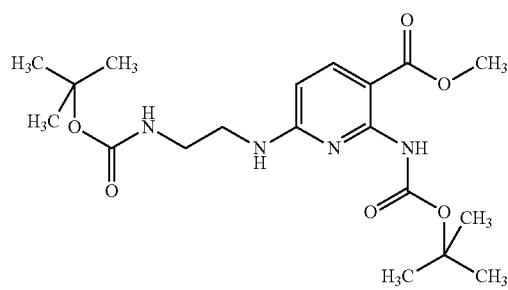 [SMILES: COC(=O)c1ccc(NCCNC(=O)OC(C)(C)C)nc1NC(=O)OC(C)(C)C]

Analogously to the preparation of Example 33A, 650 mg (2.3 mmol) of methyl 2-[(tert-butoxycarbonyl)amino]-6-chloropyridine-3-carboxylate (Example 51A) and 363 mg (2.3 mmol) of N-Boc-ethylenediamine gave 500 mg (50% of theory) of the product as a solid.

LCMS (method 8): $R_t$=1.32 min. (m/z=411 (M+H)$^+$).

Example 53A

Methyl 2-amino-6-[(2-aminoethyl)amino]pyridine-3-carboxylate dihydrochloride

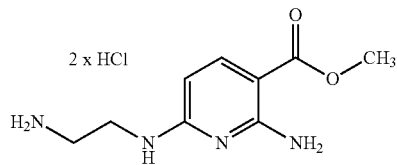

Analogously to the preparation of Example 38A, 496 mg (1.2 mmol) of methyl 2-[(tert-butoxycarbonyl)amino]-6-({2-[(tert-butoxycarbonyl)amino]ethyl}amino)pyridine-3-carboxylate (Example 52A) gave 363 mg (82% of theory) of the product as a solid.

LCMS (method 9): $R_t$=0.75 min. (m/z=212 (M+H-2HCl)$^+$).

Example 54A

6-[(2-{[6-(2,4-Dichlorophenyl)-2-formylpyrazolo[1,5-a]pyrazin-4-yl]amino}ethyl)amino]pyridine-3-carbonitrile

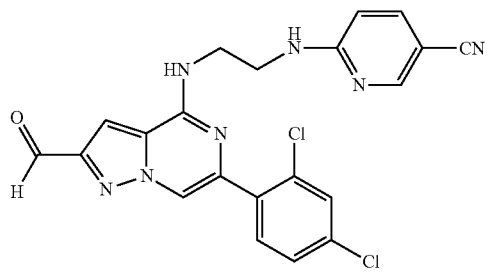 [SMILES: N#Cc1ccc(NCCNc2nc(-c3ccc(Cl)cc3Cl)cn3nc(C=O)cc23)nc1]

1.2 g (2.64 mmol) of 6-[(2-{[6-(2,4-dichlorophenyl)-2-(hydroxymethyl)pyrazolo[1,5-a]-pyrazin-4-yl}amino]ethyl)amino]pyridine-3-carbonitrile (Example 42) were suspended in 80 ml of dichloromethane (shaken with water beforehand). 80 ml of 1,2-dimethoxyethane and 40 ml of DMF were then added, and the mixture was cooled to 0° C. 2.46 g (5.81 mmol) of Dess-Martin periodinane were added, ice-bath cooling was removed and the mixture was stirred at RT for 2 h. Ethyl acetate was added, and the mixture was washed first with a 10% strength sodium thiosulfate solution and then with saturated aqueous sodium bicarbonate solution. Drying of the organic phase with sodium sulfate and removal of the solvent under reduced pressure gave 1.2 g (94% of theory) of the product as a solid which was reacted without further purification.

LCMS (method 9): $R_t$=2.50 min. (m/z=452 (M+H)$^+$).

$^1$H-NMR (400 MHz, DMSO-d$_6$): δ=10.1 (s, 1H), 8.38 (d, 1H), 8.33 (s, 1H), 8.30 (t, 1H), 7.77 (m, 1H), 7.75 (d, 1H), 7.67 (d, 1H), 7.59 (d, 1H), 7.55 (s, 1H), 7.53 (dd, 1H), 6.52 (d, 1H), 3.55-3.7 (m, 4H).

Example 55A 6-(2,4-Dichlorophenyl)-4-oxo-4,5-dihydropyrazolo[1,5-a]pyrazine-2-carboxylic acid

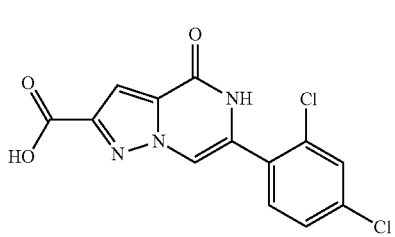 [SMILES: O=C(O)c1cc2c(=O)[nH]c(-c3ccc(Cl)cc3Cl)cn2n1]

500 mg (1.42 mmol) of ethyl 6-(2,4-dichlorophenyl)-4-oxo-4,5-dihydropyrazolo[1,5-a]pyrazine-2-carboxylate (Example 11A) were suspended in 60 ml of 1,2-dimethoxyethane, 1M aqueous sodium hydroxide (5.7 ml, 5.7 mmol) was added and the mixture was stirred at RT for 3 h. The reaction mixture was poured into water and acidified to pH 2 using 2M aqueous hydrochloric acid. The precipitate was filtered off and washed with water. Drying gave 430 mg (93% of theory) of the product as a solid.

LCMS (method 6): $R_t$=1.31 min. (m/z=324 (M+H)$^+$).

$^1$H-NMR (400 MHz, DMSO-d$_6$): δ=13.29 (br, 1H), 11.80 (s, 1H), 7.94 (s, 1H), 7.84 (d, 1H), 7.66 (d, 1H), 7.59 (dd, 1H), 7.48 (s, 1H).

Example 56A 6-(2,4-Dichlorophenyl)-4-oxo-4,5-dihydropyrazolo[1,5-a]pyrazine-2-carboxamide

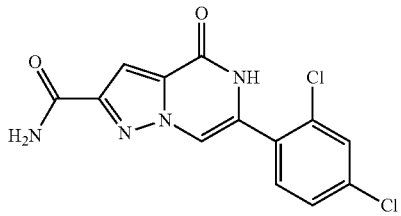 [SMILES: NC(=O)c1cc2c(=O)[nH]c(-c3ccc(Cl)cc3Cl)cn2n1]

360 mg (1.11 mmol) of 6-(2,4-dichlorophenyl)-4-oxo-4,5-dihydropyrazolo[1,5-a]pyrazine-2-carboxylic acid (Example 55A) were initially charged in dichloromethane (30 ml) and DMF (10 ml), and 320 mg (1.67 mmol) of EDC, 225 mg (1.67 mg) HOBt and 407 mg (3.33 mmol) of DMAP were added, followed by 0.5M ammonia in dioxane (2.44 ml, 1.22 mmol). The reaction mixture was stirred at RT for 20 h, the solvent was concentrated, the residue was poured into water (25 ml) and the precipitate was filtered off and washed with water and acetonitrile and dried. Drying gave 260 mg (72% of theory) of the product as a solid.

LCMS (method 3): $R_t$=1.69 min. (m/z=323 (M+H)$^+$).

$^1$H-NMR (400 MHz, DMSO-d$_6$): δ=11.77 (br, 1H), 7.86 (s, 1H), 7.84 (m, 2H), 7.65 (d, 1H), 7.59 (m, 2H), 7.47 (s, 1H).

Example 57A

4-Chloro-6-(2,4-dichlorophenyl)pyrazolo[1,5-a]pyrazine-2-carbonitrile

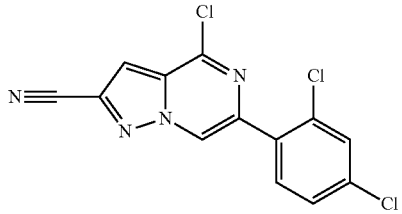 [SMILES: N#Cc1cc2c(Cl)nc(-c3ccc(Cl)cc3Cl)cn2n1]

Analogously to the preparation of Example 16A, 260 mg (0.81 mmol) of 6-(2,4-dichlorophenyl)-4-oxo-4,5-dihydropyrazolo[1,5-a]pyrazine-2-carboxamide (Example 56A) gave, by reaction with phosphoryl chloride, 230 mg (77% of theory) of the product as a solid.

LCMS (method 3): $R_t$=2.86 min. (m/z=323 (M+H)$^+$).

WORKING EXAMPLES

Example 1

6-[(2-{[6-(2,4-Dichlorophenyl)imidazo[1,2-a]pyrazin-8-yl]amino}ethyl)amino]nicotinonitrile

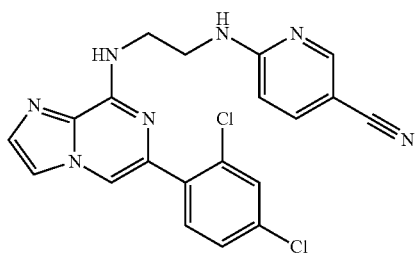 [SMILES: N#Cc1ccc(NCCNc2nc(-c3ccc(Cl)cc3Cl)cn3ccnc23)nc1]

108 mg (0.3625 mmol) of the 8-chloro-6-(2,4-dichlorophenyl)imidazo[1,2-a]pyrazine (Example 5A) were initially charged in 3 ml of DMSO, and 150 mg (0.543 mmol) of 6-[(2-aminoethyl)amino]nicotinonitrile (Example 2A) and 0.63 ml (3.62 mmol) of N,N-diisopropylethylamine were added. The mixture was heated at 120° C. for 12 h. Purification by chromatography on silica gel 60 (mobile phase: dichloromethane/methanol 100:1) gave 12 mg (7% of theory) of the product.

LCMS (method 6): $R_t$=1.97 min. (m/z=424 (M+H)$^+$)

$^1$H-NMR (400 MHz, DMSO-d$_6$): δ=8.35 (d, 1H), 8.09 (s, 1H), 7.94 (s, 1H), 7.74 (s, br, 1H), 7.70 (d, 2H), 7.63 (d, 1H), 7.56 (d, 2H), 7.49 (dd, 1H), 6.53 (s, br, 1H), 3.66 (t, 2H), 3.58 (t, br, 2H).

Example 2

4-Amino-2-[(2-{[6-(2,4-dichlorophenyl)imidazo[1,2-a]pyrazin-8-yl]amino}ethyl)amino]-1,3-thiazole-5-carbonitrile trifluoroacetate

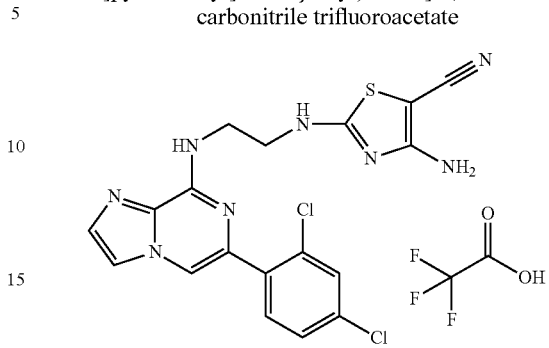

Under argon, 80 mg (0.2 mmol) of 4-amino-2-({2-[(6-bromoimidazo[1,2-a]pyrazin-8-yl)amino]ethyl}amino)-1,3-thiazole-5-carbonitrile (Example 9A) were initially charged in 4.5 ml of dioxane and 1.3 ml of saturated sodium carbonate solution, and 48 mg (0.25 mmol) of 2,4-dichlorobenzeneboronic acid and 22 mg (0.02 mmol) of tetrakis(triphenylphosphine)palladium(0) were added. The mixture was heated in a microwave at 160° C. for 1 h. The reaction mixture was concentrated on a rotary evaporator. This gave, after purification by preparative HPLC, 35 mg (33% of theory) of the product as a solid.

LCMS (method 8): $R_t$=1.16 min. (m/z=444 (M+H)$^+$)

$^1$H-NMR (400 MHz, DMSO-d$_6$): δ=8.48 (t, 1H), 8.15 (s, 1H), 7.99 (s, 1H), 7.9 (s, broad, 1H), 7.72 (d, 1H), 7.65 (d, 1H), 7.62 (s, 1H), 7.51 (dd, 1H), 3.67 (q, 2H), 3.49 (q, 2H).

Example 3

Ethyl 4-({2-[(5-cyanopyridin-2-yl)amino]ethyl}amino)-6-(2,4-dichlorophenyl)pyrazolo[1,5-a]pyrazine-2-carboxylate

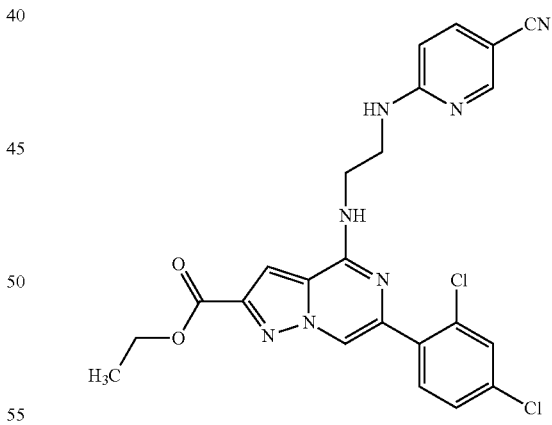

1 g (5 mmol) of ethyl 4-chloro-6-(2,4-dichlorophenyl)pyrazolo[1,5-a]pyrazine-2-carboxylate (Example 12A) was initially charged in 15 ml of dry DMSO, and 1.55 g (4.22 mmol) of 6-[(2-aminoethyl)amino]nicotinonitrile dihydrochloride (Example 2A) and 5.8 ml (33.5 mmol) of N,N-diisopropylethylamine were added and the mixture was heated in a microwave at 150° C. for 30 min. Ethyl acetate and 10% strength citric acid were added, and the reaction mixture was extracted. The organic phase was washed with sodium chloride solution and dried over magnesium sulfate. This gave, after concentration, 1.4 g (70% of theory) of the product as a solid.

LCMS (method 6): $R_t$=2.31 min. (m/z=496 (M+H)$^+$)

$^1$H-NMR (400 MHz, DMSO-d$_6$): δ=8.38 (d, 1H), 8.3 (s, 1H), 8.15 (t, 1H), 7.73 (d, 1H), 7.66 (d, 2H), 7.59 (dd, 1H), 7.57 (s, 1H), 7.52 (dd, 1H), 6.52 (d, 1H), 4.35 (t, 2H), 3.7-3.55 (m, 4H), 1.34 (s, 3H).

Example 4

4-({2-[(5-Cyanopyridin-2-yl)amino]ethyl}amino)-6-(2,4-dichlorophenyl)pyrazolo[1,5-a]pyrazine-2-carboxylic acid hydrochloride

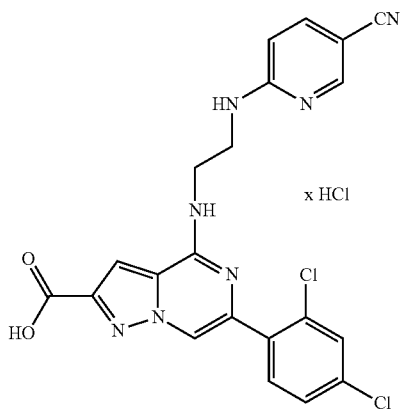 [SMILES: N#Cc1ccc(NCCNc2nc(-c3ccc(Cl)cc3Cl)cn3nc(C(=O)O)cc23)nc1]

80 mg (0.16 mmol) of ester (Example 3) were dissolved in 5 ml of 1,2-dimethoxyethane, and 2.5 ml of water and 0.43 ml (0.4 mmol) of 1N sodium hydroxide solution were added. The solution was stirred at RT for 2 h. 20 ml of dilute hydrochloric acid (pH 3) were initially charged, and the reaction solution was slowly added dropwise. The mixture was stirred for another 30 min, and the product was filtered off and washed with diethyl ether. This gave, after drying under high vacuum, 70 mg (84% of theory) of the product as a solid.

LCMS (method 3): $R_t$=2.59 min. (m/z=468 (M+H)$^+$)

$^1$H-NMR (400 MHz, DMSO-d$_6$): δ=8.38 (d, 1H), 8.26 (s, 1H), 8.17 (t, 1H), 7.77 (s, broad, 1H), 7.73 (d, 1H), 7.66 (d, 1H), 7.59 (d, 1H), 7.52 (dd, 1H), 7.51 (s, 1H), 6.53 (d, 1H), 3.7-3.56 (m, 4H).

General Description for Amide Coupling Experiments:

0.16 mmol of acid (Example 4) is initially charged in 2 ml of DMF, and 0.17 mmol of HATU, 0.48 mmol of N,N-diisopropylethylamine and 0.21 mmol of amine are added in succession. The mixture is stirred at RT for 12 h. Purification by preparative HPLC gives 60%-95% of theory of the product as a solid.

The compounds below were prepared according to the general description for amide coupling experiments.

| Ex. | Structure | Characterization |
|---|---|---|
| 5 | (piperazinyl-methyl ethylamino ethyl amide of pyrazolo[1,5-a]pyrazine with 5-cyanopyridin-2-ylamino and 2,4-dichlorophenyl substituents) | LC/MS (method 8): $R_t$ = 0.89 min, (m/z = 593 (M + H)$^+$) $^1$H-NMR (400 MHz, DMSO-d$_6$): δ = 10.81 (s, 1H), 8.38 (d, 1H), 8.28 (s, 1H), 8.22 (s, 1H), 7.91 (s, 1H), 7.74 (d, 1H), 7.66 (d, 1H), 7.61 (d, 1H), 7.53 (dd,1H), 7.45 (s, 1H), 6.56 (d, 1H), 4.89 (d, 1H), 4.61 (d, 1H), 3.65 (m, 6H), 3.48 (q, 3H), 3.27 (t, 1H), 3.12 (m, 4H), 2.79 (d, 3H). |
| 6 | (4-methylpiperazine amide of pyrazolo[1,5-a]pyrazine with 5-cyanopyridin-2-ylamino ethylamino and 2,4-dichlorophenyl substituents) | LC/MS (method 6): $R_t$ = 1.60 min, (m/z = 551 (M + H)$^+$) $^1$H-NMR (400 MHz, DMSO-d$_6$): δ = 8.38 (d, 1H), 8.28 (s, 1H), 8.22 (s, 1H), 7.91 (s, 1H), 7.74 (d, 1H), 7.66 (d, 1H), 7.61 (d, 1H), 7.53 (dd,1H), 7.45 (s, 1H), 6.56 (d, 1H), 3.67 (m, 8H), 3.38 (s, broad, 4H), 2.38 (s, 3H). |

| Ex. | Structure | Characterization |
|---|---|---|
| 7 | 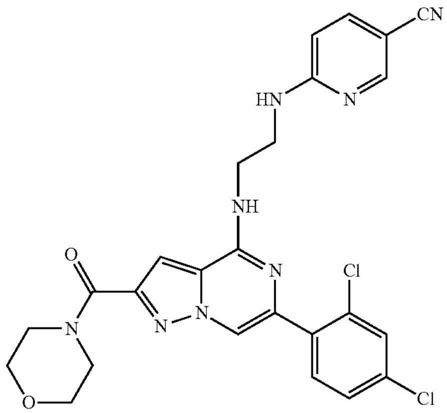 [SMILES: N#Cc1ccc(NCCNc2nc(-c3ccc(Cl)cc3Cl)cn3nc(C(=O)N4CCOCC4)cc23)nc1] | LC/MS (method 8): $R_t$ = 1.28 min, (m/z = 537 (M + H)$^+$) 1H-NMR (400 MHz, DMSO-d$_6$): δ = 8.39 (d, 1H), 8.25 (s, broad, 1H), 8.23 (s, 1H), 7.73 (d, 1H), 7.66 (d, 2H), 7.63 (dd, 1H), 7.52 (d, 1H), 7.41 (s, 1H), 6.6 (d, 1H), 3.73 (m, broad, 8H), 3.63 (s, broad, 4H). |
| 8 | 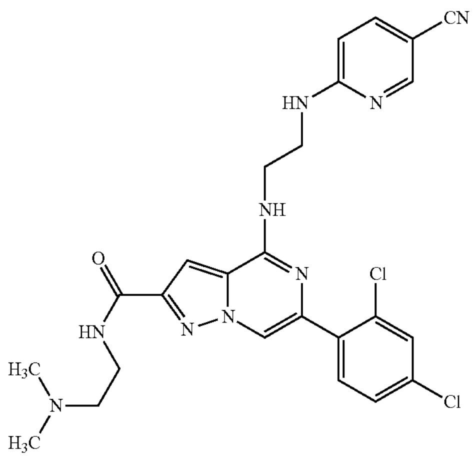 [SMILES: CN(C)CCNC(=O)c1cc2c(NCCNc3ccc(C#N)cn3)nc(-c3ccc(Cl)cc3Cl)cn2n1] | LC/MS (method 8): $R_t$ = 0.98 min, (m/z = 538 (M + H)$^+$) 1H-NMR (400 MHz, DMSO-d$_6$): δ = 10.09 (s, 1 H), 8.8 (t, 1H), 8.39 (d, 2H), 8.19 (s, 1H), 7.75 (d, 1H), 7.7 (d, 1H), 7.63 (dd, 1H), 7.54 (m, 2H), 6.62 (d, 1H), 3.73-3.58 (m, 6H), 3.27 (q, 2H), 2.8 (d, 6H). |

Example 9

6-({2-[(5,7-Dimethyl-2-phenylimidazo[5,1-f][1,2,4]triazin-4-yl)amino]ethyl}amino)nicotinonitrile

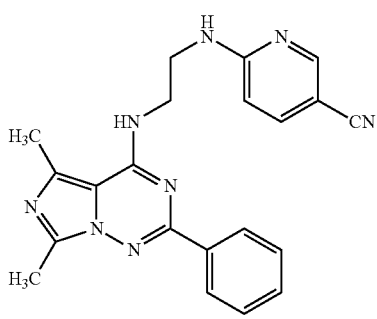 [SMILES: Cc1nc(C)n2nc(-c3ccccc3)nc(NCCNc3ccc(C#N)cn3)c12]

183 mg (0.71 mmol) of the 4-chloro-5,7-dimethyl-2-phenylimidazo[5,1-f][1,2,4]triazine (Example 16A) were initially charged in 4 ml of DMSO, and 200 mg (0.85 mmol) of 6-[(2-aminoethyl)amino]nicotinonitrile (Example 2A) and 1.23 ml (7 mmol) of N,N-diisopropylethylamine were added and the mixture was heated at 150° C. for 12 h. Purification by chromatography on silica gel (mobile phase: dichloromethane/methanol 100:1) gave 10 mg (4% of theory) of the product.

LCMS (method 6): $R_t$=1.40 min. (m/z=385 (M+H)$^+$)

$^1$H-NMR (400 MHz, DMSO-d$_6$): δ=8.43 (s, 1H), 8.12 (d, 1H), 7.99 (d, 1H), 7.82 (t, 1H), 7.59 (t, 2H), 7.55 (q, 1H), 7.46 (m, 2H), 6.50 (d, 1H), 3.86 (q, 2H), 3.67 (s, broad, 2H), 2.5 (s, 6H).

Example 10

4-Amino-2-{[2-({6-[4-(trifluoromethyl)phenyl]imidazo[1,2-a]pyrazin-8-yl}amino)ethyl]amino}-1,3-thiazole-5-carbonitrile trifluoroacetate

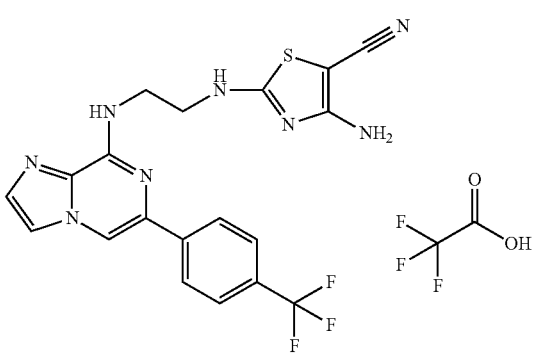 [SMILES: N#Cc1sc(NCCNc2nc(-c3ccc(C(F)(F)F)cc3)cn3ccnc23)nc1N ; O=C(O)C(F)(F)F]

Under argon, 80 mg (0.192 mmol) of 4-amino-2-({2-[(6-bromoimidazo[1,2-a]pyrazin-8-yl)amino]ethyl}amino)-1,3-thiazole-5-carbonitrile (Example 9A) were initially charged in 4.5 ml of dioxane and 1.3 ml of saturated sodium carbonate solution, and 47 mg (0.25 mmol) of 4-(trifluoromethyl)phenyl]boronic acid and 22 mg (0.019 mmol) of tetrakis(triphenylphosphine)palladium(0) were added. The mixture was heated at 120° C. for 15 h. The reaction mixture was concentrated on a rotary evaporator. This gave, after purification by preparative HPLC, 5 mg (5% of theory) of the product as a solid.

LCMS (method 8): $R_t$=1.16 min. (m/z=445 (M+H)$^+$)

$^1$H-NMR (400 MHz, DMSO-d$_6$): δ=8.59 (s, 1H), 8.53 (t, 1H), 8.13 (d, 2H), 7.93 (s, 1H), 7.86 (t, 1H), 7.79 (d, 2H), 7.58 (s, 1H), 6.74 (s, broad, 2H), 3.80 (q, 2H), 3.54 (q, 2H).

Example 11

Ethyl 4-({2-[(4-amino-5-cyano-1,3-thiazol-2-yl)amino]ethyl}amino)-6-(2,4-dichlorophenyl)pyrazolo[1,5-a]pyrazine-2-carboxylate

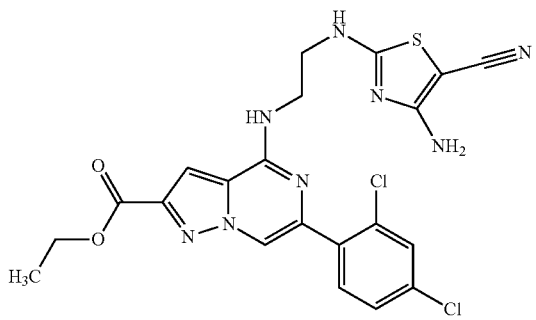 [SMILES: CCOC(=O)c1cc2c(NCCNc3nc(N)c(C#N)s3)nc(-c3ccc(Cl)cc3Cl)cn2n1]

Analogously to the procedure described for Example 3, 300 mg (0.769 mmol) of ethyl 4-chloro-6-(2,4-dichlorophenyl)pyrazolo[1,5-a]pyrazine-2-carboxylate (Example 12A) gave, by reaction with 239 mg (0.92 mmol) of 4-amino-2-[(2-aminoethyl)amino]-1,3-thiazole-5-carbonitrile dihydrochloride (Example 8A) and purification by preparative HPLC, 110 mg (26% of theory) of the product as a solid.

LCMS (method 3): $R_t$=2.58 min. (m/z=517 (M+H)$^+$)

$^1$H-NMR (400 MHz, DMSO-d$_6$): δ=8.49 (t, 1H), 8.32 (s, 1H), 8.17 (t, 1H), 7.74 (d, 1H), 7.66 (d, 1H), 7.58 (s, 1H), 7.53 (dd, 1H), 6.70 (s, br, 2H), 4.35 (q, 2H), 3.66 (dd, 2H), 3.52 (dd, 2H), 1.34 (t, 3H).

Example 12

Ethyl 4-{3-[(4-amino-5-cyano-1,3-thiazol-2-yl)amino]piperidin-1-yl}-6-(2,4-dichlorophenyl)pyrazolo[1,5-a]pyrazine-2-carboxylate

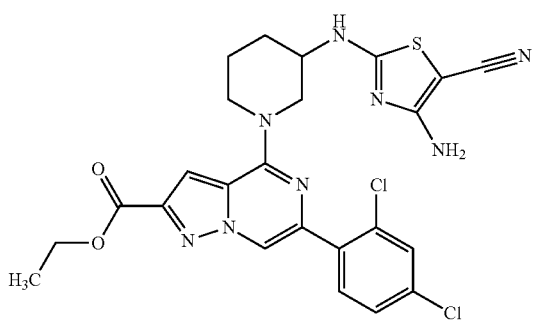 [SMILES: CCOC(=O)c1cc2c(N3CCCC(Nc4nc(N)c(C#N)s4)C3)nc(-c3ccc(Cl)cc3Cl)cn2n1]

Analogously to the procedure described for Example 3, 52.1 mg (0.133 mmol) of ethyl 4-chloro-6-(2,4-dichlorophenyl)pyrazolo[1,5-a]pyrazine-2-carboxylate (Example 12A) gave, by reaction with 132 mg (0.2 mmol) of 4-amino-2-(piperidin-3-ylamino)-1,3-thiazole-5-carbonitrile dihydrochloride (Example 47A) and purification by preparative HPLC, 52 mg (70% of theory) of the product as a solid.

LCMS (method 8): $R_t$=1.47 min. (m/z=557 (M+H)$^+$)

$^1$H-NMR (400 MHz, DMSO-d$_6$): δ=8.8 (s, 2H), 7.74 (d, 1H), 7.72 (d, 1H), 7.6 (s, 1H), 7.54 (dd, 1H), 6.72 (s, 2H), 4.3-4.44 (m, 3H), 4.08 (d, 1H), 3.86 (s, br, 1H), 3.4-3.5 (m, 2H), 2.04 (m, 1H), 1.90 (m, 1H), 1.65 (t, 2H), 1.35 (t, 3H).

Example 13

Ethyl 4-{3-[(6-amino-5-nitropyridin-2-yl)amino]piperidin-1-yl}-6-(2,4-dichlorophenyl)pyrazolo[1,5-a]pyrazine-2-carboxylate trifluoroacetate

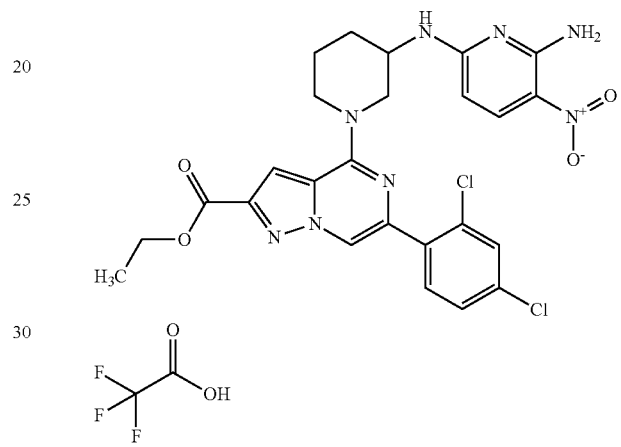

Analogously to the procedure described for Example 3, 70 mg (0.179 mmol) of ethyl 4-chloro-6-(2,4-dichlorophenyl)pyrazolo[1,5-a]pyrazine-2-carboxylate (Example 12A) gave, by reaction with 83 mg (0.27 mmol) of 3-nitro-N$^6$-(piperidin-3-yl)pyridine-2,6-diamine dihydrochloride (Example 42A) and purification by preparative HPLC, 83 mg (67% of theory) of the product as a solid.

LCMS (method 6): $R_t$=2.56 min. (m/z=571 (M+H)$^+$)

$^1$H-NMR (400 MHz, DMSO-d$_6$): δ=8.48 (s, 1H), 8.14 (s, br, 1H), 7.95 (d, 1H), 7.90 (d, 1H), 7.72 (m, 3H), 7.51 (dd, 1H), 7.39 (s, 1H), 5.92 (d, 1H), 4.32 (q, 2H), 4.19 (d, 1H), 3.98 (m, 1H), 3.64 (m, 2H), 2.0 (m, 2H), 1.69 (m, 2H), 1.30 (t, 3H).

Example 14

Ethyl 4-{3-[(6-amino-5-nitropyridin-2-yl)amino]piperidin-1-yl}-6-(2,4-dichlorophenyl)pyrazolo[1,5-a]pyrazine-2-carboxylate trifluoroacetate

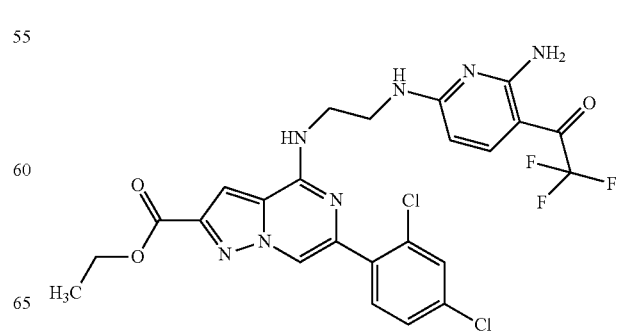

Analogously to the procedure described for Example 3, 70 mg (0.179 mmol) of ethyl 4-chloro-6-(2,4-dichlorophenyl)pyrazolo[1,5-a]pyrazine-2-carboxylate (Example 12A) gave, by reaction with 83 mg (0.27 mmol) of 1-{2-amino-6-[(2-aminoethyl)amino]pyridin-3-yl}-2,2,2-trifluoroethanone hydrochloride (Example 34A) and purification by preparative HPLC (mobile phase: acetonitrile/water gradient with 0.1% trifluoroacetic acid), 83 mg (67% of theory) of the product as a solid.

LCMS (method 6): $R_t$=2.56 min. (m/z=571 (M+H)$^+$)

$^1$H-NMR (400 MHz, DMSO-d$_6$): δ=8.48 (s, 1H), 8.14 (s, br, 1H), 7.95 (d, 1H), 7.90 (d, 1H), 7.72 (m, 3H), 7.51 (dd, 1H), 7.39 (s, 1H), 5.92 (d, 1H), 4.32 (q, 2H), 4.19 (d, 1H), 3.98 (m, 1H), 3.64 (m, 2H), 2.0 (m, 2H), 1.69 (m, 2H), 1.30 (t, 3H).

Example 15

Ethyl 4-(3-{[4-amino-5-(methoxycarbonyl)-1,3-thiazol-2-yl]amino}piperidin-1-yl)-6-(2,4-dichlorophenyl)pyrazolo[1,5-a]pyrazine-2-carboxylate

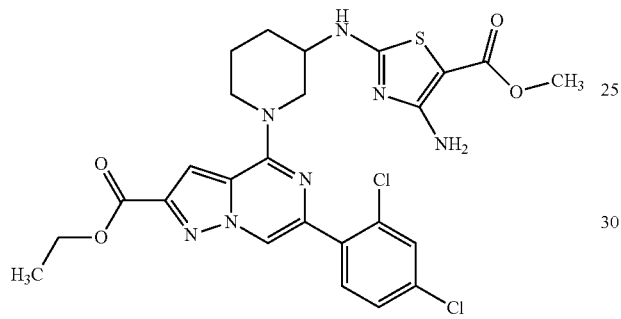

Analogously to the procedure described for Example 3, 63 mg (0.162 mmol) of ethyl 4-chloro-6-(2,4-dichlorophenyl)pyrazolo[1,5-a]pyrazine-2-carboxylate (Example 12A) gave, by reaction with 89.9 mg (0.243 mmol) of methyl 4-amino-2-(piperidin-3-ylamino)-1,3-thiazole-5-carboxylate dihydrochloride (Example 45A) and purification by preparative HPLC, 68 mg (69% of theory) of the product as a solid.

LCMS (method 6): $R_t$=2.58 min. (m/z=590 (M+H)$^+$)

$^1$H-NMR (400 MHz, DMSO-d$_6$): δ=8.50 (s, 1H), 8.47 (d, 1H), 7.72 (d, 2H), 7.65 (s, 1H), 7.52 (dd, 1H), 6.81 (s, br, 2H), 4.37 (m, 3H), 4.13 (dt, 1H), 3.87 (m, 1H), 3.61 (s, 3H), 2.06 (m, 1H), 1.92 (m, 1H), 1.65 (m, 2H), 1.34 (t, 3H).

Example 16

Ethyl 4-{3-[(6-amino-5-nitropyridin-2-yl)amino]piperidin-1-yl}-6-(2,4-dichlorophenyl)pyrazolo[1,5-a]pyrazine-2-carboxylate trifluoroacetate

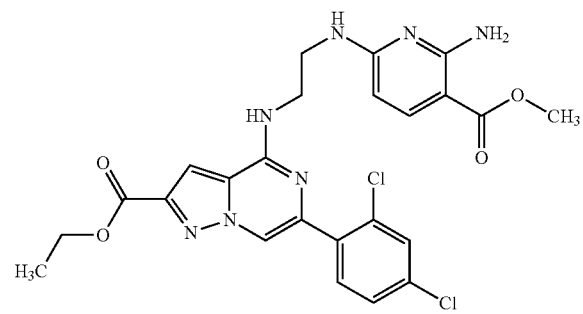 [SMILES: CCOC(=O)c1cc2c(NCCNc3ccc(C(=O)OC)c(N)n3)nc(-c3ccc(Cl)cc3Cl)cn2n1]

Analogously to the procedure described for Example 3, 70 mg (0.179 mmol) of ethyl 4-chloro-6-(2,4-dichlorophenyl)pyrazolo[1,5-a]pyrazine-2-carboxylate (Example 12A) gave, by reaction with 83 mg (0.27 mmol) of methyl 2-amino-6-[(2-aminoethyl)amino]pyridine-3-carboxylate dihydrochloride (Example 53A) and purification by preparative HPLC (mobile phase: acetonitrile/water gradient with 0.1% trifluoroacetic acid), 83 mg (67% of theory) of the product as a solid.

LCMS (method 6): $R_t$=2.56 min. (m/z=571 (M+H)$^+$)

$^1$H-NMR (400 MHz, DMSO-d$_6$): δ=8.48 (s, 1H), 8.14 (s, br, 1H), 7.95 (d, 1H), 7.90 (d, 1H), 7.72 (m, 3H), 7.51 (dd, 1H), 7.39 (s, 1H), 5.92 (d, 1H), 4.32 (q, 2H), 4.19 (d, 1H), 3.98 (m, 1H), 3.64 (m, 2H), 2.0 (m, 2H), 1.69 (m, 2H), 1.30 (t, 3H).

Example 17

Ethyl 4-{3-[(5-acetyl-4-amino-1,3-thiazol-2-yl)amino]piperidin-1-yl}-6-(2,4-dichlorophenyl)pyrazolo[1,5-a]pyrazine-2-carboxylate trifluoroacetate

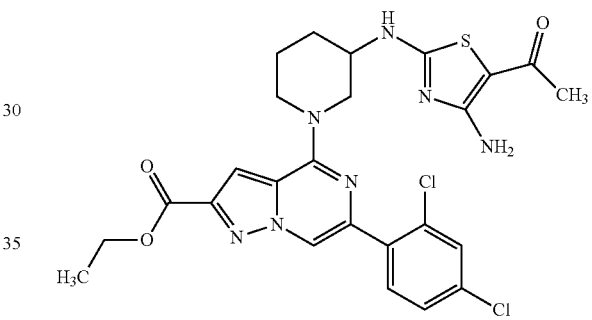

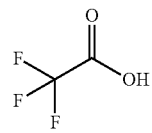

Analogously to the procedure described for Example 3, 61 mg (0.155 mmol) of ethyl 4-chloro-6-(2,4-dichlorophenyl)pyrazolo[1,5-a]pyrazine-2-carboxylate (Example 12A) gave, by reaction with 73 mg (0.233 mmol) of 1-[4-amino-2-(piperidin-3-ylamino)-1,3-thiazol-5-yl]ethanone dihydrochloride (Example 50A) and purification by preparative HPLC (mobile phase: acetonitrile/water gradient with 0.1% trifluoroacetic acid), 63 mg (59% of theory) of the product as a solid.

LCMS (method 6): $R_t$=2.40 min. (m/z=574 (M+H)$^+$)

$^1$H-NMR (400 MHz, DMSO-d$_6$): δ=8.65 (d, 1H), 8.51 (s, 1H), 7.74 (d, 1H), 7.71 (d, 1H), 7.64 (s, 1H), 7.52 (dd, 1H), 4.31-4.43 (m, 3H), 4.13 (d, 2H), 3.85 (s, br, 1H), 3.44 (m, 2H), 2.06 (m, 1H), 1.98 (s, 3H), 1.92 (m, 1H), 1.6-1.72 (m, 2H), 1.34 (t, 3H).

Analogously to the procedure described for Example 4, the esters in question were converted by hydrolysis with lithium hydroxide or sodium hydroxide solution in the corresponding acids.

| Ex. | Structure | Characterization |
|---|---|---|
| 18 | 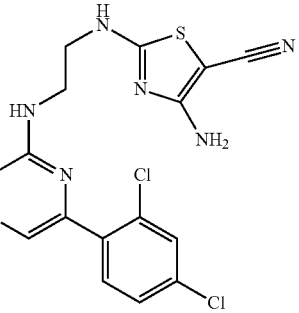 | LC/MS (method 8): $R_t$ = 1.11 min, (m/z = 489 (M + H)$^+$) |
| 19 | 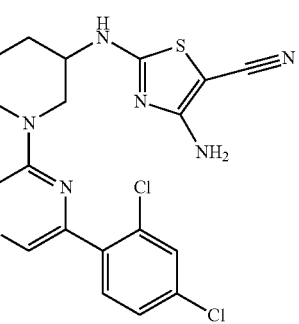 | LC/MS (method 6): $R_t$ = 2.10 min, (m/z = 529 (M + H)$^+$) |
| 20 | 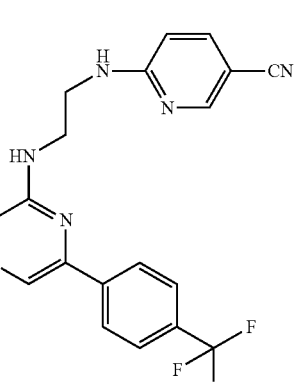 | LC/MS (method 6): $R_t$ = 1.98 min, (m/z = 468 (M + H)$^+$) $^1$H-NMR (400 MHz, DMSO-d$_6$): δ = 8.79 (s, 1H), 8.45 (s, 1H), 8.24 (d, 2H), 8.18 (t, 1H), 7.84 (br, 1H), 7.79 (d, 2H), 7.63 (d, 1H), 7.51 (s, 1H), 6.53 (m, 1H), 3.79 (m, 2H), 3.66 (m, 2H). |
The amides below were prepared analogously to the general description for amide coupling experiments (cf. Example 5) from the corresponding carboxylic acids.

| Ex. | Structure | Characterization |
|---|---|---|
| 21 | 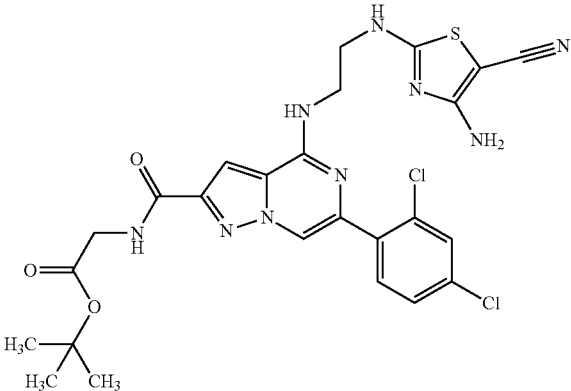 [SMILES: CC(C)(C)OC(=O)CNC(=O)c1cc2c(NCCNc3nc(N)c(C#N)s3)nc(-c3ccc(Cl)cc3Cl)cn2n1] | LC/MS (method 3): R_t = 2.69 min, (m/z = 602 (M + H)+) |
| 22 | 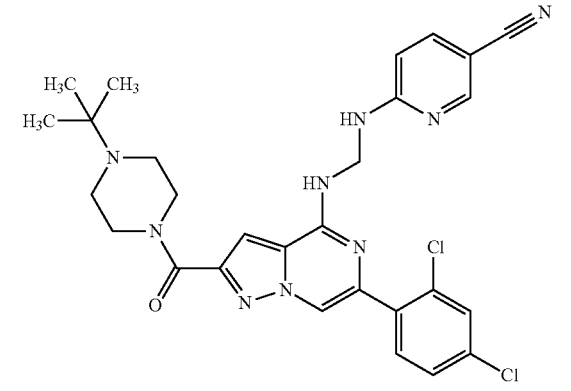 | LC/MS (method 6): R_t = 1.38 min, (m/z = 592 (M + H)+) |
| 23 | 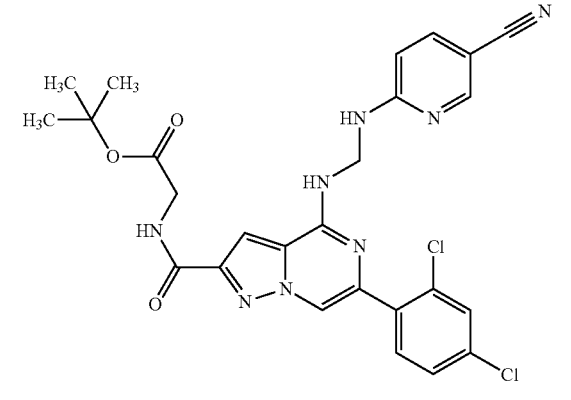 | LC/MS (method 3): R_t = 2.95 min, (m/z = 581 (M + H)+) |
| 24 | 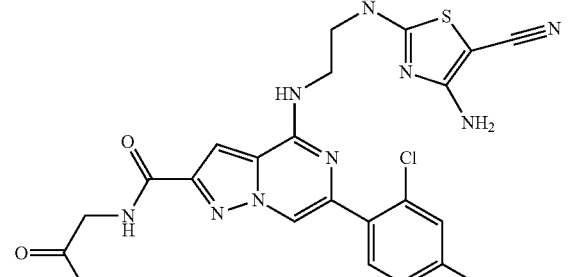 | LC/MS (method 6): R_t = 1.74 min, (m/z = 546 (M + H)+) |

-continued

| Ex. | Structure | Characterization |
|---|---|---|
| 25 | 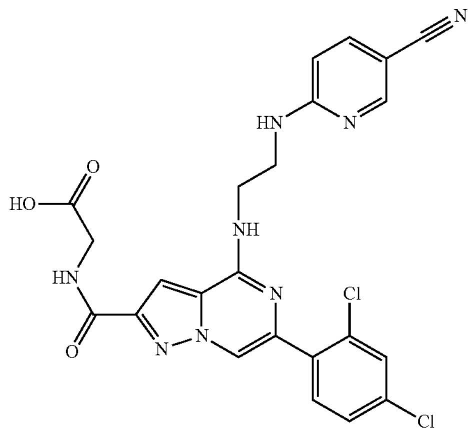 [SMILES: N#Cc1ccc(NCCNc2nc(-c3ccc(Cl)cc3Cl)cn3nc(C(=O)NCC(=O)O)cc23)nc1] | LC/MS (method 3): R$_t$ = 2.43 min, (m/z = 525 (M + H)$^+$) |
| 26 | 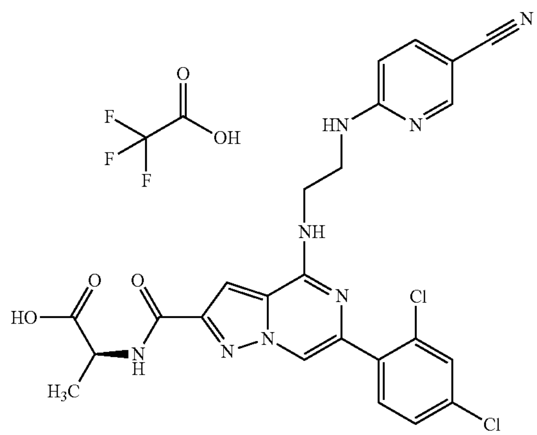 [SMILES: C[C@H](NC(=O)c1cc2c(NCCNc3ccc(C#N)cn3)nc(-c3ccc(Cl)cc3Cl)cn2n1)C(=O)O ; O=C(O)C(F)(F)F] | LC/MS (method 8): R$_t$ = 1.22 min, (m/z = 539 (M + H)$^+$) |
| 27 | 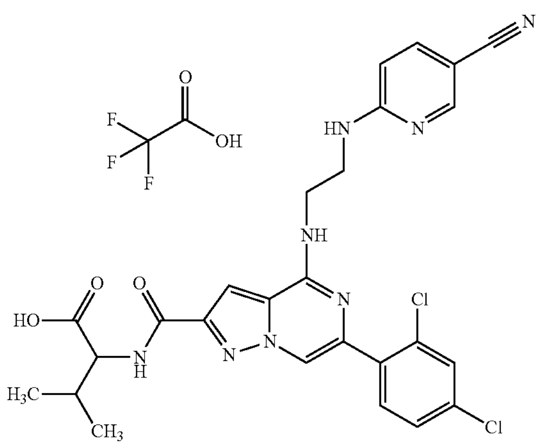 [SMILES: CC(C)C(NC(=O)c1cc2c(NCCNc3ccc(C#N)cn3)nc(-c3ccc(Cl)cc3Cl)cn2n1)C(=O)O ; O=C(O)C(F)(F)F] | LC/MS (method 6): R$_t$ = 2.17 min, (m/z = 567 (M + H)$^+$) |
| 28 | 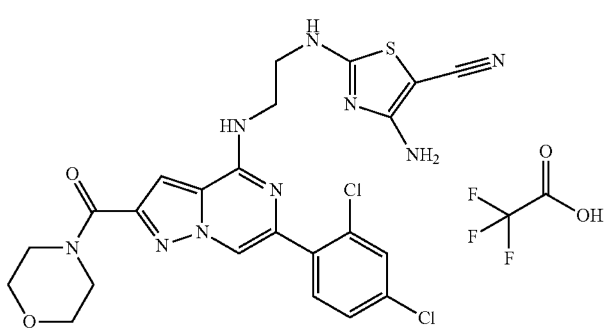 [SMILES: N#Cc1sc(NCCNc2nc(-c3ccc(Cl)cc3Cl)cn3nc(C(=O)N4CCOCC4)cc23)nc1N ; O=C(O)C(F)(F)F] | LC/MS (method 9): R$_t$ = 2.20 min, (m/z = 558 (M + H)$^+$) |

-continued
| Ex. | Structure | Characterization |
|---|---|---|
| 29 | 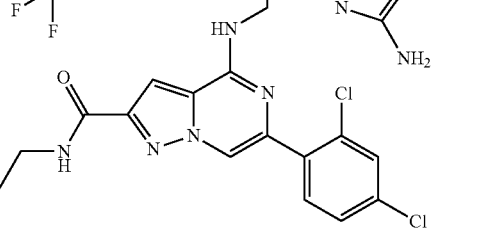 | LC/MS (method 3): $R_t$ = 1.57 min, (m/z = 559 (M + H)$^+$) |
| 30 | 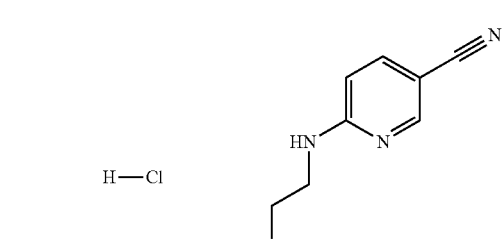 | LC/MS (method 3): $R_t$ = 1.63 min, (m/z = 580 (M + H)$^+$) |
| 31 | 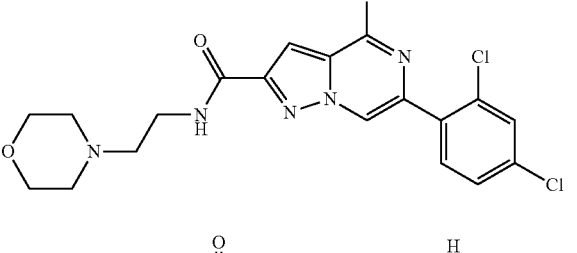 | LC/MS (method 6): $R_t$ = 1.24 min, (m/z = 614 (M + H)$^+$) |
| 32 | 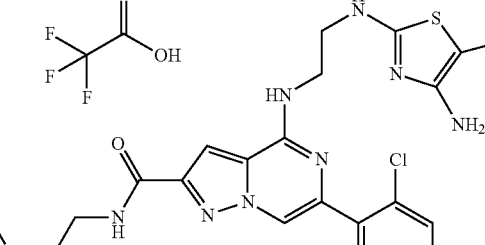 | LC/MS (method 8): $R_t$ = 1.22 min, (m/z = 467 (M + H)$^+$) |

| Ex. | Structure | Characterization |
|---|---|---|
| 33 | 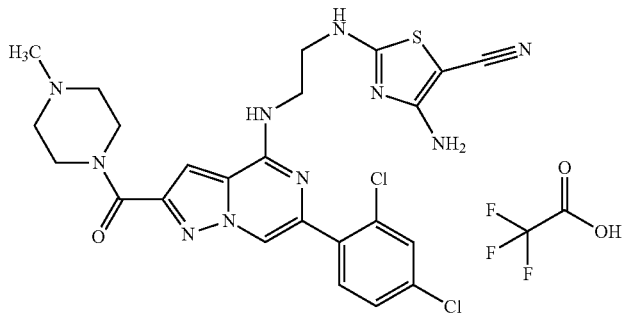 [SMILES: CN1CCN(C(=O)c2cc3c(NCCNc4nc(N)c(C#N)s4)nc(-c4ccc(Cl)cc4Cl)cn3n2)CC1 ; O=C(O)C(F)(F)F] | LC/MS (method 3): $R_t$ = 1.57 min, (m/z = 571 $(M + H)^+$) |

Example 34

1-{2-Amino-6-[(2-{[6-(2,4-dichlorophenyl)-2-(morpholin-4-ylmethyl)pyrazolo[1,5-a]pyrazin-4-yl]amino}ethyl)amino]pyridin-3-yl}-2,2,2-trifluoroethanone trifluoroacetate

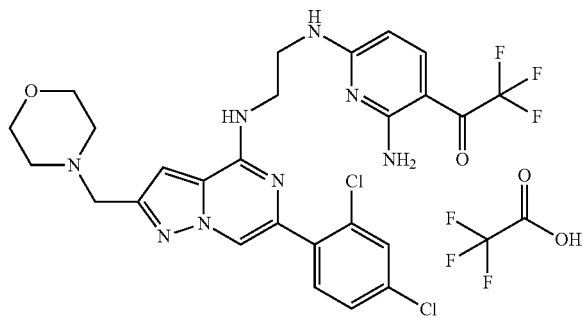

Analogously to the procedure described for Example 1, 60 mg (0.151 mmol) of 4-chloro-6-(2,4-dichlorophenyl)-2-(morpholin-4-ylmethyl)pyrazolo[1,5-a]pyrazine (Example 22A) gave, by reaction with 53 mg (0.181 mmol) of 1-{2-amino-6-[(2-aminoethyl)amino]pyridin-3-yl}-2,2,2-trifluoroethanone hydrochloride (Example 34A) and purification by preparative HPLC, 62 mg (57% of theory) of the product as a solid.

LCMS (method 3): $R_t$=1.84 min. (m/z=609 $(M+H)^+$)

$^1$H-NMR (400 MHz, DMSO-$d_6$): δ=10.41 (s, br, 1H), 8.54 (s, 1H), 8.26 (s, 1H), 8.10 (s, 2H), 7.73 (d, 1H), 7.68 (d, 1H), 7.54 (s, br, 1H), 7.48 (dd, 1H), 7.14 (s, 1H), 5.91 (d, 1H), 4.59 (s, 2H), 3.96 (m, 2H), 3.51-3.75 (m, 6H), 3.39 (m, 2H), 3.19 (m, 2H).

Analogously to the procedure described for the preparation of Example 1, the products below were synthesized from the corresponding chlorides by reaction with the appropriate amines.

| Ex. | Structure | Characterization |
|---|---|---|
| 35 | 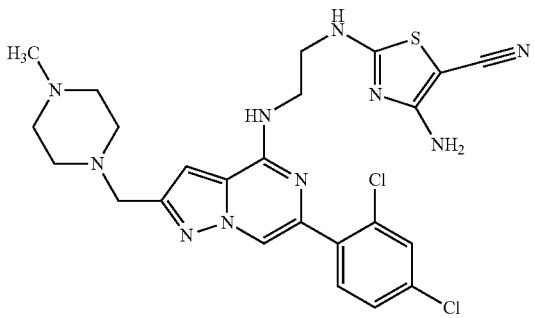 [SMILES: CN1CCN(Cc2cc3c(NCCNc4nc(N)c(C#N)s4)nc(-c4ccc(Cl)cc4Cl)cn3n2)CC1] | LC/MS (method 3): $R_t$ = 1.56 min, (m/z = 557 $(M + H)^+$) |

-continued
| Ex. | Structure | Characterization |
|---|---|---|
| 36 | 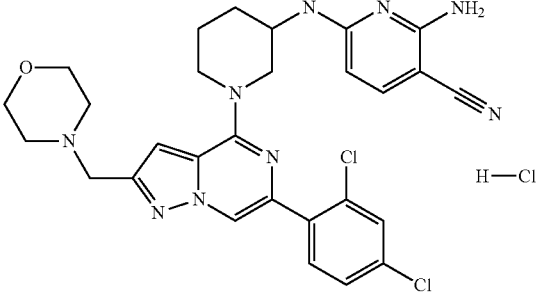 | LC/MS (method 3): R$_t$ = 1.74 min, (m/z = 578 (M + H)$^+$) |
| 37 | 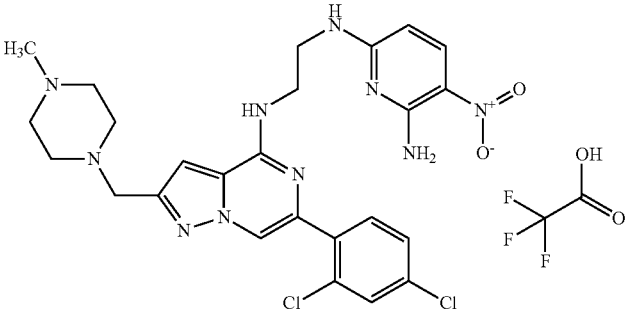 | LC/MS (method 8): R$_t$ = 0.98 min, (m/z = 571 (M + H)$^+$) |
| 38 | 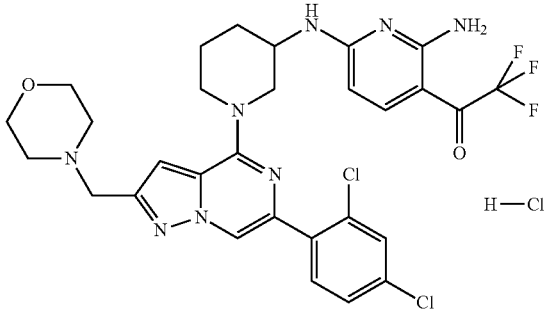 [SMILES: Nc1nc(NC2CCCN(c3nc(-c4ccc(Cl)cc4Cl)cn4nc(CN5CCOCC5)cc34)C2)ccc1C(=O)C(F)(F)F ; Cl] | LC/MS (method 6): R$_t$ = 1.73 min, (m/z = 649 (M + H)$^+$) |
| 39 | 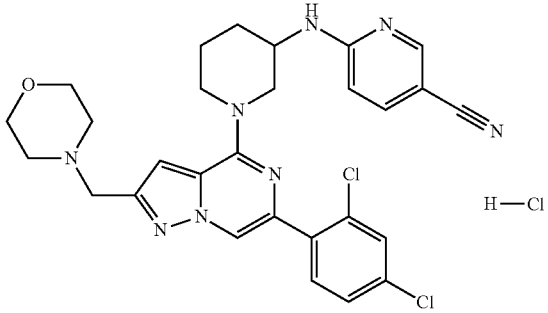 [SMILES: N#Cc1ccc(NC2CCCN(c3nc(-c4ccc(Cl)cc4Cl)cn4nc(CN5CCOCC5)cc34)C2)nc1 ; Cl] | LC/MS (method 3): R$_t$ = 1.84 min, (m/z = 563 (M + H)$^+$) |
| 40 | 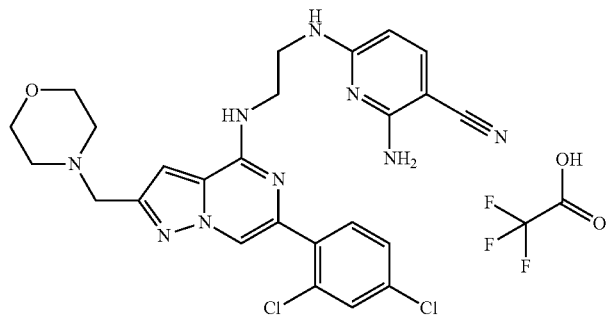 [SMILES: N#Cc1ccc(NCCNc2nc(-c3ccc(Cl)cc3Cl)cn3nc(CN4CCOCC4)cc23)nc1N ; O=C(O)C(F)(F)F] | LC/MS (method 3): R$_t$ = 1.59 min, (m/z = 538 (M + H)$^+$) |

Example 41

4-Amino-2-[(2-{[6-(2,4-dichlorophenyl)-2-(hydroxymethyl)pyrazolo[1,5-a]pyrazin-4-yl]amino}ethyl)amino]-1,3-thiazole-5-carbonitrile

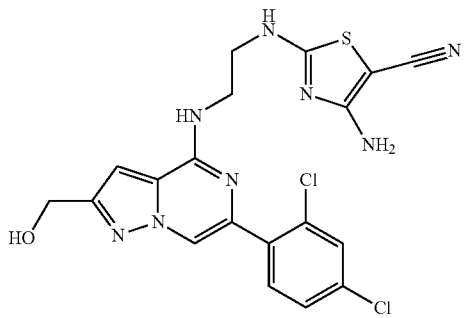 [SMILES: N#Cc1sc(NCCNc2nc(-c3ccc(Cl)cc3Cl)cn3nc(CO)cc23)nc1N]

100 mg (0.184 mmol) of ethyl 4-({2-[(4-amino-5-cyano-1,3-thiazol-2-yl)amino]ethyl}amino)-6-(2,4-dichlorophenyl)pyrazolo[1,5-a]pyrazine-2-carboxylate (Example 11) were dissolved in 10 ml of THF, and 0.276 ml (0.276 mmol) of a solution of lithium aluminum hydride (1 mol/l) in THF was added dropwise at RT. The mixture was stirred for 2 h, and after complete conversion first methanol was added, and then the pH was adjusted to pH=5 using dilute hydrochloric acid. The mixture was extracted repeatedly with ethyl acetate. Removal of the solvent and purification by preparative HPLC gave 61 mg (64% of theory) of the product as a solid.

LCMS (method 8): $R_t$=1.10 min. (m/z=475 (M+H)$^+$)

$^1$H-NMR (400 MHz, DMSO-d$_6$): δ=8.50 (t, 1H), 8.15 (s, 1H), 7.91 (t, 1H), 7.70 (d, 1H), 7.68 (d, 1H), 7.51 (dd, 1H), 6.95 (s, 2H), 6.69 (s, br, 2H), 4.62 (s, 2H), 3.64 (dd, 2H), 3.51 (m, 2H).

Example 42

4-Amino-2-[(2-{[6-(2,4-dichlorophenyl)-2-(hydroxymethyl)pyrazolo[1,5-a]pyrazin-4-yl]amino}ethyl)amino]-1,3-thiazole-5-carbonitrile

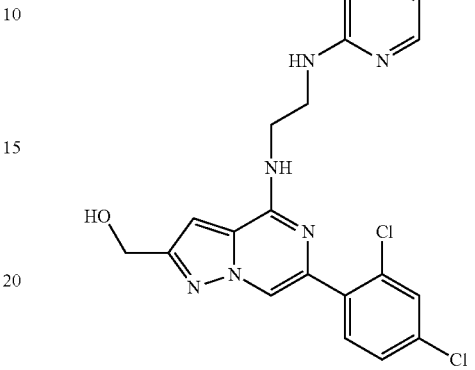

100 mg (0.184 mmol) of ethyl 4-({2-[(4-amino-5-cyano-1,3-thiazol-2-yl)amino]ethyl}amino)-6-(2,4-dichlorophenyl)pyrazolo[1,5-a]pyrazine-2-carboxylate (Example 3) were dissolved in 10 ml of THF, and 0.276 ml (0.276 mmol) of a solution of lithium aluminum hydride (1 mol/l) in THF was added dropwise at RT. The mixture was stirred for 2 h, and after complete conversion first methanol was added, and then the pH was adjusted to pH=5 using dilute hydrochloric acid. The mixture was extracted repeatedly with ethyl acetate. Removal of the solvent and purification by preparative HPLC gave 61 mg (64% of theory) of the product as a solid.

LCMS (method 8): $R_t$=1.10 min. (m/z=475 (M+H)$^+$)

$^1$H-NMR (400 MHz, DMSO-d$_6$): δ=8.50 (t, 1H), 8.15 (s, 1H), 7.91 (t, 1H), 7.70 (d, 1H), 7.68 (d, 1H), 7.51 (dd, 1H), 6.95 (s, 2H), 6.69 (s, br, 2H), 4.62 (s, 2H), 3.64 (dd, 2H), 3.51 (m, 2H).

Analogously to the procedure described for Example 2, the products below were obtained from 6-({2-[(6-bromoimidazo[1,2-a]pyrazin-8-yl)amino]ethyl}amino)pyridine-3-carbonitrile (Example 23A) by palladium-catalyzed reaction with the corresponding boronic acids.

| Ex. | Structure | Characterization |
| --- | --- | --- |
| 43 | 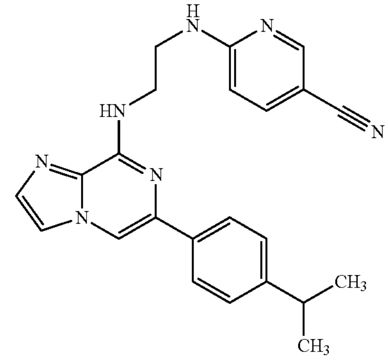 [SMILES: CC(C)c1ccc(-c2cn3ccnc3c(NCCNc3ccc(C#N)cn3)n2)cc1] | LC/MS (method 8): $R_t$ = 1.32 min, (m/z = 398 (M + H)$^+$) |

| Ex. | Structure | Characterization |
|---|---|---|
| 44 | 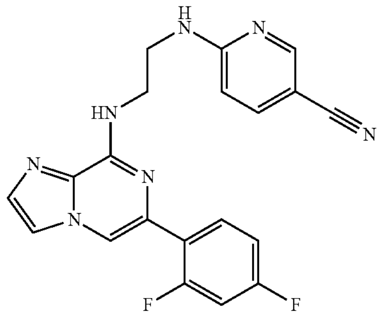 [SMILES: N#Cc1ccc(NCCNc2nc(-c3ccc(F)cc3F)cn3ccnc23)nc1] | LC/MS (method 10): $R_t$ = 2.02 min, (m/z = 392 (M + H)$^+$) |
| 45 | 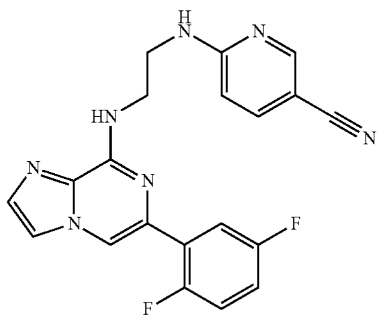 [SMILES: N#Cc1ccc(NCCNc2nc(-c3cc(F)ccc3F)cn3ccnc23)nc1] | LC/MS (method 11): $R_t$ = 2.04 min, (m/z = 392 (M + H)$^+$) |
| 46 | 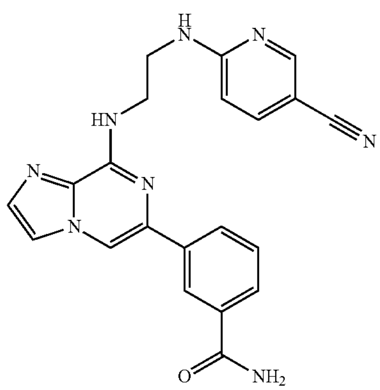 [SMILES: N#Cc1ccc(NCCNc2nc(-c3cccc(C(N)=O)c3)cn3ccnc23)nc1] | LC/MS (method 10): $R_t$ = 1.43 min, (m/z = 399 (M + H)$^+$) |
| 47 | 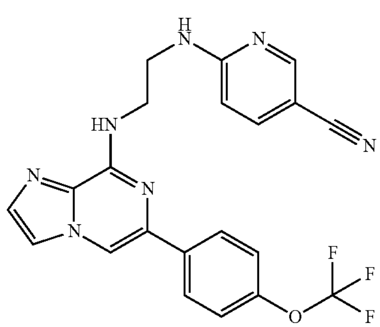 [SMILES: N#Cc1ccc(NCCNc2nc(-c3ccc(OC(F)(F)F)cc3)cn3ccnc23)nc1] | LC/MS (method 11): Rt = 2.16 min, (m/z = 440 (M + H)$^+$) |

-continued
| Ex. | Structure | Characterization |
|---|---|---|
| 48 | 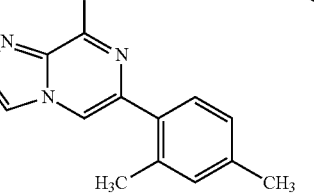 | LC/MS (method 11): $R_t$ = 1.66 min, (m/z = 384 (M + H)$^+$) |
| 49 | 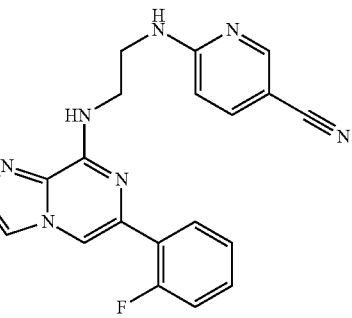 | LC/MS (method 11): $R_t$ = 1.92 min, (m/z = 374 (M + H)$^+$) |
| 50 | 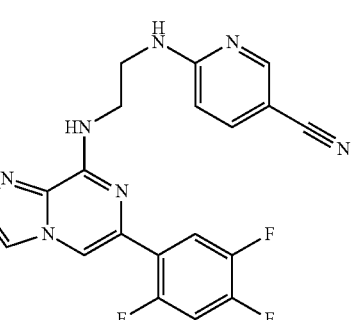 | LC/MS (method 10): $R_t$ = 2.11 min, (m/z = 410 (M + H)$^+$) |
| 51 | 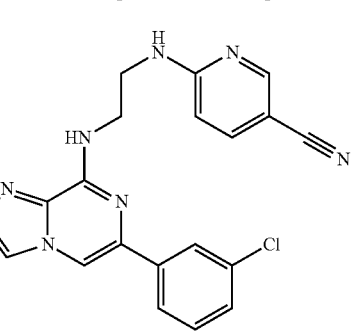 | LC/MS (method 11): $R_t$ = 2.08 min, (m/z = 390 (M + H)$^+$) |
| 52 | 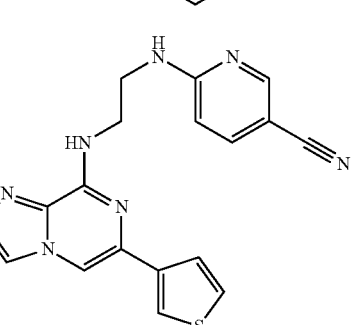 | LC/MS (method 10): $R_t$ = 1.82 min, (m/z = 362 (M + H)$^+$) |

Example 53

6-[(2-{[6-(2,4-Dichlorophenyl)-2-(morpholin-4-ylmethyl)pyrazolo[1,5-a]pyrazin-4-yl]amino}ethyl)amino]nicotinonitrile hydrochloride

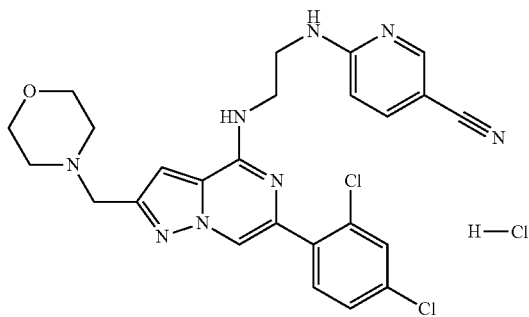 [SMILES: N#Cc1ccc(NCCNc2nc(-c3ccc(Cl)cc3Cl)cn3nc(CN4CCOCC4)cc23)nc1 ; Cl]

30 mg (0.066 mmol) of 6-[(2-{[6-(2,4-dichlorophenyl)-2-formylpyrazolo[1,5-a]pyrazin-4-yl]amino}ethyl)amino]pyridine-3-carbonitrile (Example 54A) were dissolved in 1 ml of methanol, and 11.6 mg (0.133 mmol) of morpholine, 4 Å molecular sieve and 11.9 mg (0.199 mmol) of acetic acid were added. Finally, 8.3 mg (0.133 mmol) of sodium cyanoborohydride were added and the mixture was stirred at RT for 1 h. The crude mixture was acidified with 2N hydrochloric acid and purified by preparative HPLC. Lyophilization gave 25 mg (58% of theory) of the product as a solid.

LCMS (method 3): $R_t$=1.74 min. (m/z=523 (M+H)$^+$).

$^1$H-NMR (400 MHz, DMSO-d$_6$): δ=11.0 (br, 1H), 8.39 (d, 1H), 8.27 (m, 1H), 8.23 (s, 1H), 7.87 (br, 1H), 7.74 (d, 1H), 7.67 (d, 1H), 7.61 (m, 1H), 7.54 (dd, 1H), 7.23 (s, 1H), 6.57 (m, 1H), 4.57 (s, 2H), 3.95 (m, 4H), 3.62 (m, 4H), 3.49 (m, 2H), 3.18 (m, 2H).

Analogously to the procedure described for the preparation of Example 53, the products below were obtained by reductive amination starting with 6-[(2-{[6-(2,4-dichlorophenyl)-2-formylpyrazolo[1,5-a]pyrazin-4-yl]amino}ethyl)amino]pyridine-3-carbonitrile (Example 54A) or the corresponding amines.

| Ex. | Structure | Characterization |
| --- | --- | --- |
| 54 | 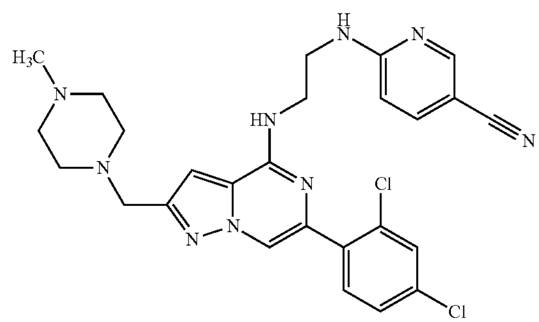 [SMILES: CN1CCN(Cc2cc3c(NCCNc4ccc(C#N)cn4)nc(-c4ccc(Cl)cc4Cl)cn3n2)CC1] | LCMS (method 9): $R_t$ = 1.72 min. (m/z = 536 (M + H)$^+$). $^1$H-NMR (400 MHz, DMSO-d$_6$): δ = 8.40 (d, 1H), 8.23 (s, 1H), 8.18 (m, 1H), 7.86 (br, 1H), 7.74 (d, 1H), 7.66 (d, 1H), 7.61 (m, 1H), 7.52 (dd, 1H), 7.13 (m, 1H), 6.50 (m, 1H), 3.50 (m, 2H), 3.20 (m, 2H), 2.81 (s, 3H). Other signals overlap with the signal for water. |
| 55 | 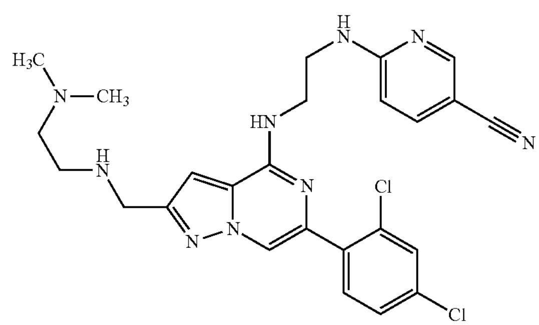 [SMILES: CN(C)CCNCc1cc2c(NCCNc3ccc(C#N)cn3)nc(-c3ccc(Cl)cc3Cl)cn2n1] | LCMS (method 9): $R_t$ = 1.50 min. (m/z = 524 (M + H)$^+$). $^1$H-NMR (400 MHz, DMSO-d$_6$): δ = 10.74 (br, 1H), 9.83 (br, 1H), 8.42 (d, 1H), 8.29 (m, 1H), 8.23 (s, 1H), 7.94 (br, 1H), 7.75 (d, 1H), 7.69 (d, 1H), 7.54 (dd, 1H), 7.20 (s, 1H), 6.56 (m, 1H), 4.45 (m, 2H), 3.66 (m, 4H), 3.47 (m, 4H), 2.85 (d, 3H). |
| 56 | 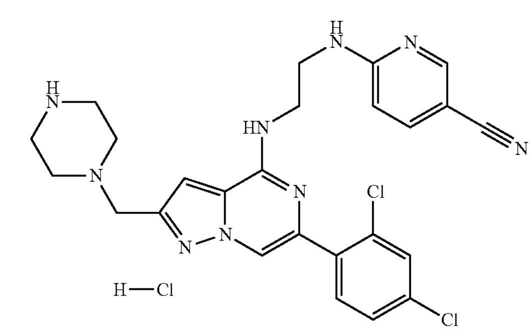 | LCMS (method 9): $R_t$ = 1.71 min. (m/z = 522 (M + H)$^+$). $^1$H-NMR (400 MHz, DMSO-d$_6$): δ = 11.75 (br, 1H), 9.25 (br, 2H), 8.40 (d, 1H), 8.23 (s, 2H), 7.84 (br, 1H), 7.74 (d, 1H), 7.66 (d, 1H), 7.60 (d, 1H), 7.53 (dd, 1H), 7.21 (s, 1H), 6.57 (m, 1H), 4.50 (br s, 2H). Other signals overlap with the signal for water. |

-continued

| Ex. | Structure | Characterization |
|---|---|---|
| 57 | 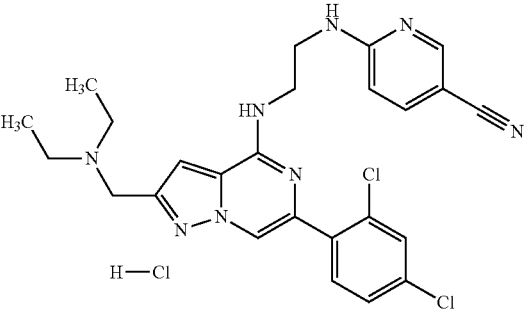 | LCMS (method 9): $R_t$ = 1.83 min. (m/z = 509 (M + H)$^+$). $^1$H-NMR (400 MHz, DMSO-d$_6$): δ = 10.25 (br, 1H), 8.39 (d, 1H), 8.24 (s, 1H), 8.22 (m, 1H), 7.87 (br, 1H), 7.74 (d, 1H), 7.68 (d, 1H), 7.61 (br d, 1H), 7.53 (dd, 1H), 7.24 (s, 1H), 6.56 (m, 1H), 4.54 (m, 2H), 3.65 (m, 4H), 3.13 (m, 4H), 1.31 (t, 6H). |
| 58 | 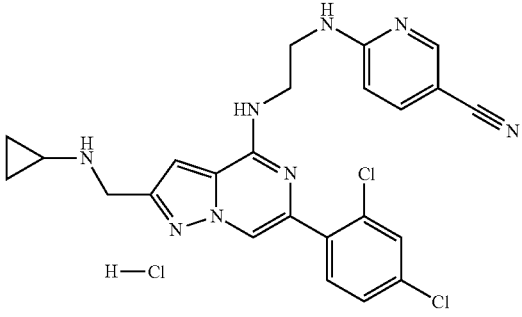 | LCMS (method 9): $R_t$ = 1.79 min. (m/z = 493 (M + H)$^+$). $^1$H-NMR (400 MHz, DMSO-d$_6$): δ = 8.37 (d, 1H), 8.13 (s, 1H), 7.85 (m, 1H), 7.76 (br, 1H), 7.72 (d, 1H), 7.68 (d, 1H), 7.59 (d, 1H), 7.51 (dd, 1H), 6.90 (s, 1H), 6.54 (m, 1H), 3.89 (s, 2H), 3.64 (m, 4H), 2.15 (m, 1H), 0.37 (m, 2H), 0.28 (m, 2H). |
| 59 | 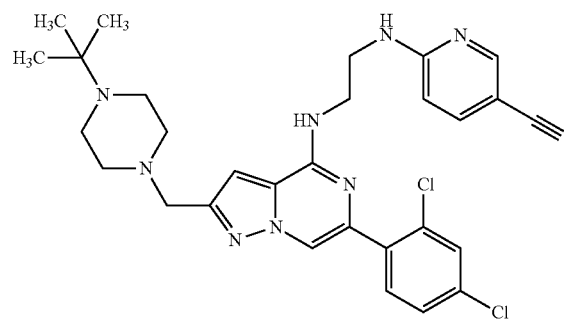 | LCMS (method 9): $R_t$ = 1.94 min. (m/z = 578 (M + H)$^+$). $^1$H-NMR (400 MHz, DMSO-d$_6$): δ = 11.25 (br, 1H), 8.39 (d, 1H), 8.27 (m, 1H), 8.23 (s, 1H), 7.89 (br, 1H), 7.75 (d, 1H), 7.68 (d, 1H), 7.62 (d, 1H), 7.54 (dd, 1H), 7.24 (s, 1H), 6.57 (m, 1H), 4.58 (m, 2H), 3.68 (m, 8H), 3.45 (m, 4H), 1.36 (s, 9H). |
| 60 | 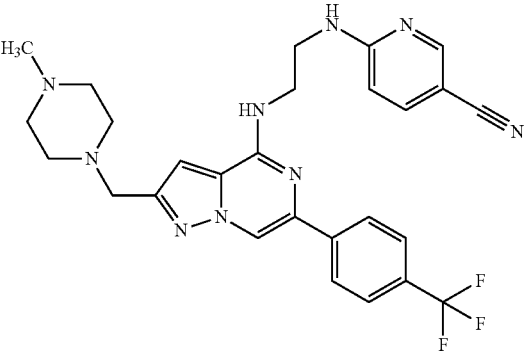 [SMILES: CN1CCN(Cc2cc3c(NCCNc4ccc(C#N)cn4)nc(-c4ccc(C(F)(F)F)cc4)cn3n2)CC1] | LCMS (method 8): $R_t$ = 1.04 min. (m/z = 536 (M + H)$^+$). $^1$H-NMR (400 MHz, DMSO-d$_6$): δ = 8.73 (s, 1H), 8.45 (s, 1H), 8.25 (d, 2H), 8.16 (br, 1H), 7.91 (br, 1H), 7.77 (d, 2H), 7.64 (m, 1H), 7.14 (m, 1H), 6.56 (m, 1H), 2.81 (s, 3H). Other signals overlap with the signal for water. |

| Ex. | Structure | Characterization |
|---|---|---|
| 61 | 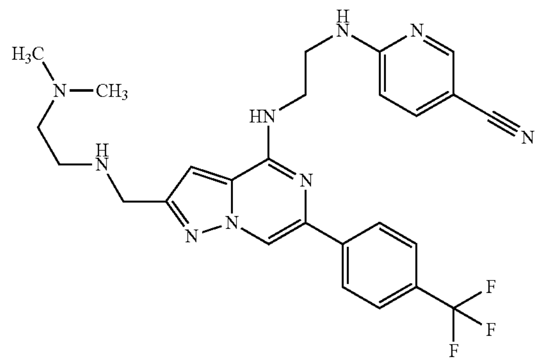 [SMILES: CN(C)CCNCc1cc2c(NCCNc3ccc(C#N)cn3)nc(-c3ccc(C(F)(F)F)cc3)cn2n1] | LCMS (method 8): $R_t = 0.95$ min. (m/z = 524 (M + H)$^+$). $^1$H-NMR (400 MHz, DMSO-d$_6$): δ = 10.61 (br, 1H), 9.75 (br, 2H), 8.70 (s, 1H), 8.45 (m, 1H), 8.26 (d, 2H), 8.22 (m, 1H), 7.90 7.79 (d, 2H), 7.64 (d, 1H), 7.17 (s, 1H), 6.54 (m, 1H), 4.47 (m, 2H), 3.79 (m, 2H), 2.86 (d, 6H). Other signals overlap with the signal for water. |
| 62 | 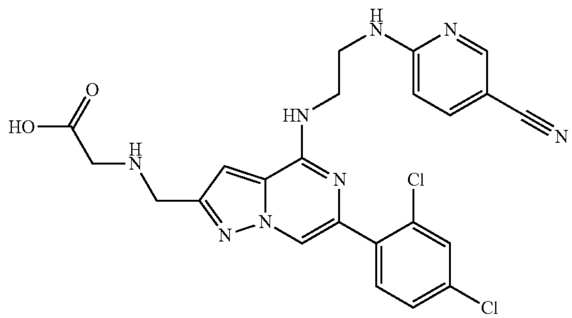 [SMILES: N#Cc1ccc(NCCNc2nc(-c3ccc(Cl)cc3Cl)cn3nc(CNCC(=O)O)cc23)nc1] | LCMS (method 9): $R_t = 1.84$ min. (m/z = 511 (M + H)$^+$). 1H-NMR (400 MHz, DMSO-d$_6$): δ = 9.67 (br, 2H), 8.409 (d, 1H), 8.25 (m, 1H), 8.23 (s, 1H), 7.92 (br, 1H), 7.74 (d, 1H), 7.68 (d, 1H), 7.63 (d, 1H), 7.54 (dd, 2H), 7.16 (s, 1H), 6.57 (m, 1H), 4.41 (m, 2H), 3.96 (m, 2H), 3.64 (m, 4H). |

Example 63

4-({2-[(4-Amino-5-cyano-1,3-thiazol-2-yl)amino]ethyl}amino)-6-(2,4-dichlorophenyl)pyrazolo[1,5-a]pyrazine-2-carbonitrile

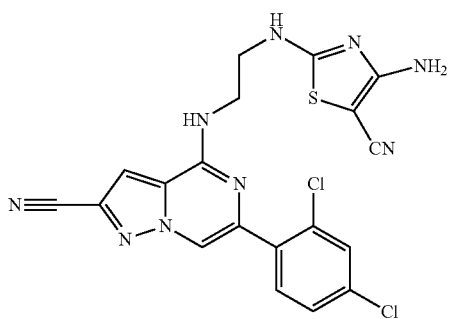 [SMILES: N#Cc1cc2c(NCCNc3nc(N)c(C#N)s3)nc(-c3ccc(Cl)cc3Cl)cn2n1]

Analogously to the procedure described for Example 3, 60 mg (0.19 mmol) of 4-chloro-6-(2,4-dichlorophenyl)pyrazolo[1,5-a]pyrazine-2-carbonitrile (Example 57A) gave, by reaction with 61.1 mg (0.28 mmol) of 4-amino-2-[(2-aminoethyl)amino]-1,3-thiazole-5-carbonitrile dihydrochloride (Example 8A) and purification by preparative HPLC, 24 mg (28% of theory) of the product as a solid.

LCMS (method 3): $R_t$=2.63 min. (m/z=470 (M+H)$^+$).

$^1$H-NMR (400 MHz, DMSO-d$_6$): δ=8.50 (t, 1H), 8.37 (s, 1H), 8.35 (t, 1H), 7.76 (d, 1H), 7.66 (m, 2H), 7.54 (dd, 1H), 6.69 (br, 2H), 3.78 (m, 2H), 3.53 (m, 2H).

Example 64

4-({2-[(5-Cyanopyridin-2-yl)amino]ethyl}amino)-6-(2,4-dichlorophenyl)pyrazolo[1,5-a]pyrazine-2-carbonitrile

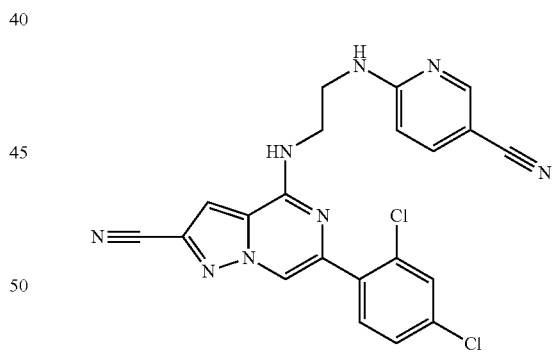

Analogously to the procedure described for Example 3, 60 mg (0.19 mmol) of 4-chloro-6-(2,4-dichlorophenyl)pyrazolo[1,5-a]pyrazine-2-carbonitrile (Example 57A) gave, by reaction with 61.1 mg (0.28 mmol) of 6-[(2-aminoethyl)amino]pyridine-3-carbonitrile dihydrochloride (Example 2A) and purification by preparative HPLC, 42 mg (50% of theory) of the product as a solid.

LCMS (method 3): $R_t$=2.82 min. (m/z=449 (M+H)$^+$).

$^1$H-NMR (400 MHz, DMSO-d$_6$): δ=8.34 (m, 3H), 7.76 (m, 2H), 7.67 (m, 2H), 7.60 (dd, 1H), 7.54 (dd, 1H), 6.51 (m, 1H), 3.69-3.57 (m, 4H).

B) ASSESSMENT OF THE PHYSIOLOGICAL ACTIVITY

The suitability of the compounds according to the invention for treating hematological disorders can be shown in the following assay systems:

In Vitro Assay

The inhibitory activity of active substances is determined in a biochemical assay. The ingredients required for this purpose are mixed in a black 384-well microtiter plate with transparent base (from Greiner, catalog number 781092). The requirements in this connection for each well of the 384-well microtiter plate are 5 nM GSK3β (from Upstate, catalog number xy), 40 µM GSK3β substrate GSM (sequence H-RRRPASVPPSPSLSRHS-(pS)-HQRR, from Upstate, catalog number 2-533), 30 µM nicotinamide adenine dinucleotide NADH (Roche Diagnostics, catalog number 10107735), 50 µM adenosine triphosphate ATP (from Sigma, catalog number A7966) and 2 mM phosphoenolpyruvate (from Roche, catalog number 128112). The required reaction buffer in which the biochemical reaction takes place consists of 50 mM Trizma hydrochloride Tris-HCl pH: 7.5 (from Sigma, catalog number T3253), 5 mM magnesium chloride $MgCl_2$ (from Sigma, catalog number M8266), 0.2 mM DL-dithiothreitol DTT (from Sigma, catalog number D9779), 2 mM ethylenediaminetetraacetic acid EDTA (from Sigma, catalog number E6758), 0.01% Triton X-100 (from Sigma, catalog number T8787) and 0.05% bovine serum albumin BSA (from Sigma, catalog number B4287).

Active substances are dissolved in dimethyl sulfoxide DMSO (from Sigma, catalog number D8418) in a concentration of 10 mM. Active substances are added in serial concentrations of 10 µM, 1 µM, 0.1 µM, 0.01 µM, 0.001 µM, 0.0001 µM, 0.00001 µM, 0.000001 µM to the mixtures of the biochemical reaction. As control, dimethyl sulfoxide is added instead of substance in a final concentration of 0.1%.

The reaction is incubated at 30° C. for 2 hours and then the resulting fluorescence is measured in a Tecan Safire-XFLUOR4 instrument, version V4.50 (serial number 12901300283) with the specifications: measurement mode—fluorescence measured from below, extinction wavelength 340 nm, emission wavelength 465 nm, slit width extinction 5 nm, slit width emission 5 nm, gain mode 120, delay 0 µs, number of light flashes per measurement 3, and an integration time of 40 µs.

The GSK3β activity is measured in fluorescence units, with the values of uninhibited kinase being set equal to 100% and those of completely inhibited kinase being set equal to 0%. The activity of the active substances is calculated in relation to these 0% and 100%.

Table A shows representative in vitro activity data for the compounds according to the invention:

TABLE A

| Example No. | $IC_{50}$ [nM] |
|---|---|
| 2 | 16 |
| 4 | 21 |
| 5 | 30 |
| 9 | 310 |
| 17 | 8 |
| 19 | 3 |
| 24 | 5 |
| 58 | 80 |

CD34+ Proliferation Assays for Testing GSK3β Inhibitors

Adult hematopoietic stem cells are characterized by the specific expression of membrane-associated proteins. These surface markers are provided with an appropriate number appropriate for their molecular weight. This class also includes the molecule which is referred to as CD34 and which serves for the identification, characterization and isolation of adult hematopoietic stem cells. These stem cells can moreover be isolated from bone marrow, peripheral blood or umbilical cord blood. These cells have limited viability in in vitro cultures but can be stimulated to proliferation and differentiation by various additions to the culture medium. CD34-positive cells are used here in order to test the influence of substances on the activity of glycogen synthase kinase 3. For this purpose, in a first step, mononuclear cells are isolated from umbilical cord blood by differential centrifugation steps.

For this purpose, umbilical cord blood is diluted 1:4 with phosphate-buffered saline solution. 50 milliliter centrifugation vessels are charged with 17 milliliters of Ficoll (density 1.077, Ficoll Paque Plus; Pharmacia, catalog number 17-1440-02). 30 milliliters of the 1:4 diluted umbilical cord blood are layered thereon and then centrifuged at 400×g at room temperature for 30 minutes. The brakes of the centrifuge are disengaged during this. Owing to the centrifugation, the mononuclear cells collect in the interphase. This is removed with the aid of a 30 milliliter pipette and transferred into a new 50 milliliter centrifugation vessel, and the volume is then made up to 30 ml with phosphate-buffered saline solution. These cells are centrifuged at 300×g with the brake engaged at room temperature for 10 minutes. The supernatant is discarded and the resulting cell pellet is resuspended in 30 milliliters of phosphate-buffered saline solution. These cells are again centrifuged at 200×g with brake engaged at 20° C. for 15 minutes.

To isolate the CD34-positive cells, the enriched mononuclear cells are resuspended in a concentration of $1 \times 10^8$ cells per 300 microliters of MACS buffer (0.5% endotoxin-free bovine serum albumin in phosphate-buffered saline solution). 100 microliters of FCR blocking reagent (Miltenyi Biotec, catalog number 130-046-702) and 100 microliters of CD34 microbeads (Miltenyi Biotec, catalog number 130-046-702) are added. This suspension is incubated at 4° C. for 30 minutes. The cells are then diluted with 20 times the volume of MACS buffer and centrifuged at 300×g for 10 minutes. The supernatant is discarded and the cells are resuspended in 500 microliters of MACS buffer. The cells treated in this way are loaded onto an LS column (Miltenyi Biotec, catalog number 130-042-401) and purified using a Midi MACS magnet (Miltenyi Biotec, catalog number 130-042-303).

The number of CD34-positive cells is determined by counting the cells using a Neubauer chamber. The purity of the cells is determined by standard protocols using the fluorescent activated cell sorting method (Becton Dickinson, BD FACS™ Sample Prep Assistant SPAII Upgrade Kit, catalog number 337642).

To determine the influence of modulating the GSK3 activity, CD34-positive cells are incubated in a 96-well microtiter plate at 37° C. and 5% carbon dioxide for 7 days and then the proliferation rates are determined on the basis of the cell counts.

For this purpose, 5000 CD34-positive cells are taken up in 100 microliters of IMDM medium (Life Technology, catalog number 12440-046), 10% fetal calf serum (Life Technology, catalog number 10082-139) and 20 nanograms per milliliter of stem cell factor (R&D, catalog number 255-SC-010) in each well of a 96 U-bottom well microtiter plate (Greiner Bio-One, catalog number 650 180). In addition, the cells are also mixed with various concentrations of substances dissolved in dimethyl sulfoxide (Sigma Aldrich, catalog number D5879-1L). This entails 4 wells in each case with the stated cell count of 5000 CD34-positive cells per well being provided with 10 micromol, 4 wells with 5 micromol, 4 wells with 2.5 micromol, 4 wells with 1.25 micromol, 4 wells with 0.625 micromol, 4 wells with 0.3125 micromol, 4 wells with 0.156 micromol, 4 wells with 0.078 micromol and as control 4 wells with 0.1% dimethyl sulfoxide as final concentration.

These cells treated in this way are incubated in a cell culture incubator at 37° C. and 5% carbon dioxide for 7 days. The proliferation rate is determined by renewed counting of the cells using a Neubauer counting chamber, with the cells provided only with the stem cell factor being set as 100% value, and all other values being related to this value.

In Vivo Assay

The investigations of the in vivo effect of the compounds according to the invention take place using 6-week old male C57BL/6 mice (Charles River, Sulzfeld, Germany) weighing 18-22 g. These animals are kept appropriate for the species with 12-hour light and dark cycles under constant climatic conditions and with water and mouse feed ad libitum. The concentrations of chemotherapeutics used are administered to the animals in accordance with the manufacturer's statements by intraperitoneal (i.p.) injections in the caudal third of the abdomen. The same procedure is applied to the substances relevant to the invention. Blood samples are taken from the retrobulbar venous plexus using Pasteur pipettes. The number of neutrophilic granulocytes is determined completely automatically using flow cytometry systems.

CYP Inhibition Test

The ability of substances to inhibit CYP1A2, CYP2C8, CYP2C9, CYP2D6 and CYP3A4 in humans is examined using pooled human liver microsomes as enzyme source in the presence of standard substrates (see below) which form CYP isoform-specific metabolites. The inhibitory effects are studied at six different concentrations of the test compounds (1.5, 3.1, 6.3, 12.5, 25 and 50 $\mu$M) and compared to the extent of the CYP isoform-specific metabolite formation of the standard substrates in the absence of test compounds, and the corresponding $IC_{50}$ values are calculated. A standard inhibitor which specifically inhibits a single CYP isoform serves as control of the results obtained.

Procedure:

The incubation of phenacetin, amodiaquine, diclofenac, dextromethorphan or midazolam with human liver microsomes in the presence of in each case six different concentrations of a test compound (as potential inhibitor) is carried out on a workstation (Tecan, Genesis, Crailsheim, Germany). Standard incubation mixtures comprise 1.3 mM NADP, 3.3 mM $MgCl_2 \times 6H_2O$, 3.3 mM glucose 6-phosphate, glucose 6-phosphate dehydrogenase (0.4 U/ml) and 100 mM phosphate buffer (pH 7.4) in a total volume of 200 $\mu$l. Test compounds are preferably dissolved in acetonitrile. 96-Well plates are incubated for a defined period of time at 37° C. with pooled human liver microsomes. The reactions are stopped by addition of 100 $\mu$l of acetonitrile comprising a suitable internal standard. Precipitated proteins are removed by centrifugation, and the supernatants are combined and analysed by LC-MS/MS.

Determination of the Solubility

Reagents Required:

PBS buffer pH 6.5: 61.86 g of sodium chloride p.a. (for example from Merck, Art. No. 1.06404.1000), 39.54 g of sodium dihydrogen phosphate p.a. (for example from Merck, Art. No. 1.06346.1000) and 83.35 g of 1 N sodium hydroxide solution (for example from Bernd Kraft GmbH, Art. No. 01030.4000) are weighed out into a 1 liter measuring flask and made up with water, and the mixture is stirred for about 1 hour. 500 ml of this solution are transferred into a 5 liter measuring flask and made up with water. The pH is adjusted to 6.5 using 1 N sodium hydroxide solution.

Dimethyl sulfoxide (for example from Baker, Art. No. 7157.2500)

Distilled water

Acetonitrile Chromasolv (for example Riedel-de Haen Art. No. 34851)

50% strength formic acid p.a. (for example Fluka Art. No. 09676)

Preparation of the Starting Solution:

At least 1.5 mg of the test substance are weighed out accurately into a Wide Mouth 10 mm Screw V-Vial (from Glastechnik Gräfenroda GmbH, Art. No. 8004-WM-H/V 15$\mu$) with fitting screw cap and septum, dimethyl sulfoxide is added to give a concentration of 50 mg/ml and the mixture is vortexed for 30 minutes.

Preparation of the Calibration Solutions:

The required pipetting steps are carried out in a 1.2 ml Deep Well Plate (DWP) with 96 wells (e.g. HJ-Bioanalytik GmbH Art. No. 850289) using a liquid handling robot. The solvent used is a mixture of acetonitrile Chromasolv/distilled water 8:2.

Preparation of the starting solution for calibration solutions (stock solution): 833 $\mu$l of the solvent mixture are added to 10 $\mu$l of the initial solution (concentration=600 $\mu$g/ml), and the mixture is homogenized. For each test substance, 1:100 dilutions are prepared in separate DWPs, and the dilutions for their part are homogenized. One of the 1:100 dilutions is used for preparing the calibration solutions, the second dilution is used for optimizing the MS/MS parameter.

Calibration solution 5 (600 ng/ml): 270 $\mu$l of solvent mixture are added to 30 $\mu$l of the stock solution, and the mixture is homogenized.

Calibration solution 4 (60 ng/ml): 270 $\mu$l of solvent mixture are added to 30 $\mu$l of calibration solution 5, and the mixture is homogenized.

Calibration solution 3 (12 ng/ml): 400 $\mu$l of solvent mixture are added to 100 $\mu$l of calibration solution 4, and the mixture is homogenized.

Calibration solution 2 (1.2 ng/ml): 270 $\mu$l of solvent mixture are added to 30 $\mu$l of calibration solution 3, and the mixture is homogenized.

Calibration solution 1 (0.6 ng/ml): 150 $\mu$l of solvent mixture are added to 150 $\mu$l of calibration solution 2, and the mixture is homogenized.

Preparation of the Sample Solutions:

The required pipetting steps are carried out in a 1.2 ml DWP with 96 wells (e.g. HJ-Bioanalytik GmbH Art. No. 850289) using a liquid handling robot.

1000 $\mu$l of PBS buffer pH 6.5 are added to 10.1 $\mu$l of the stock solution.

Procedure:

The required pipetting steps are carried out in a 1.2 ml DWP with 96 wells (e.g. HJ-Bioanalytik GmbH Art. No. 850289) using a liquid handling robot.

Using a temperature-adjustable shaker (e.g. from Eppendorf Thermomixer comfort Art. No. 5355 000.011), the sample solutions prepared in this manner are shaken at 20° C. and 1400 rpm for 24 hours. From these solutions, in each case 180 $\mu$l are removed and transferred into Beckman polyallomer centrifuge tubes (Art. No. 343621). These solutions are centrifuged at about 223 000×g for 1 hour (e.g. from Beckman Optima L-90K Ultracentrifuge with type 42.2 Ti rotor at 42 000 rpm). From each sample solution, 100 μl of the supernatant are removed and diluted 1:10 and 1:1000 with PBS buffer 6.5.
Analysis:

The samples are analysed by HPLC/MS-MS. Quantification is carried out using a five point calibration curve of the test compound. The solubility is expressed in mg/l. Analysis sequence: 1) blank (solvent mixture); 2) calibration solution 0.6 ng/ml; 3) calibration solution 1.2 ng/ml; 4) calibration solution 12 ng/ml; 5) calibration solution 60 ng/ml; 6) calibration solution 600 ng/ml; 7) blank (solvent mixture); 8) sample solution 1:1000; 7) sample solution 1:10.
HPLC/MS-MS Method HPLC: Agilent 1100, quat. pump (G1311A), autosampler CTC HTS PAL, degasser (G1322A) and column thermostat (G1316A); column: Oasis HLB 20 mm×2.1 mm, 25μ; temperature: 40° C.; mobile phase A: water+0.5 ml of formic acid/l; mobile phase B: acetonitrile+0.5 ml of formic acid/l; flow rate: 2.5 ml/min; stop time 1.5 min; gradient: 0 min 95% A, 5% B; ramp: 0-0.5 min 5% A, 95% B; 0.5-0.84 min 5% A, 95% B; ramp: 0.84-0.85 min 95% A, 5% B; 0.85-1.5 min 95% A, 5% B.

MS/MS: WATERS Quattro Micro Tandem MS/MS; Z-Spray API interface; HPLC-MS initial splitter 1:20; measurement in the ESI mode.

For each test substance, the instrument parameters are automatically optimized by injection of the stock solution described further above (second 1:100 dilution) using the MassLynx/QuanOptimize software.

C) EXEMPLARY EMBODIMENTS OF PHARMACEUTICAL COMPOSITIONS

The substances according to the invention can be converted into pharmaceutical preparations in the following ways:
Tablet:
Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.
Production:

The mixture of the compound of Example 1, lactose and starch is granulated with a 5% strength solution (m/m) of the PVP in water. The granules are dried and then mixed with magnesium stearate for 5 min. This mixture is compressed with a conventional tablet press (see above for format of the tablet).
Oral Suspension:
Composition:

1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound according to the invention.
Production:

The Rhodigel is suspended in ethanol, and the compound of Example 1 is added to the suspension. The water is added while stirring. The mixture is stirred for about 6 h until the swelling of the Rhodigel is complete.
Solution which can be Administered Intravenously:
Composition:

1 mg of the compound of Example 1, 15 g of polyethylene glycol 400 and 250 g of water for injections.

Production:

The compound of Example 1 is dissolved together with polyethylene glycol 400 in the water by stirring. This solution is sterilized by filtration (pore diameter 0.22 μm) and dispensed under aseptic conditions into heat-sterilized infusion bottles. These are closed with infusion stoppers and crimped caps.

The invention claimed is:
1. A compound of the formula,

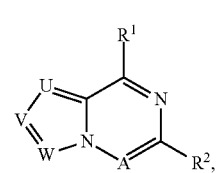

(I)

characterized in that
either
U represents N,
V represents $CR^{12}$,
W represents CH,
A represents $CR^{15}$,
or
U represents CH,
V represents $CR^{12}$,
W represents N,
A represents $CR^{15}$,
or
U represents $CR^{16}$,
V represents N,
W represents $CR^{17}$,
A represents N,
where
$R^{12}$ represents hydrogen, hydroxycarbonyl, aminocarbonyl, methyl, ethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, pyrrolidinylcarbonyl, piperidinylcarbonyl, piperazinylcarbonyl, morpholinylcarbonyl or —$CH_2R^{13}$,
where pyrrolidinylcarbonyl, piperidinylcarbonyl, piperazinylcarbonyl and morpholinylcarbonyl may be substituted by 1 to 2 substituents, where the substituents independently of one another are selected from the group consisting of oxo, methyl and ethyl,
and
where alkylcarbonyl, $C_2$-$C_4$-alkoxycarbonyl and $C_2$-$C_4$-alkylaminocarbonyl may be substituted by a substituent, where the substituent is selected from the group consisting of hydroxyl, amino, $C_1$-$C_4$-alkylamino, pyrrolidinyl, piperidinyl, piperazinyl and morpholinyl,
where pyrrolidinyl, piperidinyl, piperazinyl and morpholinyl may be substituted by 1 to 2 substituents, where the substituents independently of one another are selected from the group consisting of oxo, methyl and ethyl,
and
where
$R^{13}$ represents hydroxyl, amino, hydroxycarbonyl, aminocarbonyl, $C_1$-$C_4$-alkoxy, $C_1$-$C_4$-alkylamino, pyrrolidinyl, piperidinyl, piperazinyl or morpholinyl,
where pyrrolidinyl, piperidinyl, piperazinyl and morpholinyl may be substituted by 1 to 2 substituents, where the substituents independently of one another are selected from the group consisting of oxo, methyl and ethyl, $R^{15}$ represents hydrogen,
$R^{16}$ represents hydrogen or methyl,
$R^{17}$ represents hydrogen or methyl,
$R^1$ represents a group of the formula

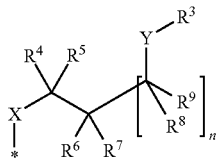

where
* is the point of attachment to the heterocycle,
n represents the number 0,
X represents $NR^{10}$,
where
$R^{10}$ represents hydrogen,
Y represents $NR^{11}$,
where
$R^{11}$ represents hydrogen or methyl,
$R^3$ represents 2-pyridyl, pyrimid-2-yl, 2-aminopyrimid-4-yl, 1,3-thiazol-2-yl or 1,3-thiazol-4-yl, where 2-pyridyl, pyrimid-2-yl, 1,3-thiazol-2-yl and 1,3-thiazol-4-yl are substituted by 1 or 2 substituents, where the substituents independently of one another are selected from the group consisting of fluorine, chlorine, cyano, nitro, amino and trifluoromethyl,
and
where 2-aminopyrimid-4-yl may be substituted by a substituent, where the substituent is selected from the group consisting of fluorine, chlorine, cyano, nitro, amino and trifluoromethyl,
$R^4$ represents hydrogen,
$R^5$ represents hydrogen or methyl,
$R^6$ represents hydrogen,
$R^7$ represents hydrogen or methyl,
$R^8$ represents hydrogen,
$R^9$ represents hydrogen or methyl,
$R^2$ represents phenyl, thienyl, pyrazolyl or pyridyl,
where phenyl, thienyl, pyrazolyl and pyridyl may be substituted by 1 to 2 substituents, where the substituents independently of one another are selected from the group consisting of halogen, trifluoromethyl, trifluoromethoxy, aminocarbonyl, $C_1$-$C_4$-alkyl, $C_1$-$C_4$-alkoxy, $C_1$-$C_4$-alkoxycarbonyl, $C_1$-$C_4$-alkylaminocarbonyl, pyrrolidinyl, piperidinyl, morpholinyl and morpholinylcarbonyl,
or one of its salts.

2. The compound as claimed in claim 1, characterized in that either
U represents N,
V represents $CR^{12}$,
W represents CH,
A represents $CR^{15}$,
or
U represents CH,
V represents $CR^{12}$,
W represents N,
A represents $CR^{15}$,
or
U represents $CR^{16}$,
V represents N,
W represents $CR^{17}$,
A represents N,
where
$R^{12}$ represents hydrogen, hydroxycarbonyl, methyl, ethyl, methoxycarbonyl, ethoxycarbonyl, $C_1$-$C_4$-alkylaminocarbonyl, piperidinylcarbonyl or morpholinylcarbonyl,
where piperidinylcarbonyl and morpholinylcarbonyl may be substituted by a substituent, where the substituent is selected from the group consisting of methyl and ethyl,
and
where $C_2$-$C_4$-alkylaminocarbonyl may be substituted by a substituent, where the substituent is selected from the group consisting of $C_1$-$C_4$-alkylamino, piperazinyl and morpholinyl, where piperazinyl and morpholinyl may be substituted by a substituent, where the substituent is selected from the group consisting of methyl and ethyl,
$R^{15}$ represents hydrogen,
$R^{16}$ represents methyl,
$R^{17}$ represents methyl,
$R^1$ represents a group of the formula

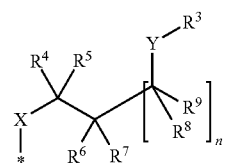

where
* is the point of attachment to the heterocycle,
n represents the number 0,
X represents $NR^{10}$,
where
$R^{10}$ represents hydrogen,
Y represents $NR^{11}$,
where
$R^{11}$ represents hydrogen or methyl,
$R^3$ represents a group of the formula

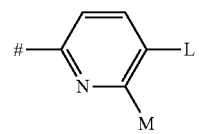

where
# is the point of attachment to Y,
L represents cyano, nitro or trifluoromethyl,
M represents hydrogen or amino,
$R^4$ represents hydrogen,
$R^5$ represents hydrogen or methyl,
$R^6$ represents hydrogen,
$R^7$ represents hydrogen or methyl,
$R^8$ represents hydrogen,
$R^9$ represents hydrogen,
$R^2$ represents phenyl,
where phenyl may be substituted by 1 to 2 substituents, where the substituents independently of one another are selected from the group consisting of fluorine, chlorine, trifluoromethyl, trifluoromethoxy, $C_1$-$C_3$-alkyl, methoxy, methoxycarbonyl and ethoxycarbonyl,
or one of its salts.

3. A pharmaceutical composition, comprising a compound as claimed in claim 1 in combination with an inert non-toxic pharmaceutically acceptable auxiliary.

4. The compound as claimed in claim 1, characterized in that $R^2$ is phenyl optionally substituted by 1 to 2 substituents, where the substituents independently of one another are selected from the group consisting of halogen, trifluoromethyl, trifluoromethoxy, aminocarbonyl, $C_1$-$C_4$-alkyl, $C_1$-$C_4$-alkoxy, $C_1$-$C_4$-alkoxycarbonyl, $C_1$-$C_4$-alkylaminocarbonyl, pyrrolidinyl, piperidinyl, morpholinyl and morpholinylcarbonyl.

5. A pharmaceutical composition, comprising a compound as claimed in claim 1 in combination with an inert non-toxic pharmaceutically acceptable auxiliary.

6. A pharmaceutical composition, comprising a compound as claimed in claim 2 in combination with an inert non-toxic pharmaceutically acceptable auxiliary.

7. A pharmaceutical composition, comprising a compound as claimed in claim 4 in combination with an inert non-toxic pharmaceutically acceptable auxiliary.

\* \* \* \* \*